(12) United States Patent
Toback et al.

(10) Patent No.: US 7,629,317 B2
(45) Date of Patent: *Dec. 8, 2009

(54) CONTROL OF GROWTH AND REPAIR OF GASTRO-INTESTINAL TISSUES BY GASTROKINES AND INHIBITORS

(75) Inventors: F. Gary Toback, Chicago, IL (US); Terence E. Martin, Chicago, IL (US); Margaret M. Walsh-Reitz, River Forest, IL (US)

(73) Assignee: The University of Chicago, Chicago, IL (US)

( * ) Notice: Subject to any disclaimer, the term of this patent is extended or adjusted under 35 U.S.C. 154(b) by 852 days.

This patent is subject to a terminal disclaimer.

(21) Appl. No.: 10/842,989

(22) Filed: May 11, 2004

(65) Prior Publication Data

US 2005/0031582 A1 Feb. 10, 2005

Related U.S. Application Data

(63) Continuation-in-part of application No. 10/473,571, filed as application No. PCT/US02/09885 on Mar. 29, 2002, which is a continuation-in-part of application No. 09/821,726, filed on Mar. 29, 2001, now Pat. No. 6,734,289.

(51) Int. Cl.
*A61K 38/18* (2006.01)
*C07K 14/475* (2006.01)
*C07K 11/00* (2006.01)

(52) U.S. Cl. .............................. 514/13; 514/2; 514/12; 514/14; 530/324; 530/325; 530/326; 530/399

(58) Field of Classification Search ........................ None
See application file for complete search history.

(56) References Cited

U.S. PATENT DOCUMENTS

| 5,644,026 | A | 7/1997 | Yamaguchi et al. |
| 6,670,119 | B1 | 12/2003 | Yoshikawa et al. |
| 6,734,289 | B2 | 5/2004 | Martin et al. |
| 6,913,919 | B2 | 7/2005 | Botstein et al. |

FOREIGN PATENT DOCUMENTS

| EP | 0972830 A1 | 1/2000 |
| WO | WO 98/37187 A1 | 8/1998 |
| WO | WO 99/07840 | 2/1999 |
| WO | WO 00/00610 | 1/2000 |
| WO | WO 00/43781 A2 | 7/2000 |
| WO | WO 00/73348 | 12/2000 |
| WO | WO 02/078640 | 10/2002 |

OTHER PUBLICATIONS

Shiozaki et al., Human stomach-specific gene, CA11, is down-regulated in gastric cancer. International Journal of Oncology, vol. 4:701-7 (Oct. 19, 2001).*

Aithal, N. H., et. al. (1994) "Glyceraldehyse-3-phosphate Dehydrogenase Modifier Protein is Associated with Microtubules in Kidney Epithelial Cells." *Am. J. Physiol.* 266:F612-F619.

Altschul, S.F., et al. (1997) "Gapped BLAST and PSI-BLAST: a New Generation of Protein Database Search Programs." *Nuc. Acids Res.* 25 (17):3389-3402.

Baczako, K et. al. (1995) "Lectin-Binding Properties of the Antral and Body Surface Mucosa in the Human Stomach—Are Difference Relevant for *Helicobacter pylon* Affinity?" *J. Pathol* 176:77-86.

Blaser, M.J. (1987) "Gastric *Campylobacter*-like Organisms, Gastritis, and Peptic Ulcer Disease." *Gastroenterol.* 93:371-383.

Boman, H.G. (1995) "Peptide Antibiotics and Their Role in Innate Immunity." *Ann. Rev. Immunol.* 13:61-92.

Cohen, GB., et al. (1995) "Modular Binding Domains in Signal Transduction Proteins." *Cell* 80:237-248.

Cregg, J.M., et al. (1993) "Recent Advances in the Expression of Foreign Genes in *Pichia pastoris*." *Bio/Technol.* 1:905-910.

Dignass, A.U., et al. (1998) "Adenine Nucleotides Modulate Epithelial Wound Healing In Vitro." *Eur. J. Clin. Invest.* 28:554-561.

Falk, P., et al. (1993) "An In vitro Adherence Assay Reveals That *Helicobacter pylori* Exhibits Cell Lineage-Specific Tropism in the Human Gastric Epithelium." *Proc. Nat. Acad. Sci. USA* 90:2035-2039.

Goodwin, C.S., et al., (1986) "*Campylocbacter* pyloridis, Gastritis, and Peptic Ulceration." *J. Clin. Pathol.* 39:353-356.

Hasty, P., et al. (1991) "The Length of Homology Required for Gene Targeting in Embryonic Stem Cells." *Mol. Cell. Biol.* 11:5586-5591.

Houston, M.E., et al. (1996) "Lactam Bridge Stabilization of α-Helices: The Role of Hydrophobicity in Controling Dimeric versus Monomeric α-Helices." *Biochem.* 35:10041-10050.

Janknecht, R., et al. (1991) "Rapid and Efficient Purification of Native Histidine-Tagged Protein Expressed by Recombinant Vaccinia Virus." *Proc. Nat. Acad. Sci. USA* 88:8972-8976.

Jeon, C.J., et al. (1994) "The Transcription Factor TFIIS Zinc Ribbon Dipeptide Asp-Glu is Critical for Stimulation of Elongation and RNA Cleavage by RNA Polymerase II." *Proc. Nat. Acad. Sci. USA* 91:9106-9110.

Johnson, F.R. and McMinn, R.M.H. (1970) "Microscopic Structure of Pyloric Epithelium of the Cat." *J. Anat.* 107:67-86.

Kartha, S. and Toback, F.G. (1985) "Purine Nucleotides Stimulate DNA Synthesis in Kidney Epithelial Cells in Culture." *Am. J. Physiol.* 249:F967-F972.

(Continued)

*Primary Examiner*—Marianne P Allen
*Assistant Examiner*—Regina M DeBerry
(74) *Attorney, Agent, or Firm*—Barnes & Thornburg LLP; Alice O. Martin

(57) ABSTRACT

A novel group of gastrokines called Gastric Antrum Mucosal Protein is characterized. A member of the group is designated AMP-18. AMP-18 genomic DNA, cDNA and the AMP-18 protein are sequenced for human, mouse and pig. The AMP-18 protein and active peptides derived from it are cellular growth factors. Surprisingly, peptides capable of inhibiting the effects of the complete protein, are also derived from the AMP-18 protein. Cytoprotection and control of mammalian gastro-intestinal tissue growth and repair (restitution) is facilitated by the use of the proteins, making the proteins candidates for therapies in inflammatory bowel disease, mucositis, and gastric ulcers.

4 Claims, 46 Drawing Sheets

OTHER PUBLICATIONS

Lacy, E.R. (1998) "Epithelial Restitution in the Gastrointestinal Tract." *J. Clin. Gastroenterol.* 10(Suppl 1):s72-s77.

Lieske, J.C., et al. (1994) "Renal Epithelial Cells Rapidly Bind and Internalize Calcium Oxalate Monohydrate Crystals." *Proc. Natl. Acad. Sci. USA* 91:6987-6991.s.

Lieske, J.C., et al. (1997) "Adhesion of Hydroxyapatite Crystals to Anionic Sites on the Surface of Renal Epithelial Cells." *Am. J. Physiol.* F224-F233.

Mansour, S., et al. (1988) "Disruption of the Proto-Oncogene *int-2* in Mouse Embryo-Derived Stem Cells: A General Strategy for Trageting Mutations to Non-Selectable Genes." *Nature* 336:348- 352.

Moore, K.S., et al. (1991) "Antimicrobial Peptides in the Stomach of *Xenpus laevis.*" *J. Biol. Chem.* 266 (2a):19851-19857.

Nguyen, J.T., et al. (1998) "Exploiting the Basis of Proline Recognition by SH3 and WW Domains: Design of N-Substituted Inhibitors." *Science* 282:2088-2092.

Nomura, A., et al. (1991) "*Helicobacter pylori* Infection and Gastric Carcinoma Among Japanese Americans in Hawaii." *N. Engl. J. Med.* 325 (16):1132-1136.

Nusrat, A., et al. (1992) "Intestinal Epithelial Restitution." *J. Clin. Invest.* 89:1501-1511.

Park, C.B., et al. (1997) "A Novel Antimicrobial Peptide From the Loach, *Misgurnus anguillicaudatus.*" *Febs Lett.* 411:173-178.

Parsonnet, J., et al. (1991) "*Helicobacter pylori* Infection of the Risk of Gastric Carcinoma." *N. Engl. J. Med.* 325 (16):1127-1131.

Podolsky, D.K. (1997) Healing the Epithelium: Solving the Problem from Two Sides. *J. Gastroenterol.* 32:122-126.

Powell, C.T. (1987) "Characterization of a Novel Messenger RNA and Immunochemical Detection of its Protein from Porcine Gastric Mucosa." *Ph.D. Dissertation*; The University of Chicago.

Quaroni, A., et al. (1979) "Epithelioid Cell Cultures From Rat Small Intestine." *J. Cell Biol.* 80:248-265.

Romanos, M.A. et al. (1992) "Foreign Gene Expression in Yeast: a Review" *Yeast* 8:423-488.

Rotimi, V.O., et al. (1990) "Acidity and Intestinal Bacteria: an In-Vitro Assessment of the Bactericidal Activity of Hydrochloric Acid on Intestinal Pathogens." *Afr. J. Med. med. Sci.* 19:275- 280.

Sands, B.E. And Podolsky, D.K. (1996) "The Trefoil Peptide Family." *Ann. Rev. Physiol.* 58:253-273.

Schlessinger, J. and Ullrich, A. (1992) "Growth Factor Signaling by Receptor Tyrosine Kinases." *Neuron* 9:383-391.

Sears, I.B., et al. (1998) "A Versatile Set of Vectors for Constitutive and Regulated Gene Expression in *Pichia pastoris.*" *Yeast* 14: 783-790.

Segarini, P.R., et al. (1987) "Membrane Binding Characteristics of Two Forms of Transforming Growth Factor-β" *J. Biol. Chem.* 262 (30):14655-14662.

Smith, D.B. And Johnson, K.S. (1988) "Single-Step Purification of Polypeptides Expressed in *Escherichia coli* as fusions with Glutathione *S*-transferase." *Gene* 67:31-40.

Toback, F.G. (1980) "Induction of Growth in Kidney Epithelial Cells in Culture by $Na^+$." *Proc. Nat. Acad. Sci.* 77 (11):6654-6656.

Yarden, Y. and Ullrich, A. (1988) "Molecular Analysis of Signal Transduction by Growth Factors." *Biochemistry* 27:3113-3119.

Yoo, O.J. et al. (1982) "Molecular Cloning and Nucleotide Sequence of Full-Length cDNA Coding for Porcine Gastrin." *PNAS* 79:1049-1053.

Database Biosis: Walsh-Reitz et al., "Accumulation of Specific Tight and Adherens Junction Proteins is Stimulated by Antrum Mucosal Protein-18 in Colonic Epithelial Cells in Culture and Mouse In Vivo," Database Accession No. PREV200300571862, Abstract (2003).

Database EMBL (2001): "Human PRO1005 (UNQ489) protein sequence SEQ ID No. 211," Accession No. AAB65209.

Martin et al., "A Novel Mitogenic Protein That is Highly Expressed in Cells of the Gastric Antrum Mucosa," *American Journal of Physiology: Gastrointestinal and Liver Physiology*, 285:2, pp. G332-G343 (2003).

Toback et al., "Peptide Fragments of AMP-18, A Novel Secreted Gastric Antrum Mucosal Protein, Are Mitogenic and Motogenic," *American Journal of Physiology: Gastrointestinal and Liver Physiology*, 285:2, G344-G353 (2003).

Waltz et al., "Functional Characterization of Domains Contained in Hepatocyte Growth Factor-Like Protein," *The Journal of Biological Chemistry*, 272:48 (1997).

Yoshikawa et al., "Isolation of Two Novel Genes, Down-Regulated in Gastric Cancer," *Japanese Journal of Cancer Research, Japanese Cancer Association*, Tokyo, Japan 91:5, pp. 456-463 (2000).

Clackson et al., "A Hot Spot of Binding Energy in a Hormone-Receptor Interface," *Science*, 267, 383-386 (1995).

Database EMBL (2000): "Human Signal Peptide Containing Protein HSPP-40 SEQ IP No. 49," Accession No. AAY87272.

Database EMBL (2001): "Mus Musculus Adult Male Stomach cDNA, Riken Full-Length Enriched Library, Clone: 2210420L15 Product: Weakly Similar to CA11 Protein [*Homo sapiens*], Full Insert Sequence," Accession No. AK008990.

Database EMBL (2001): "Sequence 14 From Patent WO0073348," Accession No. AX055699.

Huang et al., "Transforming Growth Factor Beta Peptide Antagonists and Their Conversion to Partial Agonists," *The Journal of Biological Chemistry*, 272: (43), 27155-27159 (1997).

Kawai et al., "Functional Annotation of a Full-Length Mouse cDNA Collection," *Nature*, 409, 685-690 (2001).

Schmassmann et al., "Roles of Hepatocyte Growth Factor and Its Receptor Met During Gastric Ulcer Healing in Rats," *Gastroenterology*, 113, 1858-1872 (1997).

Tarnawski, "Cellular and Molecular Mechanisms of Ulcer Healing," *Drugs of Today*, 33: (10), 697-706 (1997).

\* cited by examiner

```
   1  AGCTTTATAA CCATGTGATC CCATCTTATG GTTTCAATCC ATGCACAGGA

51  GGAAAATTGT GGGCACGAAG TTTCCAAAGG GAAAATTTAT AGATTGGTAG

101  TTAATGAAAT ACAGTTTTCC TCCTTGGCAA ATTTAATTTA CTAGCTTCAC

151  TGTATAGGAA AAAGCAGGAA AAAATTAAA ACCAACTCAC CTCCAAACCT

201  GTTTTGAGCT TTTACTTGTC TGCCCAATTG ATAGTTTCTA CTCTCTGCTT

251  TTGATGAAAA TATTTTTTAT TATTTTAATG TAACTTCTGA AAACTAAATT

301  ATCTAGAAGC AAATAAAAAG ATATTGCTTT TATAGTTCCC AGAAGGAAAA

351  AACAAACACT AGGAAAGTTC TATCTATCAG ATGGGGGAGA TGTGATGGAG

401  GCAGTGATAT TTGAGCTGAG CCTTGAACAA TGAACAGGAG TCTACCAAGC

451  GAGAGGCTAG CGGGTGGCCC TCAAGATAAA ACAACAGCAT GTACAAAGGC

501  ATGGAGACAT ACACATCTTG ACTCTTCCAG GAATGGTGGG AACGCTGGTG

551  GAGCTAGAAT GTAGGTACAT AGCATAAAGT GGCAGACGGG AAGCCTTTGG

601  AAATCTTATT ACATAGGACC CTGGATGCCA TTCCAATGAC TTTGAATTTT

651  CTGTAGGCTG CCAGCGAAAT TTCCAAGCGT GATAGAGTCA TGTCTATCTA

701  TGCACTTCAG AAAGACAACC TCAGGGTTAA TGAAGAAAAT GCATTGGAAT

751  ATAAGAAACT GGTGACCAGA GTGATCAATT GCATGACTGT TGTGAAAGTC

801  CAGGTGAGGG GAGCTGTGGG CAAGGTCAGA GTTGAGAGGC ATTTCAGAGA

851  TAAAATGACA GTAACTAAGT AGATGTCAGG CTGAGAAGAA AGGGCTGTAC

901  CAGATATATG GTGCTATCAT TAAGTGAGCT CAACATTGCA GAAAAGGGGT

951  AGGTTTGGTG GGAGTTGCTC ACAAAACATG TTTAGTCTAA GCAAAACCAT

1001  TGCCATGGGC TCAGATAAAA GTTAAGAAGT GGAAACCATT CCTACATTCC

1051  TATAGGAGCT GCTATCTGGA AGGCCTAGTA TACACGTGGC TTTTCAGCTG

1101  TGATTTTGTT TGATTTTAGG GATTATTCTT TTTCTGAATC TGAGCAATGT
```

FIG. 1A

```
1151  TAGCGTGTAA AATACTCACA CCCACAGCTT TGACTGGGTG AGAAGTTATC

1201  ATAAATCATA TTGAGTTTGT TGTGATACCT TCAGCTTCAA CAAGTGATGA

1251  GTCAGGTCAA CTCCATGTGA AAGTTCCTTG CTAAGCATGC AGATATTCTG

1301  AAAGGTTTCC TGGTACACTG GCTCATGGCA CAGATAGGAG AAATTGAGGA

1351  AGGTAAGTCT TTGACCCCAC CTGATAACAC CTAGTTTGAG TCAACCTGGT

1401  TAAGTACAAA TATGAGAAGG CTTCTCATTC AGGTCCATGC TTGCCTACTC

1451  CTCTGTCCAC TGCTTTCGTG AAGACAAGAT GAAGTTCACA GTGAGTAGAT

1501  TTTTCCTTTT GAATTTACCA CCAAATGATT GGAGACTGTC AATATTCTGA

1551  GATTTAGGAG GTTTGCTTCT TATGGCCCCA TCATGGAAAG TTTGTTTTAA

1601  AAAAATTCTC TCTTCAAACA CATGGACACA GAGAGGGGAA CAACACACAC

1651  CAGGTCCTGT TGGGGGGTGG AGAGTGAGGG GAGGGAACTT AGAGGACAGG

1701  TCAATAGGGG CAGCAAACCA CCATGGCACA CATATACCTA TGTAACAAAC

1751  CTGCACGTTC TGCACATGTA TCCCTTTTTT TTAGAAGAAG AAATAATGAA

1801  AAAAAACCTT TTTTCTATTT ATATAATCAT GGCATTTATA AGCATCTCTA

1851  TAGAGAAGGA TAATTGTGCT GAGATTAGAC AGCTGTCTGA GCACCTCACA

1901  CTGACCTATT TTAACAAAA TGACTTTCCA CATCACCTGA TTTCGGCTCC

1951  ATGCRGGGTA AGCAGTTCCT AAGCCCTAGA AAGTGCCGAT CATCCCTCAT

2001  TCTTGAATTC CTCCTTTTAT TTACCAAAAT TCCTGAGCAT GTTCAGGAAA

2051  GATGAAAAGC TTATTATCAA AATAAGTGGC TGAGATAGAC TTCTTGTCAC

2101  ATTTGTTACA GTAAATGGG TCTCCAAGAA AGAAAGATTT GCCTTGGGCT

2151  CTAGCATGGC CATTTATTTA AGAAAGCATC TGAAACATGA AGCTACCACA

2201  GCATCTCTCC TGTGGTTCCA GACGGAAGCC TGAGAGTCTA GGAGGAGGTG

2251  GACCGAGAAA CCCTGCCAAA GTAACTAGTA GTGCCGGGTT TCTCACAACA
```

FIG. 1B

```
2301  CGATGCAAAG GGGCTAGAAT CAGATGACTA TTTTCATGTT TCAACATACT

2351  ACACACTGGA AAACGTTACG GCAGACTCTA CTTTATAATG GGGCTGCAAA

2401  TGTAAAATGA CTACTAGAAC TAGGTCCTCT TAATAGCAGC AAAGTTTAAA

2451  AGGGTCAGAG GGAGCTCCAG ACACAGGTTA GATTTGATTT CTCTCCTAGT

2501  TCTGCTGTGA ACAAGAGGTA TAAGTTTGGC CAACTCACTT AACCCCTGAA

2551  GCTCAGTTAC CTTATCTGTA AAATGATTGC ATTGTACTAG GTGTTCTCTA

2601  AAATTTCTTC TACCTCTGAC TTTTTAGGAG ACTAATTTTT AACTCCTTTT

2651  TAAGCTATTG GGAGAAAAAT TTAATTTTTT TTCAAAAGTT ACCTTGAATC

2701  TCTAGAGCAG TTCTCAAAAC TATTTTGTCC CAGGCAAAGG AAATGAGACT

2751  AGGTACCCAG AATGAGGCAC CCTGCATAAA GCTCTGTGCT CTGAAAACCA

2801  ATGTCAGGGA CCCTGTGATA AATAATTAAA CCAAGTATCC TGGGACACTG

2851  CTAGTGACAT CGCCTCTGCT GATCACTCTT GCCAGCGAGA CACTCTATAC

2901  TTGCTTTCTC ATCATTGGCA TCCAAACTGC CTACTAATCC ATTGCTTTGG

2951  AAAGTTTTTT TTAATAAAAA GATTATTTCT ATTAGGAGGA AAACATCCCA

3001  TGTTAAATAG GAAAATTAAC TGAAATCATT TTCAGATGTG ATTTTTAGCA

3051  CTTATAGCCA TTTCAAACCA TGGTATTCAT TTATACTATG CTATTTATTG

3101  TAAAACTTCT TTTTTTTTCC AAGGAAAATA AGATAGTTTG CTTTATTTTA

3151  AAACAGTAAC TTTCTTATAT TGGGGCACTG ACCAAAATTC AATACTGGTA

3201  CAAATATGTT ACCTAGGGGG TCAAAATATG TGCCAGGTGA ATTTTCTGAA

3251  TTTCTCTAAA GAGAGAATTT TAAACCTTAT AAAACAATTA GAAACAAGTG

3301  AGTGAGAGGT GAGCATCAAC AACCTGTGTA ACATAAGCCA CAGTACAAAT

3351  TTAAGCTGAA TAACCAAGCC ATGTCAGTTA TCCCAAATCA TTTTTGTTAA

3401  TATTTAGGAG GATACACATA TTTTCAATAA CTTAAAAGTG AATCTTTACT

3451  CCTATCTCTT AATACTCGAA GAAGTATAAC TTTCTTCTTT TACTAGATTT
```

FIG. 1C

```
3501  AAATAATCCA AATATCTACT CAAGGTAGGA TGCTGTCATT AACTATAGCT

3551  GAGTTTATCC AAAATAGAAA AATCATGAAG ATTTATAAAG CATTTTAAAA

3601  ATAATCATTT ATAGCAAGTC CTTGAAAGCT CTAAATAAGA AAGGCAGTTC

3651  TCTACTTTCT AATAACACCT ATGGTTTATA TTACATAATA TAATTCAACA

3701  AAACAGCATT CTGACCAATG ATAATTTATA GGAAATTCAT TTGCCAAGTA

3751  TATGTTTTAT TATAAAGTTA ATATTTGAC CAATCTTAAA AATTTTAAA

3801  CTCTATTCTG ACATTTCCAG AAGTATTATC TTAGCAAGTC ATCTTTATGA

3851  TACCACTTAT TAAACTGAAG AGAAACAAGA TGGTACATTC TGGGTTTTAC

3901  TTTAAAAGGG ATTTGATTCA ATAATTTGAT TTATCACTAC TTGAAAATTA

3951  CATTTCTTC CTCAGACTGG ATGGCAATGA GATGAAAGCA GCTTTCCTGG

4001  CTCTCAACTT CCCTTCTTCA TCAATTTTTC CAGCGTTTCA TAAGGCCTAC

4051  ACTAAAAATT CTAAAACTAT ATATCACATT AATATAATTA CTTATAATTA

4101  ATCAGCAATT TCACATTATC GTTAAAACCT TTATGGTTAA AAAATGCAAG

4151  GTAAGAGAAG AAAAAAACAC ATTGAACTAG AACTGAACAC ATTGGTAAAA

4201  TTAGTGAATA CTTTTCATAA GCTTGGATAG AGGAAGAAAG AAGACATCAT

4251  TTTGCCATGT AACAGGAGAC CAATGTTATT TGTGATTTCA GATTGTCTTT

4301  GCTGGACTTC TTGGAGTCTT TCTAGCTCCT GCCCTAGCTA ACTATGTAAG

4351  TCTCACCTTT TCAAGTTTGC TACCAAAATG CATTTGCAAG GAAATGTGAT

4401  ATTAAATCAC TCTCAATCTC TTATAAACTT CAGAATATCA ACGTCAATGA

4451  TGACAACAAC AATGCTGGAA GTGGGCAGCA GTCAGTGAGT GTCAACAATG

4501  AACACAATGT GGCCAATGTT GACAATAACA ACGGATGGGA CTCCTGGAAT

4551  TCCATCTGGG ATTATGGAAA TGTAGGTAGT CAACGTGCAA TTTTCACTTT

4601  ATTGTTTAAA AATACGACTT CTTTTAACA AAAAATGTGC ATGTTAACCA

4651  TAAAGAAATT AAAAATAAAT TCTAATTACA CATAGCATAC AGTTATAAGT
```

FIG. 1D

```
4701  AAAGGTGACC ATTTTGCTCA TCCGATTTTG TTCCCTAGAG ATAACTACTG

4751  TTAATAAGTG TTGCATGATC AGTTAAAATT CAAACCAACA AACACTATGT

4801  TCAAGGGATT GTGGGTATAT ACAACAAATA TGAACATCCT TTTGCCTTGC

4851  CTGCAGATAC CCTCAATAAT GCTGAAAGAC TTATACAACA TTACTGCTTC

4901  CAAAGCTTAG ACTATCTCAC TTTGTTTTCA AGGAGGTTT TACGACCTTC

4951  TAAAGAGATT GAAATTGACA TTTCACCTAA AACTCGGGAA ATGTAAATGA

5001  CAATATTAAT TGGTAAGAGA GGAAAGAAGA AGAAAGAAG GAAGGAAAGA

5051  AGAAAGAAG GAAGGAAGGA AAGAAAGAAA GAAAGAAAGA AAGAGAGAGA

5101  AAGAAAGAAA AAGAAAAAAG AGAGAAAGAG AGAAGGAAAG AAAGAGAGAA

5151  GGAAAGGAAA AGAGAAGCAA AGAAAGAGAG GAGCAAAGAA AGGAACACTT

5201  AGCACTAGTT GGGAGACCCA ACTCTGGAAT TATCAGCTAT ATATTTAACA

5251  AACGTTATAC TTTTAAATAG CAAACTCTTT ATTGTTTCAA TTTTATCTGG

5301  TCAATTGGAA AAATAATTTT TGTCTTATCT GTCTCCTTGA AATGTGAGGA

5351  TCAAAGGAGA CTAAACATG ATAGCTTTTA AAGTCTATTT CAGTAAAACA

5401  GACTTATATA GAGGGGTTTT TATCATGCTG GAACCTGGAA ATAAAGCAAA

5451  CCAGTTAGAT GCTCAGTCTC TGCCCTCACA GAATTGCAGT CTGTCCCCAC

5501  AAATGTCAGC AATAGATATG ATTGCCAAGC AGTGCCCCAT CCAGTGCTCT

5551  TATCCCAGCT CATCACGATC TTGGAGTTCC CATTTCTCTC TGCAGGTGGA

5601  ACTGACCTCT GATAAGAAAA GCTCCTCGGA GAACACATGC CTCACTATTT

5651  GCCATCTACT TTAACAGGGC TTTGCTGCAA CCAGACTCTT TCAAAAGAAG

5701  ACATGCATTG TGCACAAAAT GAACAAGGAA GTCATGCCCT CCATTCAATC

5751  CCTTGATGCA CTGGTCAAGG AAAAGAAGGT AAAAATAAAA GGCTTTTTAT

5801  TTTTGGTGAG GGGAGAGGTT TTACATCCTT CAGTAAATAA CGAGAAGATC

5851  ACAGTCATTC CCTCTTGACT ACAGTATGTT GTAGTGTGCA GCACAAAGGG
```

FIG. 1E

```
5901  GGAAGTTATT GGTGATTGCC TGAGGGAAGG CAACTTCTGC CACATCAAAT
5951  GCTGTGGCTC ACACCTACCT CTACAACCGC TGAGCAAAGC ACTTGAAACC
6001  TTGACTGTTA GAGGAGCAAA GCTCTGGTCA CACCAATAGG AGCCTCAGTA
6051  CTTTGCCAAG GACATTTTTC TGCAAGAGTT AGTTAGGGTT ATTAGATTTA
6101  GCAAATGAAA ATAGAAGATA TCCAGTTAGG TTTGAATTTT AGGTAAGCAG
6151  CAGGTCTTTT TAGTATAATA TATCCTATGC AATATTTGGG ATATACTAAA
6201  AAAAGATCCA TTGTTATCTG AAATTCAAAT GTAACTGGGT ATTGTATATT
6251  TTGTCTGGCC ATACTAATCC AGGTGAGTGG AAAGAAGAGA TCCATAATGT
6301  TTTAAAATAT TTGCCTGAGT TCATATTCCT ATAACTGATA AATGAGTACC
6351  TTTCATTGAC AAGGTAGAGA AAATAAATAA ACTGCATTCT CAGAAGATGA
6401  TTATTACATA GTCTAATCCA AGGAATCTAT GATGACCAAA TGAGGTCCAA
6451  GTTGCAGAAT AAATTAAGCC TCAGACTTCT GTGTTTATGA GAAGCTGAGG
6501  TTTCAAACCA GGTAAATCCC TTAGGACACT TAGAAATGCT AAGATATACA
6551  GAATAAGCTA GAAATGGCTC TTCTTCATCT TGATTATGGA AAAATTTAGC
6601  TGAGCAACAC TCACTGTTGG CCTCGTATAC CCCTCAAGTC AACAAACCAC
6651  TGGGCTTGGC ATTCATTCTC TCCCATTCTT CCTTTCTACC TCTCTTTTCC
6701  ACACTCAGCT TCAGGGTAAG GGACCAGGAG GACCACCTCC CAAGGGCCTG
6751  ATGTACTCAG TCAACCCAAA CAAAGTCGAT GACCTGAGCA AGTTCGGAAA
6801  AAACATTGCA ACATGTGTC GTGGGATTCC AACATACATG GCTGAGGAGA
6851  TGCAAGGTGA GTAGCATCCC TACTGTGCAC CCCAAGTTAG TGCTGGTGGG
6901  ATTGTCAGAC TATCCTCGCG CGTGTCCATA GTGGGCACCA GTGATGCAGG
6951  GATGGTCATC AAGGCCAACA TTTGTGCAGT GCTTGCTCTG TGCCAGGTAC
7001  TGTTCTATGT GCTTTAAGTG TGTTAACTCG GTTCTTCACA GCAATCTTAT
7051  AGGTTCTATT TTAATCCTAC TTTATGGATG AGGAAACTGA GGTACAGAGA
```

FIG. 1F

```
7101  GGTCACAAAA TCCTTGCCTG GGTCAATTCC AAGCATTTTG GCTGTGGATT

7151  CTGTGCTCTT AAATATTATG GAACACTGCC TTTTAAGTGT GAATCAAGAG

7201  TAGACTCAAG TCATATTCAA AAGAATGCAT GAATGGCTAA ATGAAAGAAG

7251  AATGCTAATA GAATCTATTA ACTTTCTATA GCTCAGACAA TCACTTAATT

7301  TCTGGACATT CAAAGAACAG CTGCACACAA ACAAAGTGTC TACCTAGGGA

7351  CCTAACTTAA TGGCAATTTT CCAGATCTCT GAATTGATTG ATTTCATCAC

7401  AACAAGTAGA TAAACCTTGA CATTAGCACA TAGCTAGTTT GGAAACCCCT

7451  ACTCCCCCAA TCCCCTCCAA GAAAAGAGTC CTTAAATAGA CATTAATATA

7501  GGCTTCTTCT TTTCTCTTTA TTAGAGGCAA GCCTGTTTTT TTACTCAGGA

7551  ACGTGCTACA CGACCAGTGT ACTATGGATT GTGGACATTT CCTTCTGTGG

7601  AGACACGGTG GAGAACTAAA CAATTTTTTA AAGCCACTAT GGATTTAGTC

7651  ATCTGAATAT GCTGTGCAGA AAAAATATGG GCTCCAGTGG TTTTTACCAT

7701  GTCATTCTGA AATTTTTCTC TACTAGTTAT GTTTGATTTC TTTAAGTTTC

7751  AATAAAATCA TTTAGCATTG AATTCAGTGT ATACTCACAT TTCTTACAAT

7801  TTCTTATGAC TTGGAATGCA CAGGATCAAA AATGCAATGT GGTGGTGGCA

7851  AGTTGTTGAA GTGCATTAGA CTCAACTGCT AGCCTATATT CAAGACCTGT

7901  CTCCTGTAAA GAACCCCTTC AGGTGCTTCA GACACCACTA ACCACAACCC

7951  TGGGAATGGT TCCAATACTC TCCTACTCCT CTGTCCACTG CTTAA (SEQ ID NO: 1)
```

FIG. 1G

```
  1  CATGCTTGCC TACTCCTCTG TCCACTGCTT TCGTGAAGAC AAGATGAAGT
 51  TCACAATTGT CTTTGCTGGA CTTCTTGGAG TCTTTCTAGC TCCTGCCCTA
101  GCTAACTATA ATATCAACGT CAATGATGAC AACAACAATG CTGGAAGTGG
151  GCAGCAGTCA GTGAGTGTCA ACAATGAACA CAATGTGGCC AATGTTGACA
201  ATAACAACGG ATGGGACTCC TGGAATTCCA TCTGGGATTA TGGAAATGGC
251  TTTGCTGCAA CCAGACTCTT TCAAAAGAAG ACATGCATTG TGCACAAAAT
301  GAACAAGGAA GTCATGCCCT CCATTCAATC CCTTGATGCA CTGGTCAAGG
351  AAAAGAAGCT TCAGGGTAAG GGACCAGGAG GACCACCTCC CAAGGGCCTG
401  ATGTACTCAG TCAACCCAAA CAAAGTCGAT GACCTGAGCA AGTTCGGAAA
451  AAACATTGCA ACATGTGTC GTGGGATTCC AACATACATG GCTGAGGAGA
501  TGCAAGAGGC AAGCCTGTTT TTTTACTCAG GAACGTGCTA CACGACCAGT
551  GTACTATGGA TTGTGGACAT TTCCTTCTGT GGAGACACGG TGGAGAACTA
601  AACAATTTTT TAAAGCCACT ATGGATTTAG TCATCTGAAT ATGCTGTGCA
651  GAAAAAATAT GGGCTCCAGT GGTTTTTACC ATGTCATTCT GAAATTTTTC
701  TCTACTAGTT ATGTTTGATT TCTTTAAGTT TCAATAAAAT CATTTAGCAT
751  TG
```

FIG. 2

| | | |
|---|---|---|
| 1 | MKFTIVFAGLLGVFLAPALANYNIDVNDDNNNAGSGQQSVSVNNEHNVAN | 50 |
| 51 | VDNNNGWDSWNSIWDYGNGFAATRLFQKKTCIVHKMKKEVMPSIQSLDAL | 100 |
| 101 | VKEKKLQGKGPGGPPPKGLMYSVNPNKVDDLSKFGKNIANMCRGIPTYMA | 150 |
| 151 | EEMQEASLFFYSGTCYTTSVLWIVDISFCGDTVEN | 185 |

FIG. 3

```
   1 GAATTCAAAC AGCAGGCCAT CTTTCACCAG CACTATCCGA ATCTAGCCAT

51 ACCAGCATTC TAGAAGAGAT GCAGGCAGTG AGCTAAGCAT CAGACCCCTG

101 CAGCCCTGTA AGCTCCAGAC CATGGAGAAG AGGAAGGTTG TGGGTTCAAG

151 GAGCTTTTCA GAGTGGAAAT CTGTGGATCA GTGATTTATA AAACACAGTT

201 TCCCCCTTTA TTAGATTTGA ACCACCAGCT TCAGTTGTAG AAGAGAACAG

251 GTTAAAAAAT AATAAGTGTC AGTCAGTTCT CCTTCAAAAC TATTTTAAAC

301 GTTTACTTAT TTTGCCAAGT GACAGTCTCT GCTTCCTCTC CTAGGAGAAG

351 TCTTCCCTTA TTTTAATATA ATATTTGAAA GTTTTCATTA TCTAGAGCAG

401 TGGTTCTCAT CCTGTGGGCC ATGAGCCCTT TGGGGGGGTT GAACGACCCT

451 TTCACAGGGG TCACATATCA GATATCCTGC ATCTTAGCTA TTTACATTAT

501 GATTCATAAC AGTAGCAAAA TTAGTTAGGA AGTAGGAACA AAATAACGTT

551 ATGGTTGTGG TCACCACTAT GTTAGAGGGT CCGCAGCATT CAGAGGGTTG

601 AGAACTGTTG TTCTAGAGGC AAATAAGAAG ACAGAGTTCC TTGATAGGGC

651 CCAGAGGCAG TGAAAGAAGT TTCCACGTAG AAAGTGAAGA AGGTCTGGTG

701 TCCGAAGCAG TGAGGAACTT AAAAAAAGAA AACCAAAAAC ATTGCCAACT

751 AACAGTCCAG GAGAAGAGCG GGGCATGAAA GGCTGAGTTC CCATGGGATG

801 CCTTGAATGG AATCAGAGTG TGGGAAAATT GGTGTGGCTG GAAGGCAGGT

851 GCCGGGCATC TCAGACGCTG GTAGCTGGGG AAACAGGAAA CCCCTTTAGG

901 ATCCCAAGAT GCCATTCCAA TGAGCTTGAG ATTTTTCTCA TGGACTGCCA

951 GTGAATGTTT CTACGCTCCG GAAATTAATG TTTACTTATT TTCCATATTC

1001 TAGGGGAGAA CCCTGGGAAA AATGGAGGAC ATTCATTGAA ATATCTGAGT

1051 CCTGGGATAA GGCAGGCTTG GTCCTACAAC TCTGGTAAAA GTCCATCAGG

1101 AAGTGCCTTG ACCAAGGCTG GAGTGGAGAG CTGTTGGTGA GATGTAAGGG
```

FIG. 4A

1151 CAAGGTTTAG TTGCTAGATA TGTAGATGGC AAGATGGTGC TGCCAACAGC

1201 CCCCAGAGCT CTAACCCACT GAGAAACCCA GGAATGAATG ATGGGAGATG

1251 GCTTTGGTGC CAGCTGCTAG TGACATGGCT GGAAAGCTGC ACTGGCTTCG

1301 AGGCCAGACA ATTCCTCAAG GAAACATCTG GCCAGGGTGC AAGGGCCAGT

1351 TTCCTTCCTT GGAGTTCCTT TCACAGCTAA GAACATCATC CCCCAACCAC

1401 TGGTTTTGTT AAAAAGTTTT CAGTATGACT TGAGCATGGT CAAGAAGCAT

1451 AGAGAGGGGG AAATAAGGGT GGAAGGAGCT GGAGAAAGCT TACAATAGGA

1501 CTGGGTAAAG GGAAGGAGAA GAAACCATTC CCGCATTCCC ATAGGAGCCA

1551 GTACCAGGAA GGGCAGGTGT ACACACAGAT CTCATCTAAG GCCATGTTTG

1601 GTTTAGGGAT TACTCTTCTC CCGAATCTGA GCAGCAGCAA TACGTAAAAT

1651 ACCCACACCC ATGGCTTCCA TATTCCAGAA CTTATCACAA ACCGTGTAGA

1701 GTTTACTGAG ATACCTTCGT CAGAGGATGA GTCAGAGGCC TCCTGCCTAA

1751 GGGCCCTACT GAGCAGGCAG CTAAAGGCTT CCGGGCCTCT GCAGCTCCAC

1801 AGATACAGGA GAGGGAAGCA GATAAGCCGT GGACTCCACC TGAGCACACC

1851 TAGCTTGAGC AAAGCTGGTC AGGTACAAAT AGCAGAGGGC TGAATGTCTG

1901 TGAGCACGCC GCCTGATCCT CTGCTCCACC ACACTCCTGC CGCCATGAAG

1951 CTCACAGTAA GTCAGATCTT CTTTTCAATG CAGCACCATA CAACATTAAT

2001 AGTCAGGGGT GAGGGGGTCT GACTCTTACG GCACTGTTAC CATAGTGGAA

2051 ATATTCTCCT TTCTTTTCAT GGAATCATGG TGTTTACAAG CATGTCCATA

2101 GAGAAGAAGA ATTGCCCCGG AAGAGCCTGT CACAGGCTGA ATACTGTAGA

2151 ATTGTCTTTC ACACCATCTG TTCCAAGGTT CTACTTAAGA CGAGCAGTCT

2201 CTGGGCTCCA GAAAGAGTCT TTCTTAGCCT TGATCTCTTT CTTATTTCTG

2251 ATTTCTCCTT TCTTATCCAT GATTTCCACT TTTACCAGTT CTGGGCATGT

FIG. 4B

```
2301  TCCGGTCAGA CTGGAAGATC ACTGTTGTCA AAACTAGTCT TCAACACTCT

2351  TGGCTGTTAA CATGAAAACA ACGGTCCTTG GGCCCTGTGC AAGCATTTCT

2401  TGGAGAAAGT CTCTGGGGAT GAAGCTATCT CAGTTTCCCC ACTGAAGTCC

2451  TAGGATACAG AGGCTCAAAC AGAGTGCACA TATTCAATTT CAGCATACTC

2501  TATTGGCGCT GCTTTATGAA TCATATGAAT TTATGGAATT GGAAATGTAA

2551  ACTATGACCA AGAAGCGTCC ACCTCAGAAC AGGTTGGGTG GGGAACTCCA

2601  AGCACAGGCC AGAGGGCTGC GTTTCTCTTC TAGTTCTGTC TAGAGGAGTG

2651  GTTCTCGACC TTCCTAATGC TGTGACCCTT AATACAGTT CCTCACGTTG

2701  TCGTGACTCC CAGCCATAAA ATTACTTTCA TTGCTACTGC ATAACTGTAA

2751  TTTTGCTACC ATTATGAGTT GTAATGTAAA TATCTGATAT GCAAGATACC

2801  AGATAACCTA AGAAACGGTT GTTTGACCTT TAAAGGGGTC ACAACCCACA

2851  GGTGGAGAAC TACTGGTCTA GGGTCCTTTA CAGTCCTTTA GCTGCCTCAT

2901  TTACAGGAGA TAACATCATG CTCAAAAACT CCCTCCACAT TTGGCTTTTT

2951  GGGTTGTTTT GTTTTGTTTT TCAAGACAGG GTTTCTCTGT GTAGCCCTGG

3001  CTGTCCTGGA ACTCACCTTT GTAGACCAGG CTGGCCTCGA ACTCAGAAAT

3051  CCGCCTGCTT CTGCCTCCTG AGCGCTGGGA TTAAAGGCGT GCGCCACCAT

3101  GTCTGGCTCA CATCTGGCTT TTTAAGAGAC CGATTTTAAC TTCTTGCATT

3151  GAAAATAAAT ATAGTAGAAA TGCTTAACCT ACTAAGACAA TAAAAACAGG

3201  ATTCCTTCTG CTAGGAAGAA CACGTTCCAG ACTAAGGAAA AAAACCTTTT

3251  CAGGGCTTTC ATTACACTGT GCCATGCACT AATTTATGT TTTCTTCATC

3301  AGTTTTCAGT GTCTGAAATT CAGTGTCAAA ATTCTAAGAC TACATATGAA
```

FIG. 4C

```
3351  TATCATTACA GTAACTCAGC AATTCTATGT TACCAGTAAG TTTTTCTGTA

3401  GTTTAAAAAA AAGGTGGAAG AAGAAAGCAC AGATAGTTTA GCACATGGGT

3451  AAAATCAGTA ACTATTTCTG ATGAGCTTGG TGAAGATGCT GTAAACCATG

3501  CGACCACCAG TCCTGTTCTC TGTGCTTTCA GATGTTCGTC GTGGGTCTGC

3551  TTGGCCTCCT TGCAGCTCCT GGTTTTGCTT ACGTAAGTCT CATTTTTCTG

3601  AAGTTCATTG TCAAAACTGC ATTTACAGTG AAATGTGATC TTAAGTCACC

3651  CTCTGCTTCT TATGAACATT AGACGGTCAA CATCAATGGT AATGATGGCA

3701  ATGTAGACGG AAGTGGACAG CATTCGGTGA GCATCAATGG TGTGCACAAC

3751  GTGGCCAATA TCGACAACAA TAACGGCTGG GACTCCTGGA ATAGCCTCTG

3801  GGACTATGAA AACGTATGTA ATGGACACAC AGGGTAAAGA TATGGTGTAG

3851  CCACCACCCA TTAAAATTTC TGAGGTGAAT TCTAGCTGTT CATGAACATT

3901  AAAAGCTACC AGTAAAAGTG CCCATTCCAC TCAAAACAAT TTTACTTTTT

3951  TGCATATAAT TATTGCTAAT AAGTATTACA CAATAGGTCG AAATTCAAAG

4001  GGATCAATAG TAAGGATAAA AACTATGTAC AAAGACAAAC ACAGCATCCT

4051  TTGGTCTTCC CTGCAGAGAG TCTCCATGAT GTTAAAGGTC AATGTTTTA

4101  TGGAGGCTGA ATGAAATACG AATGCCTCTG TGATGGAAAA GGCCCAACAT

4151  CTTATGGAGA ATGAGTGAAG TATGAATGCT ATTAGTTGTA AGAGAAGGCG

4201  ATGCAAAGCA ACACTTGGCA CCACCTGCCA ATTACTACTT TCCTATTTAA

4251  ATGTAGTTTA AAAAGCAAAG CCTGTCTTCC CTGCCTCCTG GAAACACTGC

4301  GGATGGAGGT AGACCAAGGT ATGACAGCCT TTAAAAGTTT GTCAGCAAAA

4351  CACTCCCCCA TACACACATA CACACACCCT CCTACTACAC TGGAACTGAA
```

FIG. 4D

```
4401  GCAAAGGCAG TGGGTTAGAT ATATCCACCC TCTAAGAGTT TGCAGGTCAT

4451  CTATATATGA TAGCCAGAGA CACAACTGCA GGACAGCCAG ACTCTGAGCA

4501  CTCTCCCCAG CTCCTTGTAG CTCTGTTTCA GTGGTGACTT GTGACAAGAA

4551  TCCTGGGGAA CCTGTGCCTC ACTGTTCTCT GTCTTCTTTA ATAGAGTTTC

4601  GCTGCCACGA GACTCTTCTC CAAGAAGTCA TGCATTGTGC ACAGAATGAA

4651  CAAGGATGCC ATGCCCTCCC TTCAGGACCT CGATACAATG GTCAAGGAAC

4701  AGAAGGTAAA GTCCTGCCTT CTTCTTTGGA GTGACAGGAA GTCTTACAGT

4751  CTCCAGTACA CAGTGAAGTC ACCCCATTC CCTCTTTGGT GGAGCATGAC

4801  AGCATGTTTG TCATGATAAA TGCCACAAAC ATGTAAAACT GTTCAGTGTC

4851  TGCCTGAATG GAGGGTGGCT TCCACTGTGT CAGATGCCGT GGCCCACATC

4901  TGCCTCTGCA GGGTCCAGTA AAGCACTGGC TATCTTGAGT GTCAGAGACC

4951  CAAAGGTCTG TACACTTCAG TACAAGCCCT CCATATTTCA AGGGCACACT

5001  CCTACAGTCG TTGGGGTTAT CAGAACTAGC AAACATAGAG ACTGGATTTT

5051  CAGATGAAAA GAAATCCTTT TTAAAGTCTA AGTATGCCTT ATACAATGTT

5101  TGAGATATTC TCAATACTAA AAAAAAAAAA ATTGTTGCTT GCTTGAAAAT

5151  CAAATGTAAC CAAGTGTCCT ATATCCAGTG TCAATCATGG CTGTAGTAGA

5201  TGGGAAGAGG GAGCCCGTGG TTTTCACAGT CAGACGCCTG AGTTATTCTT

5251  CTAAGTGATA AATTGGTTCC TATAACAAGC AAGCCAGTGA ATATAAATAA

5301  GCTCTATCTC AGAAGTTATC CTGTAGTGCT ACCCTAGAAT CTAAGAGAGC

5351  AAAAGTGCTT CAAATTTCAG AATAAGTTTT GCTTTGGACT TCTGTTTTTC

5401  TAAACAACTA TAACTTCAAA CCATCTAAGC CTCGTGGGAC ACTTAGAAAT

5451  ACCAAGCCAT TCAAAGCTAG AATTGTTTCT TCACCTTACT TGAAAACAAA
```

FIG. 4E

5501 ATGACAACCA AAAATTGTCC CCACTGCCCT TGTACATCTT CAGATCAGTA

5551 AAGTCCTGGG CTCAGGGATC ATTCACTTTC TTTCTTTCCT TTCACACTCA

5601 ACTTCAGGGT AAAGGGCCTG GAGGAGCTCC TCCCAAGGAC TTGATGTACT

5651 CCGTCAACCC TACCAGAGTG GAGGACCTGA ATACATTCGG ACCAAAGATT

5701 GCTGGCATGT GCAGGGGCAT CCCTACCTAT GTGGCCGAGG AGATTCCAGG

5751 TGTGTACCCT GAGATGCTGT ATATCCCAAT GCAGTACTGA GAGAGCCATC

5801 AGACACTCTA AAGTGTGACC ACAGACGGAC CAATCATGTG GATTATCAGA

5851 GCAAACACTT GCTTGCTCCT TGTCAGACAG TTGTCCATGC TTCAAAAGTT

5901 CATTAAAAAA AATAGTTCAC AGGCTCCTCA CAGAAACCTT AGTAGAATCC

5951 ACAGCTTCTG CTCTTAGTCT TACTTTTTAG AAACTGAGAC CCAGAGAAAG

6001 GTCACAAAAC TTTTGTCTGG CTCAGGTTCT ATGTCTTTAA CTTTATAGAA

6051 TACCGTCTTT CTGGGTGGGT GGGCTCTAGA GTAAACTTCA AGTGAGTTCA

6101 AGGAAAGCAT GAGAAGTAGG GAAGACCAAA TGAAAGGAGA ATGCCAATGA

6151 AATCTATCGA TTCTATAGCG CCAATGCTTA ACTCCTAGGC GTTCAAAGAA

6201 TAGTATCCAC AAGGTGTCAG CCTAAGATCC TAATCTAACA GCAAGTTTTC

6251 AGATCTCTGA AGTGAAAAGA GAAAGCAAGA GAGGAACAGA GACAGAAACA

6301 GTAAGAGACA GAGAGGCAGA GACAAAGAGA CAGGGAGAAT AGAGAGGGAT

6351 TAAAATTAAT ATATAGTTTA GAAATTACGA CTCCTCACAG TCCCTGCAGA

6401 GTCCTAGGAT AGGCACTGAT TTGGACTTCT TTTCTTCTCA CTAGGACCAA

6451 ACCAGCCTTT GTACTCAAAG AAGTGCTACA CAGCTGACAT ACTCTGGATT

6501 CTGCGGATGT CCTTCTGTGG AACATCAGTG GAGACATACT AGAAGTCACA

6551 GGAAAACAAC CCGTGGGCTC TGACCATCGC AATGCTTGAT TATGAGAGTG

FIG. 4F

```
6601  TTCTCTGGGG GTTGTGATTA GCTTCTTTAA GGCTCAATAA ACCCACGTGG

6651  CAGCACATCC AGTTTGTAAT GACATGCCTC ATGACTTCTA TGGGAGTCCA

6701  ATGTGGCACC TGCCAGCCTG TATTCAGGAC CTCTCCGCTA TAAAGCATCC

6751  CTCCAGAGTT TTCAAATACT ACAAAGCACA GCCTGGGTTT GGGCTCAGAT

6801  AGGCCACTGC TGCCTGACTA CATTACAGAC AAACAAGTTT TAAAAGAAAG

6851  AAAAAAGAGC TCAGAGTGGC TGGAATCAGC AAGGGTGTTT TTCCTGCAAG

6901  GAGCCAGAAG TATCAATAAT CACCCAAGGA GGAGACACTG GAATGAGAG

6951  ACTAGAACAC ACGCCTGCAG ATACGGAGAA CCTCAGCATT GCCGCTCTCT

7001  CCCATAACTG CACACCCCCT TCTGTAAACT CTGCTTCTTT CTTTCACCTG

7051  AAGATGGCCC TTGCTTTTTT TTATTATAGG ACANGATAAC TAGACCAGAA

7101  AGTCAACCTG ACTCTCTACA TTTATATGTC TTCCCAGNTC AAGAAATATT

7151  ATTTACTGGT GAATGGCACT TCTATATTCC CTTGGTTCAA TAAGTCTACA

7201  GGATCCATTC ATTGACAGGC CAAGAGTGAG ATCACATGAT ACCCAAGCAC

7251  ATGGGTCTTT CCTTGAAGGA GAAGGATCCA (SEQ ID NO: 4)
```

FIG. 4G

```
  1  ATGTTCGTCGTGGGTCTGCTTGGCCTCCTTGCAGCTCCTGGTTTTGCTTACACGGTCAAC

61  ATCAATGGTAATGATGGCAATGTAGACGGAAGTGGACAGCATTCGGTGAGCATCAATGGT

121  GTGCACAACGTGGCCAATATCGACAACAATAACGGCTGGGACTCCTGGAATAGCCTCTGG

181  GACTATGAAAACAGTTTCGCTGCCACGAGACTCTTCTCCAAGAAGTCATGCATTGTGCAC

241  AGAATGAACAAGGATGCCATGCCCTCCCTTCAGGACCTCGATACAATGGTCAAGGAACAG

301  AAGGGTAAAGGGCCTGGAGGAGCTCCTCCCAAGGACTTGATGTACTCCGTCAACCCTACC

361  AGAGTGGAGGACCTGAATACATTCGGACCAAAGATTGCTGGCATGTGCAGGGGCATCCCT

441  ACCTATGTGGCCGAGGAGATTCCAGGACCAAACCAGCCTTTGTACTCAAAGAAGTGCTAC

501  ACAGCTGACATACTCTGGATTCTGCGGATGTCCTTTTGTGGAACATCAGTGGAGACATAC

561  TAG
```

FIG. 5

1   MKLTMFVVGL LGLLAAPGFA YTVNINGNDG NVDGSGQQSV SINGVHNVAN

51  IDNNNGWDSW NSLWDYENSF AATRLFSKKS CIVHRMNKDA MPSLQDLDTM

101 VKEQKGKGPG GAPPKDLMYS VNPTRVEDLN TFGPKIAGMC RGIPTYVAEE

151 IPGPNQPLYS KKCYTADILW ILRMSFCGTS VETY

FIG. 6

```
  1  atgcctgact tctcacttca ttgcattggt gaagccaaga tgaagttcac
 51  aattgccttt gctggacttc ttggtgtctt cctgactcct gcccttgctg
101  actatagtat cagtgtcaac gacgacggca acagtggtgg aagtgggcag
151  cagtcagtga gtgtcaacaa tgaacacaac gtggccaacg ttgacaataa
201  caatggatgg aactcctgga atgccctctg ggactataga actggctttg
251  ctgtaaccag actcttcgag aagaagtcat gcattgtgca caaaatgaag
301  aaggaagcca tgccctccct tcaagccctt gatgcgctgg tcaaggaaaa
351  gaagcttcag ggtaagggcc caggggacc  acctcccaag agcctgaggt
401  actcagtcaa ccccaacaga gtcgacaacc tggacaagtt tggaaaatcc
451  atcgttgcca tgtgcaaggg gattccaaca tacatggctg aagagattca
501  aggagcaaac ctgatttcgt actcagaaaa gtgcatcagt gccaatatac
551  tctggattct taacatttcc ttctgtggag gaatagcgga gaactaa
```

FIG. 7

```
1    MKFTIAFAGL LGVFLTPALA DYSISVNDDG NSGGSGQQSV SVNNEHNVAN

51   VDNNNGWNSW NALWDYRTGF AVTRLFEKKS CIVHKMKKEA MPSLQALDAL

101  VKEKKLQGKG PGGPPPKSLR YSVNPNRVDN LDKFGKSIVA MCKGIPTYMA

151  EEIQGANLIS YSEKCISANI LWILNISFCG GIAEN
```

FIG. 8

| Human | 1 | MKFTIVFAGLLGVFLAPALANYNIDVNDDNNNAGSGQQSVSVNNEHNVAN | 50 |
| --- | --- | --- | --- |
| Pig | 1 | MKFTIAFAGLLGVFLTPALADYSISVNDDGNSGGSGQQSVSVNNEHNVAN | 50 |
| | 51 | VDNNNGWDSWNSIWDYGNGFAATRLFQKKTCIVHKMKKEVMPSIQSLDAL | 100 |
| | 51 | VDNNNGWNSWNALWSYRTGFAVTRLFRKKSCIVHKMKKEAMPSLQALDAL | 100 |
| | 101 | VKEKKLQGKGPGGPPPKGLMYSVNPNKVDDLSKFGKNIANMCRGIPTYMA | 150 |
| | 101 | VKEKKLQGKGPGGPPPKSLRYSVNPNRVDNLDKFGKSIVAMCKGIPTYMA | 150 |
| | 151 | EEMQEASLFFYSGTCYTTSVLWIVDISFCGDTVEN | 185 |
| | 151 | EEIQGANLISYSEKCISANILWILNISFCGGIAEN | 185 |

FIG. 9

```
              1                                                              50
Human    MKFTIVF.AG LLGVFLAPAL ANYNIDVN.D DNNNAGSGQQ SVSVNNEHNV Pig      MKFTIAF.AG LLGVFLTPAL ADYSISVN.D DGNSGGSGQQ SVSVNNEHNV Mouse    MKLTM.FVVG LLGLLAAPGF A.YTVNINGN DGNVDGSGQQ SVSINGVHNV 51                                                             100
Human    ANVDNNNGWD SWNSIWDYGN GFAATRLFQK KTCIVHKMNK EVMPSIQSLD Pig      ANVDNNNGWN SWNALWDYRT GFAVTRLFEK KSCIVHKMKK EAMPSLQALD Mouse    ANIDNNNGWD SWNSLWDYEN SFAATRLFSK KSCIVHRMNK DAMPSLQDLD 101                                                            150
Human    ALVKEKKLQG KGPGGPPPKG LMYSVNPNKV DDLSKFGKNI ANMCRGIPTY Pig      ALVKEKKLQG KGPGGPPPKS LRYSVNPNRV DNLDKFGKSI VAMCKGIPTY Mouse    TMVKEQK..G KGPGGAPPKD LMYSVNPTRV EDLNTFGPKI AGMCRGIPTY 151                                                     188
Human    MAEEMQEASL FFYSGTCYTT SVLWIVDISF CGDTVEN Pig      MAEEIQGANL ISYSEKCISA NILWILNISF CGGIAEN Mouse    VAEEIPGPNQ PLYSKKCYTA DILWILRMSF CGTSVETY
```

FIG. 10

A mrgshhhhhgs      21 NYNIDVNDDNNNAGSGQQSVSVNNEHNVAN

51 VDNNNGWDSWNSIWDYGNGFAATRLFQKKTCIVHKMNKEVMPSIQSLDAL

101 VKEKKLQGKGPGGPPPKGLMYSVNPNKVDDLSKFGKNIANMCRGIPTYMA

151 EEMQEASLFFYSGTCYTTSVLWIVDISFCGDTVEN

A

```
HUMAN  1 MKFTIVFAGLLGVFLAPALANYNIDVNDDNNNAGSGQQSVSVNNEHNVAN  50
         ||||  |||||||||  ||||.|.|  ||||  |. |||||||||||||||
PIG    1 MKFTIAFAGLLGVFLTPALADYSISVNDDGNSGGSGQQSVSVNNEHNVAN  50

51 VDNNNGWDSWNSIWDYGNGFAATRLFQKKTCIVHKMNKEVMPSIQSLDAL 100
         |||||||.||.:|||  |||  |||||:||.||||||  ||  |||:|.|||
      51 VDNNNGWNSWNALWDYRTGFAVTRLFEKKSCIVHKMKKEAMPSLQALDAL 100

101 VKEKKLQGKGPGGPPPKGLMYSVNPNKVDDLSKFGKNIANMCRGIPTYMA 150
         |||||||||||||||| | ||||||:||.| ||||.| ||:|||||||
     101 VKEKKLQGKGPGGPPPKSLRYSVNPNRVDNLDKFGKSIVAMCKGIPTYMA 150

151 EEMQEASLFFYSGTCYTTSVLWIVDISFCGDTVEN* 186
         ||.| |.| || |..:|||..||||| |||       *=termination
     151 EEIQGANLISYSEKCISANILWILNISFCGGIAEN* 186
```

B

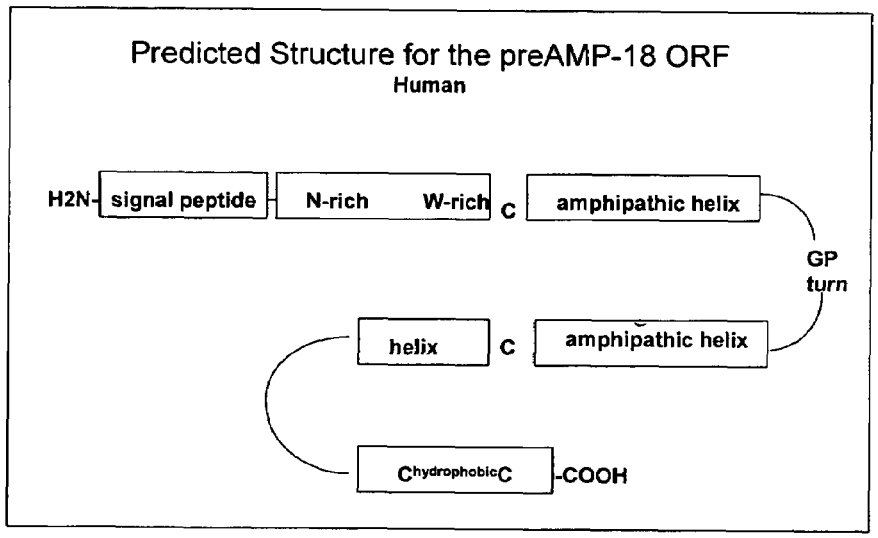

FIG. 14

CONTROL OF GROWTH AND REPAIR OF GASTRO-INTESTINAL TISSUES BY GASTROKINES AND INHIBITORS

This application is a continuation-in-part of U.S. Ser. No. 10/473,571, filed Jun. 22, 2004, which is a national phase of PCT/US02/09885, filed Mar. 29, 2002, which is a continuation-in-part of U.S. Ser. No. 09/821,726, filed on Mar. 29, 2001, which issued as U.S. Pat. No. 6,734,289, on May 11, 2004.

The U.S. government may have rights in this patent by means of partial support under National Institute of Health grant NIH:DK21901.

BACKGROUND

Searches for factors affecting the mammalian gastro-intestinal (GI) tract are motivated by need for diagnostic and therapeutic agents. A protein may remain part of the mucin layer, providing mechanical (e.g., lubricant or gel stabilizer) and chemical (e.g. against stomach acid, perhaps helping to maintain the mucus pH gradient and/or hydrophobic barrier) protection for the underlying tissues. The trefoil peptide family has been suggested to have such general cytoprotectant roles (see Sands and Podolsky, 1996). Alternatively, a cytokine-like activity could help restore damaged epithelia. A suggestion that the trefoil peptides may act in concert with other factors to maintain and repair the epithelium, further underlines the complexity of interactions that take place in the gastrointestinal tract (Podolsky, 1997). The maintenance of the integrity of the GI epithelium is essential to the continued well-being of a mammal, and wound closing after damage normally occurs very rapidly (Lacy, 1998), followed by proliferation and differentiation soon thereafter to reestablish epithelial integrity (Nursat et al., 1992). Thus protection and restitution are two critical features of the healthy gastrointestinal tract, and may be important in the relatively harsh extracellular environment of the stomach.

Searches for GI proteins have met with some success. Complementary DNA (cDNA) sequences to messenger RNAs (mRNA) isolated from human and porcine stomach cells were disclosed in the University of Chicago Ph.D. thesis "Characterization of a novel messenger RNA and immunochemical detection of its protein from porcine gastric mucosa," December 1987, by one of the present inventors working with the other inventors. However, there were several cDNA sequencing errors that led to significant amino acid changes from the AMP-18 protein disclosed therein. The protein itself was isolated and purified only as an aspect of the present disclosure, and functional analyses were performed to determine utility. Nucleic acid coding sequences were sought.

SUMMARY OF THE DISCLOSURE

A novel group of Gastric Antrum Mucosal Proteins that are gastrokines, is characterized. A member of the gastrokine group is designated AMP-18. AMP-18 genomic DNA, and cDNA molecules was sequenced for human and mouse, and the protein sequences are predicted from the nucleotide sequences. The cDNA molecule for pig AMP-18 was sequenced and confirmed by partial sequencing of the natural protein. The AMP-18 protein and active peptides derived from its sequence are cellular growth factors. Surprisingly, peptides capable of inhibiting the effects of the complete protein, were also derived from the AMP-18 protein sequence. Control of mammalian gastro-intestinal tissues growth and repair was facilitated by the use of the protein or peptides, making the protein and the derived peptides candidates for therapies.

The protein was discovered in cells of the stomach antrum mucosa by analysis of cDNA clones obtained from humans, pigs, and mice. The protein is a member of a group of cellular growth factors or cytokines, more specifically gastrokines. The AMP-18 cDNA sequences predict a protein 185 amino acids in length for both pig and man. The nucleotide sequences also predict a 20-amino acid N-terminal signal sequence for secreted proteins. The cleavage of this N-terminal peptide from the precursor (preAMP-18) was confirmed for the pig protein; this cleavage yields a secreted protein 165 amino acids in length and ca. 18,000 Daltons (18 kD) in size. Human and mouse genomic DNA sequences were also obtained and sequenced. A human genomic DNA was isolated in 4 overlapping fragments of sizes 1.6 kb, 3 kb, 3.3 kb and 1.1 kb respectively. The mouse genomic DNA sequence was isolated in a single BAC clone.

The gastrokine designated AMP-18 protein was expressed at high levels in cells of the gastric antrum. The protein was barely detectable in the rest of the stomach or duodenum, and was not found, or was found in low levels, in other body tissues tested. AMP-18 is synthesized in lumenal surface mucosal cells, and is secreted together with mucin granules.

Studies in humans confirm the location and expression of the AMP-18 peptide in human gastric mucosa.

Compositions of AMP-18 isolated from mouse and pig antrum tissue stimulate growth of confluent stomach, intestinal, and kidney epithelial cells in culture; human, monkey, dog and rat cells are also shown to respond. This mitogenic (growth stimulating) effect is inhibited by specific antisera (antibodies) to AMP-18, supporting the conclusion that AMP-18, or its products, e.g. peptides derived from the protein by isolation of segments of the protein or synthesis, is a growth factor. Indeed, certain synthetic peptides whose amino acid sequences represent a central region of the AMP-18 protein also have growth-factor activity. The peptides also speed wound repair in tissue culture assays, indicating a stimulatory effect on cell migration, the process which mediates restitution of stomach mucosal injury. Thus, the protein and its active peptides are motogens. Unexpectedly, peptides derived from sub-domains of the parent molecule can inhibit the mitogenic effect of bioactive synthetic peptides and of the intact, natural protein present in stomach extracts.

There are 3 activities of the gastrokine proteins and peptides of the present invention. The proteins are motogens because they stimulate cells to migrate. They are mitogens because they stimulate cell division. They function as cytoprotective agents because they maintain the integrity of the epithelium (as shown by the protection conferred on electrically resistant epithelial cell layers in tissue culture treated with damaging agents such as oxidants or non-steroidal anti-inflammatory drugs NSAIDs).

The synthesis of AMP-18 is confined to lumenal mucosal lining epithelial cells of the gastric antrum of humans and other mammals. Inside cells the protein is co-localized with mucins in secretion granules, and appears to be secreted into the mucus overlying the apical plasma membrane. Recombinant human AMP-18 in *E. coli* exerts its mitogenic effect at a concentration an order of magnitude lower than growth-promoting peptides derived from the center of the mature protein. Peptide 77-97 (SEQ ID NO: 12), the most potent of the mitogenic peptides, appears to be cell-type specific as it does not stimulate growth of fibroblasts or HeLa cells. Mitogenesis by specific AMP peptides appears to be mediated by a cell surface receptor because certain peptides that are not active mitogens can competitively inhibit, in a concentration-dependent manner, the growth-stimulating effects of peptide 58-99 and antrum cell extracts. AMP-18 and its derived peptides exhibit diverse effects on stomach and intestinal epithelial cells which suggest they could play a critical role in repair after gastric mucosal injury. These include cytoprotection, mitogenesis, restitution, and maturation of barrier function after oxidant- and/or indomethacin-mediated injury. Possible mechanisms by which AMP-18 or its peptide derivatives mediate their pleiotropic effects include stimulation of protein tyrosine kinase activity, prolongation of heat shock protein expression after cell stress, and enhanced accumulation of the tight junction-associated protein ZO-1 and occludin. Certain of these physiological effects can occur at concentrations that are relatively low for rhAMP-18 (<50 nM) compared to the concentrations of other gastric peptide mediators such as trefoil peptides or the α-defensin, cryptdin 3 (>100 µM). Immunoreactive AMP-18 is apparently released by cells of the mouse antrum after indomethacin gavage, and by canine antrum cells in primary culture exposed to forskolin, suggest that the protein is subject to regulation. These results imply that AMP-18 could play a role in physiological and pathological processes such as wound healing in the gastric mucosal epithelium in vivo.

A group of isolated homologous cellular growth stimulating proteins designated gastrokines, are produced by gastric epithelial cells and include the consensus amino acid sequences VKE(K/Q)KXXGKGPGG(P/A)PPK (SEQ ID NO: 10) wherein XX can be LQ or absent (which results in SEQ ID NOS 25 and 26, respectively). An isolated protein of the group has an amino acid sequence as shown in FIG. 7. The protein present in pig gastric epithelia in a processed form lacking the 20 amino acids which constitute a signal peptide sequence, has 165 amino acids and an estimated molecular weight of approximately 18 kD as measured by polyacrylamide gel electophoresis. Signal peptides are cleaved after passage through endoplasmic reticulum (ER). The protein is capable of being secreted. The amino acid sequence shown in FIG. 3 was deduced from a human cDNA sequence. An embodiment of the protein is shown with an amino acid sequence as in FIG. 6, a sequence predicted from mouse RNA and DNA.

A growth stimulating (bioactive) peptide may be derived from a protein of the gastrokine group. Bioactive peptides rather than proteins are preferred for use because they are smaller, consequently the cost of synthesizing them is lower than for an entire protein.

In addition, a modified peptide may be produced by the following method:
(a) eliminating major protease sites in an unmodified peptide amino acid sequence by amino acid substitution or deletion; and/or
(b) introducing into the modified amino acid analogs of amino acids in the unmodified peptide.

A synthetic growth stimulating peptide, has a sequence of amino acids from positions 78 to 119 as shown in FIG. 3.

Another peptide has a sequence of amino acids from position 97 to position 117 as shown in FIG. 3.

Another peptide has a sequence of amino acids from position 97 to position 121 as shown in FIG. 3.

Another peptide has a sequence of amino acids from position 104 to position 117 as shown in FIG. 3.

An embodiment of an isolated bioactive peptide has one of the following sequences: KKLQGKGPGGPPPK (SEQ ID NO: 11), LDALVKEKKLQGKGPGGPPPK (SEQ ID NO: 12), or LDALVKEKKLQGKGPGGPPPKGLMY (SEQ ID NO: 13). An embodiment of an inhibitor of a protein of the gastrokine group has the amino acid sequence KKTCIVHKMKK (SEQ ID NO: 14) or KKEVMPSIQSLDALVKEKK. (SEQ ID NO: 15) (see also Table 1)

A pharmaceutical composition includes at least one growth stimulating peptide.

A pharmaceutical composition for the treatment of diseases associated with overgrowth of gastric epithelia, includes an inhibitor of at least one protein of the group of gastrokines or of a growth stimulating peptide derived from the gastrokine proteins.

A pharmaceutical composition for the treatment of diseases of the colon and small intestine includes at least one growth stimulating peptide of the present invention. Examples of such diseases include ulcerative colitis and Crohn's Disease.

Antibodies to the protein product AMP-18 encoded by the human cDNA expressed in bacteria were produced in rabbits; these antibodies reacted with 18 kD antrum antigens of all mammalian species tested (human, pig, goat, sheep, rat and mouse), providing a useful method to detect gastrokines. An antibody to a protein of the group recognizes an epitope within a peptide of the protein that includes an amino acid sequence from position 78 to position 119 as in FIG. 3.

An isolated genomic DNA molecule has the nucleotide sequence of a human as shown in FIG. 1 and an isolated cDNA molecule encoding a human protein, has the nucleotide sequence as shown in FIG. 2.

An isolated DNA molecule has the genomic sequence found in DNA derived from a mouse, as shown in FIG. 4.

Genomic DNA has value because it includes regulatory elements for gastric expression of genes, consequently, the regulatory elements can be isolated and used to express other gene sequences than gastrokines in gastric tissue.

A mouse with a targeted deletion in a nucleotide sequence in the mouse genome that, when expressed without the deletion, encodes a protein of the group of gastrokines of the present invention.

A method of making a gastrokine protein or a peptide derived from a gastrokine protein includes:
a) obtaining an isolated cDNA molecule with a sequence such as that shown in FIG. 2;
(b) placing the molecule in a recombinant DNA expression vector;
(c) transfecting a host cell with the recombinant DNA expression vector;
(d) providing environmental conditions allowing the transfected host cell to produce a protein encoded by the cDNA molecule; and
(e) purifying the protein from the host cell.

Host cells in which expression has been successful include baculovirus, which allows large amounts of gastrokines to be provided for commercial and research uses. For example, human AMP-18 protein without the signal peptide was produced.

A recombinant human protein AMP-18 expressed in *E. coli* has the sequence in FIG. 14, (A).

A method to stimulate growth of epithelial cells in the gastrointestinal tract of mammals includes:
(a) contacting the epithelial cells with a composition comprising a gastrokine protein or a peptide derived from a protein of the group; and
(b) providing environmental conditions for stimulating growth of the epithelial cells.

A method to inhibit cellular growth stimulating activity of a protein of the group includes:
(a) contacting the protein with an inhibitor; and
(b) providing environmental conditions suitable for cellular growth stimulating activity of the protein.

The inhibitor may be an antibody directed toward at least one epitope of the protein, e.g. an epitope with an amino acid sequence from position 78 to position 119 of the deduced amino acid sequence in FIG. 3 or an inhibitor peptide such as those in Table 1.

A method of testing the effects of different levels of expression of a protein on mammalian gastrointestinal tract epithelia, includes the steps of:
(a) obtaining a mouse with an inactive or absent gastrokine protein;
(b) determining the effects of a lack of the protein in the mouse;
(c) administering increasing levels of the protein to the mouse; and
(d) correlating changes in the gastrointestinal tract epithelia with the levels of the protein in the epithelia.

Kits are contemplated that will use antibodies to gastrokines to measure their levels by quantitative immunology. Levels may be correlated with disease states and treatment effects.

A method to stimulate migration of epithelial cells after injury to the gastrointestinal tract of mammals, includes:
(a) contacting the epithelial cells with a composition comprising a peptide derived from the protein; and
(b) providing environmental conditions allowing migration of the epithelial cells.

A method for cytoprotection of damaged epithelial cells in the gastrointestinal tract of mammals, includes:
(a) contacting the damaged epithelial cells with a composition including a protein of the gastrokine group or a peptide derived from the protein; and
(b) providing environmental conditions allowing repair of the epithelial cells.

The damaged cells may form an ulcer.

BRIEF DESCRIPTION OF THE DRAWINGS

FIG. 1 is a human genomic nucleotide sequence (SEQ ID NO: 1) of a pre-gastrokine; sequence features were determined from cDNA and PCR of human genomic DNA amphge8.seq. Length: 7995 predicted promoter: 1405; exon 1: 1436-1490; exon 2: 4292-4345; exon 3: 4434-4571; exon 4: 5668-5778; exon 5: 6709-6856; exon 6: 7525-7770; polyA site: 7751 (amph refers to antrum mucasal protein human genomic nucleotide sequence.

FIG. 2 is a human cDNA sequence (SEQ ID NO: 2); the DNA clone was obtained by differential expression cloning from human gastric cDNA libraries.

FIG. 3 is a human preAMP-18 protein sequence (SEQ ID NO: 3) predicted from a cDNA clone based on Powell (1987) and revised by the present inventors; N-21 is the expected N-terminus of the mature protein.

FIG. 4 is a mouse preAMP-18 sequence (SEQ ID NO: 4) determined from RT-PCR of mRNA and PCR of BAC-clones of mouse genomic DNA sequences:
predicted promoter: 1874 experimental transcription start site: 1906 translation initiation site: 1945 CDS 1: 1906-1956; CDS 2: 3532-3582; CDS 3: 3673-3813; CDS 4: 4595-4705; CDS 5: 5608-5749; CDS 6: 6445-6542; polyA site: 6636.

FIG. 5 is a mouse cDNA sequence (SEQ ID NO: 5) for preAMP-18.

FIG. 6 is mouse preAMP-18 amino acid sequence (SEQ ID NO: 6); RT-PCR performed on RNA isolated from mouse stomach antrum: Y-21 is the predicted N-terminus of the mature protein; the spaces indicated by . . . mean there are no nucleotides there to align with other sequences in FIG. 11.

FIG. 7 is a cDNA expressing porcine AMP-18 (SEQ ID NO: 7).

FIG. 8 is pig pre-gastrokine (pre-AMP-18) protein sequence (SEQ ID NO: 8) predicted from a cDNA clone based on Powell (1987) D-21 is the N-terminus of the mature protein—confirmed by sequencing of the protein isolated from pig stomach.

FIG. 9 is a comparison between the amino acid sequences of human (SEQ ID NO: 3) versus pig (SEQ ID NO: 8) pregastrokine.

FIG. 10 shows a computer-generated alignment comparison of human (SEQ ID NO: 3), pig (SEQ ID NO: 8) and mouse (SEQ ID NO: 6) predicted protein sequences determined from sequencing of cDNA clones for human and pig AMP-18, and by polymerase chain reaction of mouse RNA and DNA using preAMP-18 specific oligonucleotide primers; in each case the first 20 amino acids constitute the signal peptide, cleaved after passage through the endoplasmic reticulum membrane.

FIG. 14 shows (A). Alignment of the open reading frames (ORF) derived from the cDNA clones for AMP-18 for the precursor proteins of human (SEQ ID NO: 3) and pig (SEQ ID NO: 8) antrum. Similarity was 78.50% and identity was 75.27%. Computer analysis was carried out using the GAP and PEPTIDESTRUCTRE programs of the Wisconsin Package (GCG). (B). Model of the predicted secondary structure for the human preAMP ORF. Attention is drawn to the asparagine rich N-terminal domain, the short tryptohopan (W)-rich and glycine-proline (GP) regions, and the conserved positions of the four cysteine (C) residues. Possible amphipathic helices are indicated.

DETAILED DESCRIPTION OF THE DISCLOSURE

Summary

Figure 46:
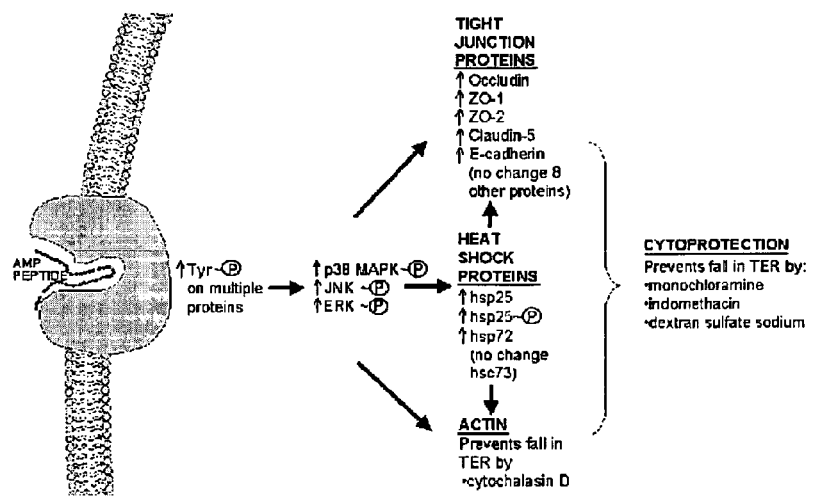
FIG. 46. Steps in AMP peptide-mediated cytoprotection of intestinal epithelial cells. When AMP peptide binds to its putative cell surface receptor it stimulates tyrosine phosphorylation of multiple proteins. This is followed by phosphorylation of 3 classes of signaling molecules (p38 MAPK, JNK1/2, ERK1/2), increased accumulation of TJ (occludin, ZO-1, ZO-2, claudin-5), AJ (E-cadherin), and heat shock (hsp25, hsp72) proteins, and functional stabilization of actin. These cellular responses may contribute to AMP peptide's cytoprotective effect when the intestinal epithelium is subjected to barrier-disrupting agents.

The results disclosed herein characterize the structure and function of AMP-18 using both a recombinant human protein prepared in *E. coli* and a synthetic peptide that are both bioactive. The pleiotropic effects of AMP peptide 77-97 in epithelial cell cultures include maturation, protection and repair of barrier function, as well as stimulation of restitution and cell proliferation, all of which relate to protective and reparative roles in GI mucosal injury. The cytoprotective effect of AMP peptide appears to be mediated, at least in part, by its capacity to increase accumulation of TJ occludin, and other tight and adherens junction proteins (ZO-1, ZO-2, claudin-5, E-cadherin, JAM), as well as hsp25 and hsp72, and to stabilize the perijunctional actin filament network after injury (FIG. 46). AMP peptide apparently exerts its effects via a receptor-mediated mechanism to activate protein tyrosine phosphorylation, and stimulate phosphorylation of p38 MAPK, hsp25, PKCζ, ERK, and JNK. When given to mice, AMP peptide delayed the onset of bloody diarrhea and protected against weight loss in DSS colitis, and prevented death in gut-derived sepsis. These observations show that the cytoprotective effect of AMP peptide on colonic epithelial cells in culture and in vivo is mediated by the capacity of the peptide to enhance accumulation of specific tight and adherens junction proteins and hsps, and stabilize actin which could thereby protect and defend the structure and function of the mucosal barrier in IBD, mucositis, gut-derived sepsis, gastritis, gastric ulcer disease, and the consequences of gastric antrum infection by *H. pylori*.

Therapeutic Efficacy

The data disclosed herein points to multiple therapeutic targets for AMP-18/AMP peptide. These include treatment of IBD by: (a) preventing or decreasing the frequency and intensity of acute exacerbations of this episodic disease by the AMP peptide's cytoprotective effect, and (b) speeding recovery of the colonic mucosal epithelium after an attack of disease occurs, i.e., a benefit inferred from the mitogenic and motogenic (wound healing) effects observed in cell culture and murine models of colitis. The cytoprotective, mitogenic and motogenic effects of AMP peptide also predict a therapeutic role in cancer-therapy induced mucositis of the GI tract as often occurs during chemotherapy and/or radiation therapy. Mucositis occurs in this setting because the therapeutic protocol is designed to destroy proliferating cancer cells, but may also damage rapidly growing cells that line the mouth, throat, or GI mucosa at any point along its entire length. Injury and/or destruction of the protective mucosal epithelium can result in life-threatening infection which puts the patient at risk for gut-derived sepsis and death. Evidence is also provided support therapeutic benefits of AMP peptide in the treatment of gut-derived sepsis (cytoprotection), gastritis and gastric ulcers (cytoprotection, mitogenesis, restitution), and infection with *H. pylori* (growth inhibition of the organism). The mitogenic and cytoprotective effects of AMP peptide on renal epithelial cells (MDCK line) in culture disclosed herein also predict therapeutic role for the peptide in patients with acute renal failure.

In summary the cytoprotective, mitogenic, and motogenic effects of AMP peptide and rhAMP-18 offer multiple therapeutic strategies to prevent and/or limit disruption of epithelial barrier function and structure, and also speed regeneration after mucosal injury in gut and kidney.

Other aspects of the disclosure follow.

1. General

A novel gene product, a member of a group of gastrokines, was detected in mammalian gastric antrum mucosal by a differential screen of cDNA libraries obtained from different regions of the pig stomach. The cDNA sequence predicted a protein of 185 amino acids including a signal peptide leader sequence. A cDNA was also isolated from a human library. The predicted amino acid sequence identity between pig and human in 76.3%. The sequences predicted a 20 amino acid signal peptide characteristic for secreted proteins. The cleavage of this N-terminal signal peptide was confirmed for the pig protein. Antibodies to the product of the human cDNA expressed in bacteria were raised in rabbits; these antibodies reacted with 18-20 kD antrum antigens of all mammalian species tested (pig, goat, sheep, rat and mouse). In agreement with mRNA levels, the AMP-18 protein is expressed at high levels only in the gastric antrum; it is barely detectable in the rest of the stomach or duodenum, and was not detected in a variety of other tissues tested. AMP-18 is synthesized in the lumenal surface mucosal cells; immuno-electron microscopy locates AMP-18 in the secretion granules of these cells. Partially purified AMP-18 preparations from mouse and pig antrum tissue are mitogenic to confluent stomach and kidney epithelial cells in culture; this effect is inhibited by the specific antisera, implying that AMP-18, or its products, is a growth factor.

AMP-18 is likely secreted with the mucus and functions, perhaps as peptide derivatives within the mucus gel to maintain epithelial integrity directly, and possibly to act against pathogens. In view of the growth factor activity observed on epithelial cell lines in culture, it is likely that AMP-18 or its peptide derivative(s) serves as an autocrine (and possible paracrine) factor for the gastric epithelium. The function of AMP-18 may not be simply as a mitogen, but in addition it may act as differentiation factor providing the signals for replenishment of the mature lumenal surface cells. The AMP-18 protein or its derivatives are likely important to the normal maintenance of the highly dynamic gastric mucosa, as well as playing a critical role in the restitution of the antrum epithelium following damage. Limitations of EST data cannot yield information on starting sequences, signal peptides, or sequences in the protein responsible for bioactivity, as disclosed in the present invention. A number of these ESTs have been reported for mammalian stomach cDNAs, but related ESTs have also been reported or pancreas and also pregnant uterus libraries. Although expression of AMP-18 RNA in these other tissues appears to be low (as indicated for pancreas by PCR analysis), these results suggest that this growth factor may have broader developmental and physiological roles than that implied by the specific high levels of expression found for the stomach.

The AMP-18 protein appears to be expressed at the surface of the cellular layers of the gastrointestinal (GI) tract. The expressing cells may be releasing stored growth factor where needed—in the crypts and crevices of the GI tract where cellular repair is needed due to surface damage.

AMP-18 may act on the mucosal, apical surfaces of the epithelial cells, collaborating with prostaglandins and other growth factors that operate via basolateral cell surface receptors on the serosal side. The protein or its derivatives are likely important for the normal maintenance of the highly dynamic gastric mucosa, in face of the mechanical stress and high acidity of the stomach. AMP-18 may play a critical role in the repair of the stomach epithelium following damage by agents such as alcohol, nonsteroidal anti-inflammatory drugs (NSAIDs), or pathogens, in particular *Heliobacter pylori*, which predominantly infects the antrum and is a causative agent of gastric ulcers and possibly cancers.

2. Bioactivity

A synthetic peptide (42 amino acids, a "42-mer") representing a central region of the AMP-18 amino acid sequence also has growth factor activity, which is inhibited by specific antisera; some related shorter peptides also have stimulatory activity, while others can inhibit the activity of the 42-mer. These findings suggest that a saturable epithelial receptor exists for AMP-18, and opens direct avenues to analyzing the bioactive regions of the protein and identifying the putative receptor(s). Because AMP-18 does not resemble in structure any known cytokine or cytoprotectant protein (such as the trefoil peptides), the analysis of the interactions of the protein, and its active and inhibitory related peptides, with cells offers the opportunity to reveal novel molecular interactions involved in cell growth control.

BSC-1 cell growth was stimulated by gel-fractionated porcine antrum extract; porcine extract protein (250 µg) was loaded into each of 2 lanes and subjected to electrophoresis in a polyacrylamide gel (12.5%); the 5 thin slices (2-3 mm) from each area between $M_r$ 14 kDa and 21.5 kDa were cut from the experimental lanes. Each pair of slices was placed in a silanized microfuge tube with 200 µl sterile PBS, 3% acetonitrule and 1% BSA, and macerated; proteins were eluted from the gel for 18 hr at 22° C. with vigorous shaking; the samples were then microcentrifuged and a sample of a supernatant was added to a confluent culture of BSC-1 cells; the number of cells was counted 4 days later; maximal growth stimulation was observed in cultures receiving extracts eluted from gel slices corresponding to a $M_r$ of ~18 kDa; antisera to recombinant human AMP-18 added to the culture medium completely inhibited growth stimulation by the 18 kDa fraction (+Ab); values are means of 2 cultures; SE is less than 10% of the mean.

The biological activity (mitogenic for epithelial cells in the gastro-intestinal tract) of the AMP-18 is located in the C-terminal half of the protein. The epitopic sequence(s) appear(s) to be immediately N-terminal to the mitogenic sequence.

The biological activity that is a growth factor, is exhibited by a peptide that includes at least 42 amino acids from positions 78 to 119 of the full-length protein sequence. An antibody to this region blocked mitogenic activity. Although a peptide having an amino acid sequence of 104 to 117 had mitogenic activity, an antibody to this region did not block (inhibit) the activity. A peptide with an amino acid sequence from positions 97-117 has the same mitogenic activity as a peptide with the 42 amino acid sequence, but is less expensive to produce as a synthetic peptide.

3. Inhibition of Bioactivity

Epithelial cell growth that was stimulated by murine or porcine antrum cell extract was blocked by rabbit antiserum to a complete, recombinant human AMP-18 precursor protein; confluent cultures of BSC-1 cells were prepared; murine or porcine antrum cell extract was prepared and its protein concentration was measured; cell extracts alone and with different dilutions of the antiserum, or antiserum alone (1:100 dilution was added to the culture medium, and the number of cells was counted 4 days later). Growth stimulation by murine antrum gastrokines was maximally inhibited by the antiserum (93%) at a dilution of 1:400, whereas stimulation by the porcine antrum protein extract was totally inhibited at a dilution of 1:100. Scored values were means for 3 cultures; standard error of the mean (SE) was less than 10% of the mean.

Antibodies to the AMP-18 protein have diagnostic uses to determine different levels of the protein in the gastro-intestinal tract in vivo. Ulcers are likely to develop if less than normal levels of AMP-18 protein are present. Normal values are determined by technologies known to those of skill in the art, that is, obtaining representative samples of persons to be tested (age, sex, clinical condition categories) and applying standard techniques of protein quantitation. The effects of aspirin and indamethacin on AMP-18 levels are also useful to monitor deleterious levels of the drugs including the non-steroidal anti-inflammatory drugs (NSAIDs). Stomach cancer cell lines do not express the AMP-18 proteins at least by detection methods disclosed herein.

4. Genomic DNA

Genomic AMP-18 DNA sequences have been cloned for human and mouse as a prelude to the analysis of the gene regulatory elements, which presumably determine the great differences in the levels of expression of the gene in tissues where the gene may be active. Upstream and downstream flanking sequences have been isolated from mouse genomic DNA preparatory to a gene knockout. The flanking genomic sequences likely determine the very different levels of expression of the gene in the stomach and few other tissues where it may be expressed. With the involvement of different regulatory elements, gastrokine genes could be expressed as a growth factor in other tissues.

5. Uses of Gastrokines of the Present Disclosure

Because the AMP-18 protein and certain peptides derived from it can stimulate growth and wound repair by stomach and intestinal epithelial cells (as well as kidney) these gastrokine molecules are candidates for therapeutic agents to speed recovery of the injured GI tract following pharmacological interventions, radiotherapy, or surgery. In addition, the antibodies developed to gastrokines may be used in kits to measure the levels of AMP-18 protein or peptide in tissue of blood in diverse pathological states. These novel molecules have great therapeutic potential in the treatment of gastric ulcers, and inflammatory bowel disease, whereas new agents that inhibit its function could prove useful in the treatment of cancers of the GI tract.

The stomach is not a congenial location for many bacteria, and those that can survive the acidity do not establish themselves there (Rotimi et al., 1990). It is of interest therefore that the antrum region is the favored site for the attachment, penetration and cytolytic effects of *Helicobaccter pylori*, an agent which infects a major proportion of the human population (>60% by the seventh decade) and has been associated with gastritis, gastric and duodenal ulcers (Goodwin et al., 1986; Blaser, 1987) and gastric adenocarcinomas (Nomura et al., 1991; Parsonnet et al., 1991). Thus as an epithelial cell growth factor, AMP-18 may act to ameliorate the damage caused by bacterial infiltration and cytolysis. Given the conjunction of the specific antrum expression of AMP-18 and the preferred site of binding of *H. pylori*, it is possible that the bacteria use AMP-18 as a tropic factor. *H. pylori* attaches to cells of the antrum having fucose-containing mucin granules (Falk et al., 1993; Baczako et al., 1995). These granules also may contain AMP-18. Anti-microbial peptides have been found in the stomach of the amphibian *Xenopus laevis* (Moore et al., 1991). Some domains of the AMP-18 structure resemble that of the magainins, and possibly AMP-18 interacts with enteric bacteria.

6. AMP Peptide 77-97 Inhibits Growth of Human *Helicobacter pylori*.

Figure 28:
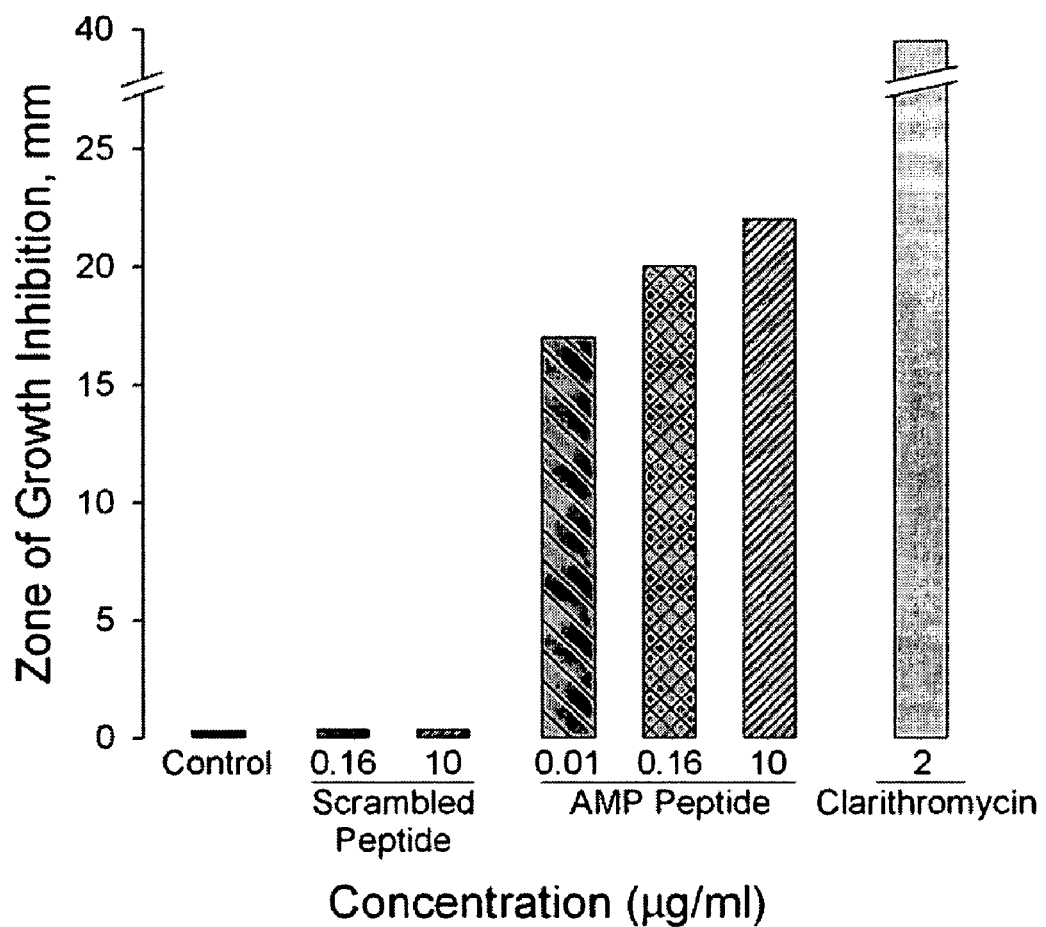
FIG. 28 shows that AMP peptide 77-97 inhibits growth of human *Helicobacter pylori*. When a lawn of *H. pylori* was prepared on a culture dish, growth of the organisms was inhibited by the antibiotic clarithromycin (positive control) and at 3 concentrations of AMP peptide 77-97, but not by scrambled AMP peptide.

To determine if AMP peptide inhibits growth of *H. pylori*, a lawn of bacteria was prepared on a culture dish. A small circular filter was placed in the center of the dish, a solution of a test agent was placed on the filter so it diffused onto the lawn, and its effect on bacterial growth around the filter was measured. AMP peptide 77-97 (SEQ ID NO: 12) (Table 1), a scrambled version of this AMP peptide (negative control) (SEQ ID NO: 19), or the antibiotic clarithromycin (positive control) was added to a filter on different cultures. As shown in FIG. 28, the vehicle (control) and the scrambled peptide (negative control) did not inhibit growth of *H. pylori*, whereas clarithromycin, an agent used clinically to treat *H. pylori* infection in humans, and AMP peptide both inhibited growth of the organism. The growth-inhibitory effect of AMP peptide appeared to be relatively specific for *H. pylori* because the peptide did not alter the growth of the following bacteria and fungi: *Staphylococcus aureus, Staphylococcus epidermidis, Enterococcus faecalis, Streptococcus pneumoniae, Streptococcus agalactiae, Escherichia coli, Pseudomonas aeruginosa, Klebsiella pneumoniae, Acinetobacter baumanii, Aspergillus niger,* or *Candida albicans*. These findings suggest that when *H. pylori* organisms bind to the mucosal epithelial surface of the gastric antrum, its cells could respond defensively by producing and/or secreting full-length AMP-18 form, or a peptide fragment of it that can act as an antibiotic. In addition, AMP peptide could serve as a therapeutic agent to treat *H. pylori* infections in the stomach, and thereby prevent the capacity of this organism to cause gastritis, gastric ulcers, and gastric adenocarcinomas.

7. Isolation of Pig AMP-18

Antisera against human AMP-18 protein were used to assist in the purification of the protein from extracts of pig antrum mucosa. Immnoaffinity methods applied to total tissue extracts have not proven very effective, but by using immunoblots to monitor cell-fractionation, gradient centrifugation and gel electrophoresis, sufficient amounts of the pig 18 kDa polypeptide were purified to confirm by sequencing that the native N-terminus is the one predicted by cleavage of 20 amino acids from the N-terminus of the ORF precisely at the alanine-aspartate site anticipated for signal peptide removal. Despite the abundance of asparagine residues in the mature protein, none fit the consensus context characteristic of glycosylation. Fairly extensive regions of the protein may possess amphipathic helix forming propensity. The latter may represent units within the protein yielding bioactive peptides after processing. Using circular dichroism the synthetic peptide representing amino acids 126-143 in the human preAMP sequence (FIG. 3) is readily induced to become helical in moderate concentrations of trifluoroethanol conditions used to assess helix propensity for some bioactive peptides, including anti-microbial peptides of the magainin type (see, for example, Park et al., 1997).

8. Preparation of Active Recombinant Human AMP-18 in *E. coli*

Figure 13:
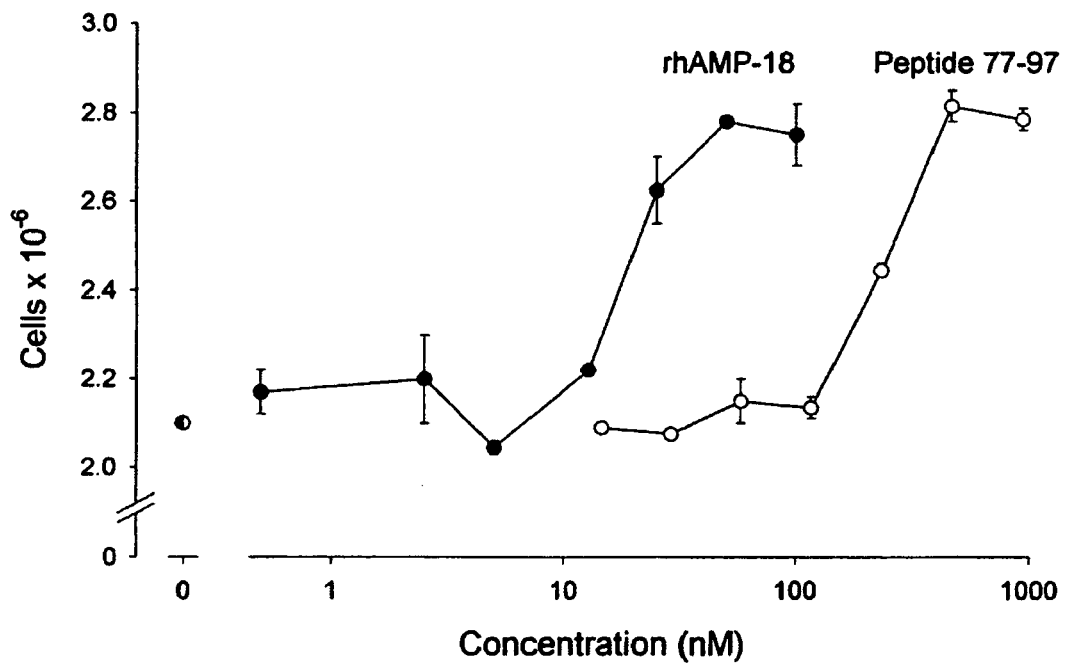
FIG. 13 shows (A). Amino acid sequence of recombinant human AMP-18 (residues 21-185 of SEQ ID NO: 3) expressed in *E. coli*. Note the His6-tag (SEQ ID NO: 16) within a 12 amino acid domain (SEQ ID NO: 9) at the N-terminus that has replaced the putative hydrophobic signal peptide. The sequence of the fusion product is shown in SEQ ID NO: 27. (B). Effect of rhAMP-18 and AMP peptide 77-97 on growth of confluent cultures of IEC-18 cells. Although maximal growth stimulation is similar, the half-maximal concentration ($K_{1/2}$) for rhAMP-18 (~30 nM) is about an order of magnitude lower than for the peptide (~300 nM).

A cDNA encoding human AMP-18 was designed in which the 20-amino acid hydrophobic signal peptide sequence was replaced with an N-terminal 12-amino acid peptide that included a starch of 6 histidine residues (FIG. 13, (A)). Expression of this modified cDNA sequence was predicted to yield a 177-amino acid protein product ($M_r$ 19, 653) that could be readily purified using Ni-NTA resin to bind the His6-tag (SEQ ID NO: 16). The cDNA sequence lacking the region coding for the N-terminal signal peptide (see FIG. 14) was amplified by PCR using oligonucleotides that provided suitable linkers for inserting the product into the BamH1 site of a QE3O expression vector (QIAGEN); the sequence of the recombinant vector was confirmed. The recombinant human (rh) AMP-18 engineered with the His6-tag (SEQ ID NO: 16) was subsequently expressed in *E. coli* cells. To harvest it, the bacteria were lysed and aliquots of the soluble and insoluble fractions were subjected to SDS-PAGE followed by immunoblotting using the specific rabbit antiserum to the rhAMP-18 precursor. Very little of the expressed protein was detected in the soluble fraction of the lysate.

Urea (6 M) was employed to release proteins from the insoluble fraction solubilize rhAMP-18 containing the His6-tag (SEQ ID NO: 16), and make it available to bind to the $Ni^{2+}$-charged resin from which it was subsequently eluted with a gradient of imidazole (0 to 200 mM). The amount of eluted rhAMP-18 was measured using the BCA assay, and the appearance of a single band at the predicted size of 19-20 kD was confirmed by SDS-PAGE followed by immunoblotting. To determine if eluted rhAMP-18 renatured to assume a structure that was mitogenic, aliquots of the eluate (following removal of urea and imidazole by dialysis) were added to cultures of IEC-18 cells and the number of cells was counted 4 days later. FIG. 13 (right panel) indicates that the recombinant protein stimulates cell proliferation to the same maximal extent as does mitogenic AMP peptide 77-97 (or soluble antrum tissue extracts from pig shown in FIG. 11), but that it does so at a half-maximal concentration an order of magnitude lower than for peptide 77-97. AMP peptide 77-97 refers to the mature protein; same as peptide 97-117 of human precursor protein: Table 1. These observations indicate that biologically active recombinant human AMP-18 that can be utilized in diverse clinical situations is available. The mitogenic potency of rhAMP-18 is in the nanomolar range which would be expected for a native gastric cell growth factor that participates in the maintenance and repair of the stomach in vivo.

The demonstration that amino acids 77-97 represent a functional domain of AMP-18 suggest that the full-length protein could easily be modified at its N- and/or C-terminus. Targeted modifications could prolong the half-life of AMP-18 in the circulation and tissues in vivo, thereby enhancing its pharmacokinetic profile without adversely affecting its diverse biological functions.

9. Stimulation of Growth and Restitution of Stomach and Intestinal Epithelial Cells by AMP-18 and Derived Peptides To characterize the capacity of gastric and intestinal cells to respond to AMP-18, AGS gastric adenocarcinoma cells, HAE human gastric antrum mucosa primary cultures transformed with SV40 large T antigen, rat diploid small intestinal epithelial cells of the IEC-6 (FIG. 15) and IEC-18 lines, NCI N-87 gastric carcinoma cells, and SK-GT5 gastroesophageal adenocarcinoma cells were studied; human WI-38 fibroblasts and HeLa cells served as non-GI control cell lines. Mitogenesis was assayed by performing cell counts 3 to 4 days after exposing cells to the agent of interest, trypsinizing the culture to prepare single cells, and confirming this while counting them in a hemocytometer.

Figure 11:
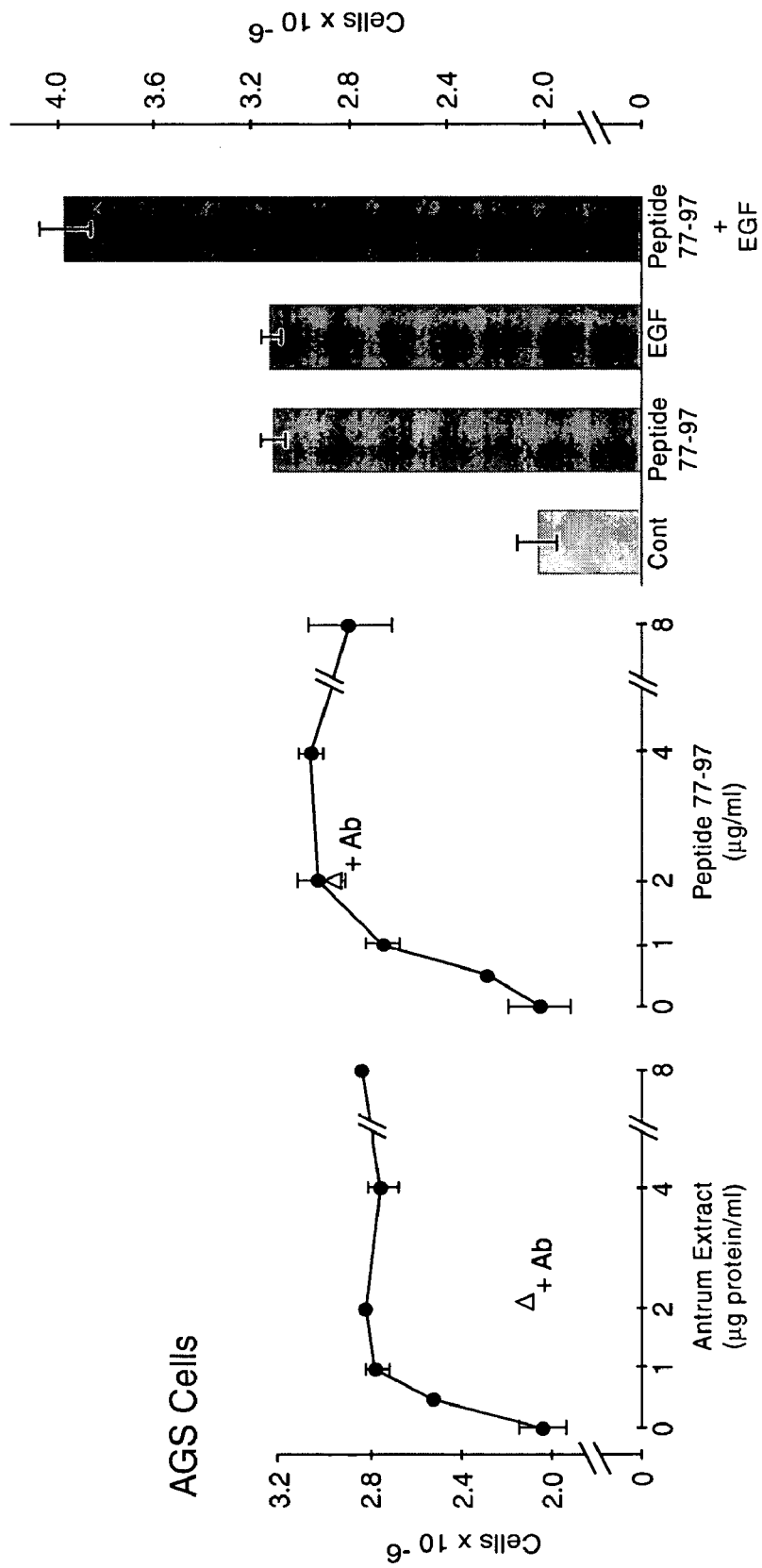
FIG. 11 shows the effect of porcine gastric antrum mucosal extract, human AMP peptide 77-97, of the mature protein (same as peptide 97-117 of the human precursor protein: Table 1) and EGF on growth of gastric epithelial cells; AGS cells were grown in DMEM containing fetal bovine serum (5%) in 60-mm dishes; different amounts of pig antrum extract, HPLC purified peptide 77-97, and/or EGF were added; four days later the cells were dispersed and counted with a hemocytometer; antrum extract and peptides each stimulated cell growth in a concentration-dependent manner; the bar graph shows that at saturating doses, peptide 77-97 (8 μg/ml) or EGF (50 ng/ml) was mitogenic; together they were additive suggesting that the two mitogens act using different receptors and/or signaling pathways; anti-AMP antibodies inhibited the antrum extract but did not inhibit peptide 77-97.
Figure 12:
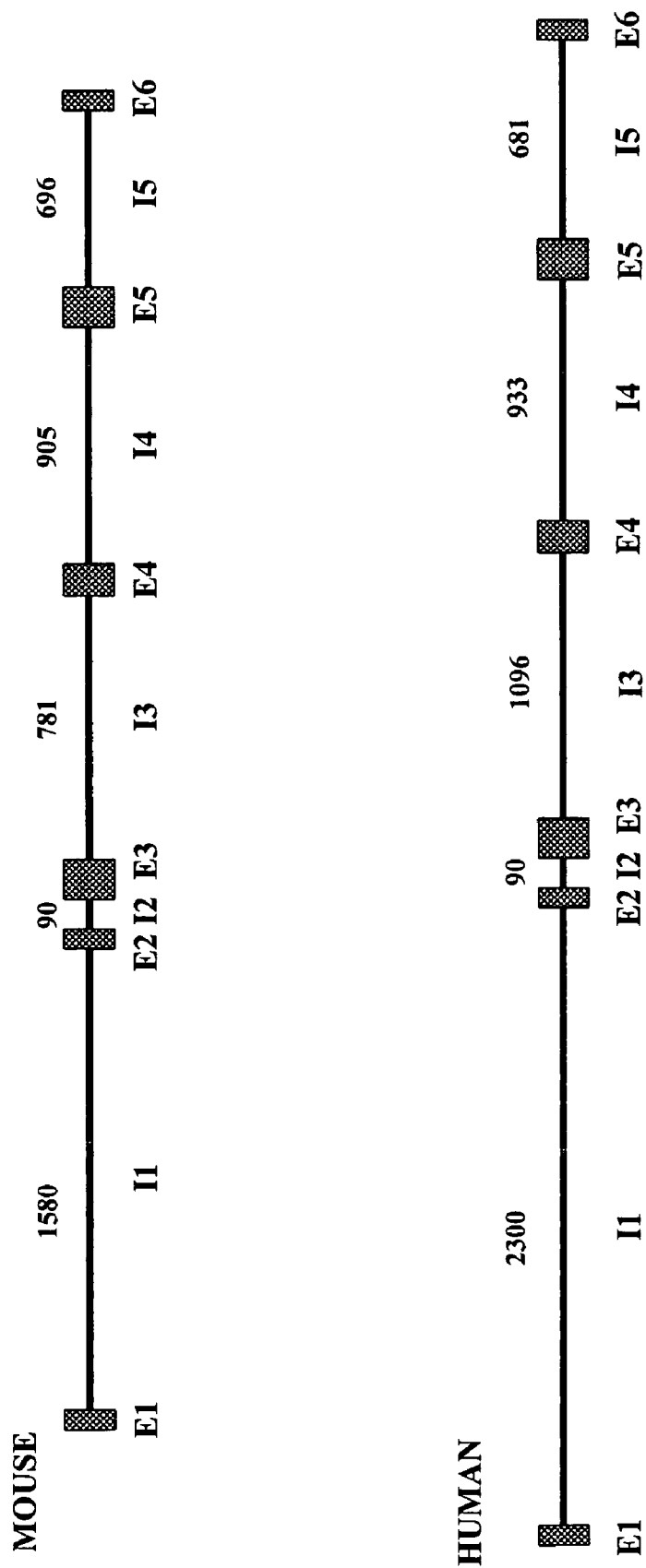
FIG. 12 shows the structure of the human and mouse preAMP-18 genes; the number of base pairs in introns are shown above the bars; exons are indicated E1-E6 and introns I1-I5; there are minor differences in intron length.
Figure 15:
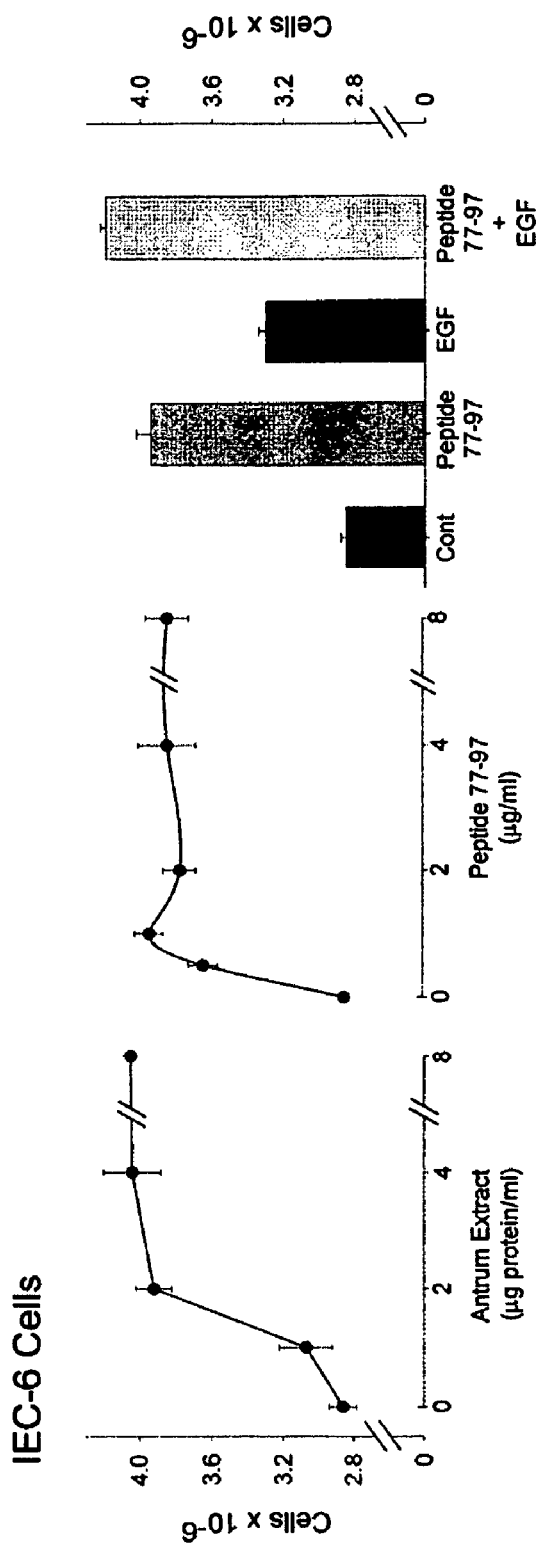
FIG. 15 shows the effect of porcine antrum cell extract, peptide 77-97, and EGF on growth of intestinal epithelial cells. IEC-6 cells were grown in 60-mm dishes. Antrum cell extract (left panel) and peptide 77-97 (center panel) each stimulated growth in a concentration-dependent manner. Peptide 77-97 (1 µg/ml) appeared more potent than EGF (50 ng/ml) (right panel). Values are means±SE for 3 cultures.
Figure 16:
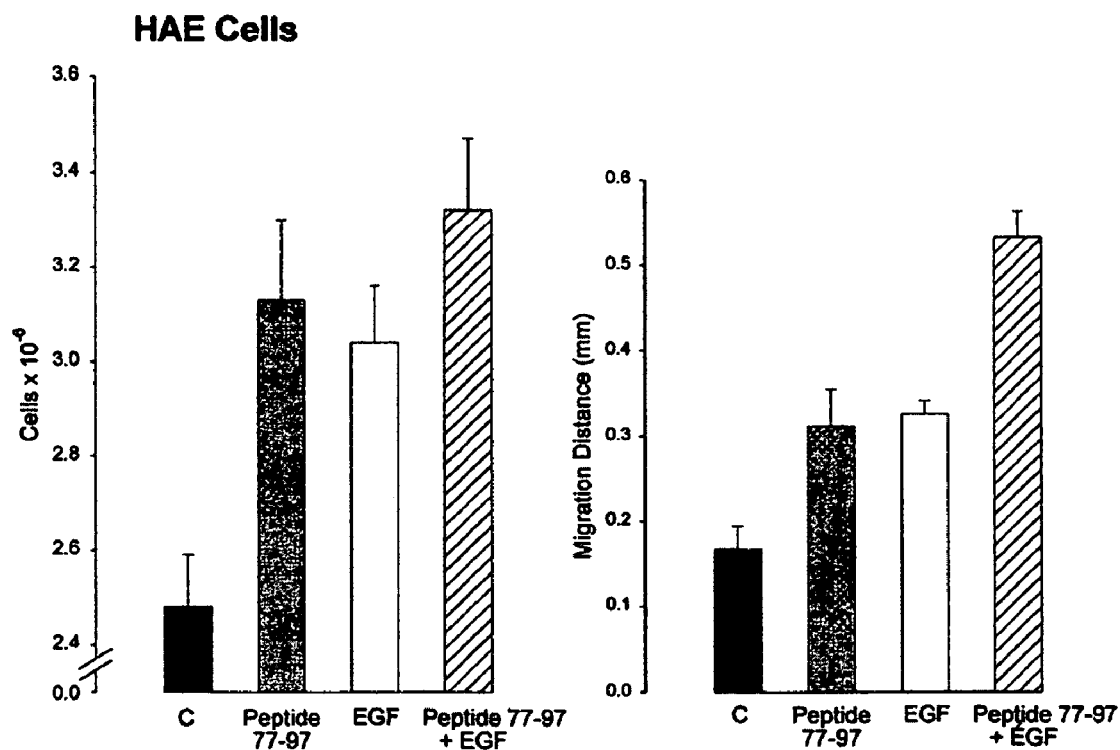
FIG. 16 shows the effect of AMP peptide 77-99 and EGF on growth and wound restitution by human antrum epithelial cells. To measure growth (left panel), HAE cells were plated in 60-mm dishes. Peptide 77-97 (8 µg/ml), or EGF (50 ng/ml), or both were added to the medium and the number of cells counted 4 days later. Peptide 77-97 and EGF each stimulated proliferation, and appeared to be additive. Values are means±SE for 3 cultures. To measure migration (right panel), cells were grown in 60-mm dishes to prepare a confluent monolayer. The medium was aspirated and replaced with fresh medium containing 0.01% calf serum (CS). The monolayer was mechanically wounded by scraping with a razor blade. Detached cells were removed by aspirating medium, and rinsing the remaining cells twice with fresh medium containing 0.01% CS. Fresh medium (5 ml) containing CS (0.01%) and insulin (100 U/L) was added to wounded cultures. Either peptide 77-97 (8 µg/ml), EGF (50 ng/ml), or both were added to duplicate cultures. Migration was assessed at 24, 48 and 72 hr after wounding by measuring the distance (in mm) that cells had migrated from the wound edge using a microscope eyepiece reticle (10-mm long; 0.1-mm markings). Migrating cells at 12 randomly chosen sites along a 0.25-mm stretch of the wound edge were measured at 40-fold magnification. Migration at 2 different sites was measured for each of 2 separate wounds made in each culture. Values are the mean distance cells moved into the denuded area from the edge of 4 different wounds in 2 cultures±SE. Cells exposed to peptide 77-97 migrated further from the wound edge than those exposed to vehicle at 72 hr. EGF also stimulated cell movement, and the two agents acting together markedly enhanced migration.
Figure 18:
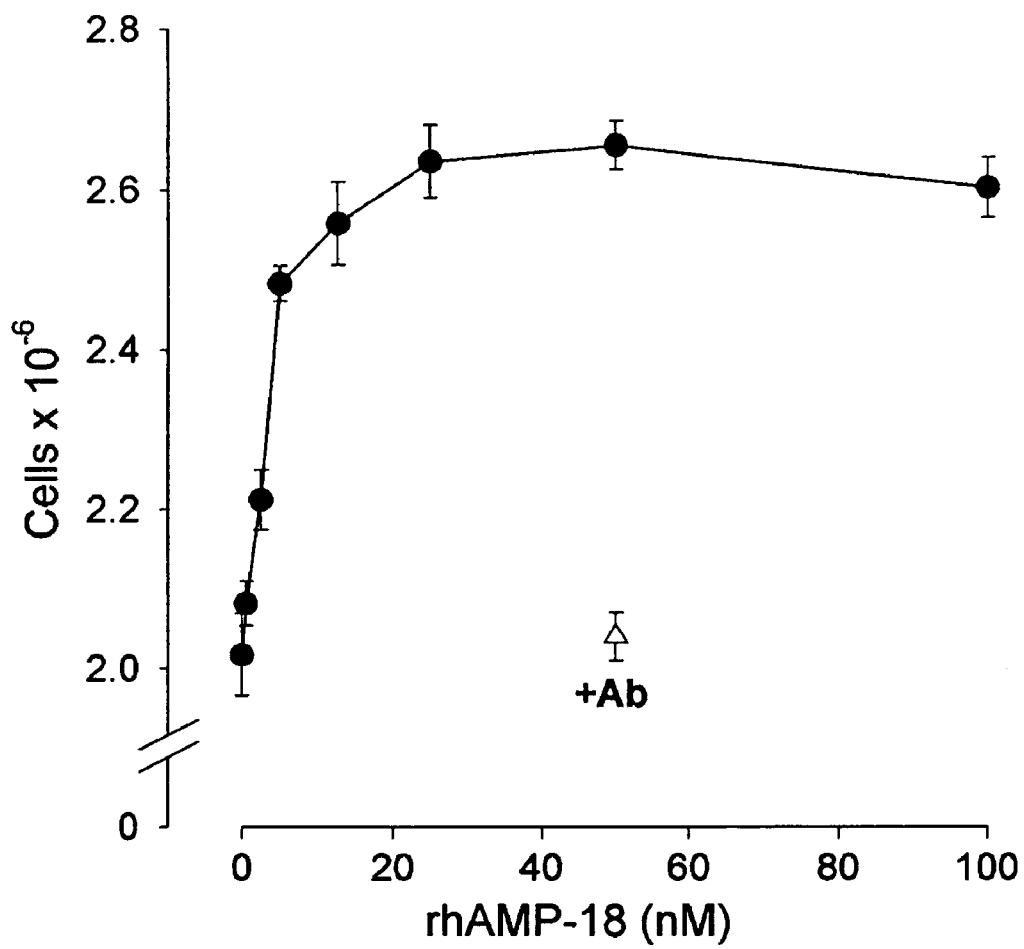
FIG. 18 shows the effect of rabbit antiserum to AMP-18 on mitogenic effect of rhAMP-18 on confluent IEC-18 cells. When rhAMP-18 (50 nanomolar) was preincubated for 30 min with antiserum (1:100 dilution)+Ab), growth stimulation was reduced by ~95%; preimmune serum had no effect on cell growth. The half-maximal concentration ($K_{1/2}$) for growth stimulation of this recently purified rhAMP-18 is about 5 nanomolar.

Antrum extracts containing AMP-18, peptide 77-97, or EGF each stimulated growth of AGS cells, and as expected, the rabbit antiserum to recombinant human AMP-18 precursor protein inhibited the activity of the antrum extract but not of peptide 77-97 which lacks the epitope (FIG. 11). Growth stimulation by peptide 77-97 was additive with that of EGF. Growth of AGS cells is not stimulated by scrambled peptide 77-97 or by peptide 67-85, and peptide 67-85 completely inhibits growth stimulation by peptide 58-99. HAE cells were used to test whether AMP-18 can exert an effect on epithelial cells that exist in the local environment of its synthesis. These cells, provided by Dr. Duane Smoot, Howard University College of Medicine, are not completely immortalized and therefore have limited passage number. Growth stimulation of HAE cells by peptide 77-97 was apparently additive with that of EGF (FIG. 16, left panel). Not only does the AMP peptide stimulate growth but it also acted as a motogen, resulting in more rapid migration (restitution) of cells into scrape wounds made in confluent cultures. This enhancement of wound restitution also showed high additivity with EGF (FIG. 16, right panel). Whether there is a synergism or not, the observed additivity supports that AMP-18 may play an important role in maintaining an intact stomach mucosal epithelium, and in facilitating its repair after injury. The growth of rat diploid IEC-6 cells was also stimulated by the antrum extract, peptide 77-97, and EGF, although the peptide appeared a more potent mitogen than EGF (FIG. 15). Near-maximal growth stimulation was detected at an AMP peptide concentration of 0.5 µg/ml (0.23 µM) (FIG. 15, center panel), a much lower value than the concentration needed for trefoil peptides (1 µg/µl) (~150 µM) or the α-defensin, cryptdin 3 (660 µm/ml) (~140 µM) to exert their effects in culture. The maximal mitogenic effect of rhAMP-18 on IEC-18 cells has been observed at 5 nanomolar (FIG. 18). The mitogenic effect of peptide 77-97 was corroborated by measuring [$^3$H]thymidine incorporation into DNA in IEC-6 cells which was stimulated by 68% (P<0.001) from 16,668±616 to 28,036±882 by the peptide. Stimulation of wound restitution was comparable to EGF, and apparently additive with it. Scrambled peptide 77-97 did NOT stimulate growth of IEC-18 cells or BSC-1 cells at concentrations up to 8 µg/ml. Growth of gastric NCI N-87 cells and gastric SK-GT5 cells was also stimulated by peptide 77-97, antrum extract, of EGF in a concentration-dependent manner. AMP-18 antiserum blocked the mitogenic effect of antrum extract, or EGF in a concentration-dependent manner. AMP-18 antiserum blocked the mitogenic effect of antrum extract on these two gastric epithelial cell lines, but not the proliferative effects of peptide 77-97 or EGF. Preimmune serum had no effect on growth. These results show that AMP-18 and its peptide derivatives could function in vivo to stimulate growth and restitution during repair after injury.

The failure of AMP peptide to stimulate growth of human of fibroblastic (WI-38) or epidermoid (HeLa) cells at concentrations up to 8 µg/ml suggests that the mitogenic effect of the peptide is epithelial-cell specific.

10. Competitive Inhibition of IEC-18 Cell Growth by AMP-Derived Peptides

Figure 17:
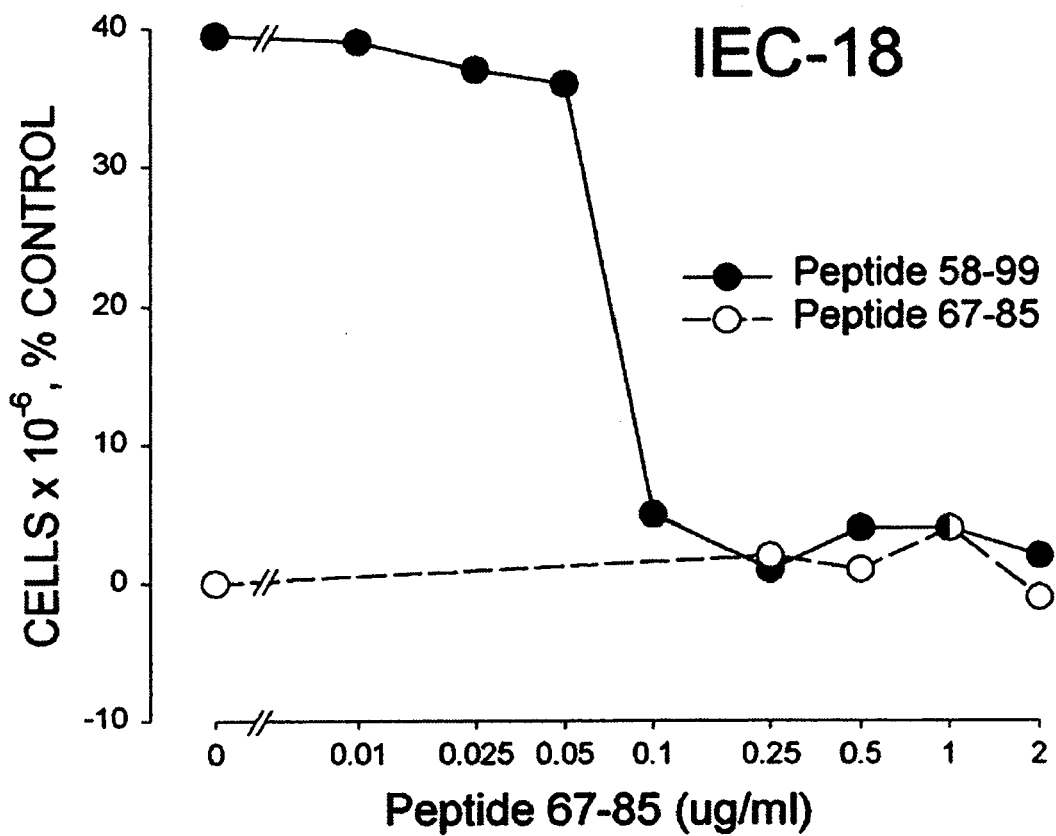
FIG. 17 shows the effect of AMP peptide 67-85 on growth of intestinal epithelial cells stimulated by peptide 58-99. Confluent cultures of IEC-18 cells were prepared. One day later, medium was aspirated and replaced with 5 ml of DMEM containing CS (0.5%) and insulin, without (control) or with mitogenic peptide 58-99 (8 µg/ml). Sister plates receiving 1 ml medium and different amounts of peptide 67-85 were incubated at 1 hr at 38° C. on a $CO_2$ incubator, and then an additional 4 ml of medium was added to each dish. Peptide 58-99 was added to 2 of the 4-sister plates at each concentration of peptide 67-85, and the number of cells was counted. In the absence of peptide 67-85, cell number increased by 290%, whereas cells exposed to peptide 58-99 increased in number by 407%, and EGF-treated (50 ng/ml) cells increased by 402% during the next 3 days. Stimulation of cell growth by mitogenic peptide 58-99 was completely abolished by preincubation of cells with 0.25 µg/ml of peptide 67-85. When added alone, peptide 67-85 (0.25 to 8 µg/ml) was not a mitogen. Values for the number of cells per culture are shown relative to multiplication of cells exposed to the vehicle during the same period.

To gain additional information about the interaction between AMP peptides and their binding site(s) on the cell surface, non-transformed rat IEC-18 cells were studied. Progressively increasing the concentration of non-mitogenic peptide 67-85 blocks growth-stimulation by peptide 58-99 if this mitogenic 42-mer exerts its effect by a receptor-mediated mechanism. Peptide 58-99 stimulated an increase in cell number of 407% compared to 290% by the vehicle in a 3-day assay. As the concentration of peptide 67-85 was raised progressively to ~0.1 µg/ml, the growth-stimulatory effect of peptide 58-99 was nearly abolished (FIG. 17). This result shows that the two peptides compete for the same surface "receptor" site.

11. Antiserum to AMP-18 Neutralizes the Mitogenic Effect of rhAMP-18

Rabbit antiserum to AMP-18 precursor recognizes rhAMP-18 on immunoblots. The antiserum also blocks the mitogenic effect of porcine antral tissue extracts (FIG. 11) and AMP peptide 58-99, and immunolocalizes AMP-18 in cells of human and murine gastric antral tissue. FIG. 18 shows that the antiserum neutralizes the mitogenic effect of rhAMP-18 in confluent cultures of IEC-18 cells, thereby extending its utility to study the recombinant as well as native protein. Although AMP peptide 77-97 requires a relatively higher molar concentration to exert its mitogenic effect than does rhAMP-18, (FIG. 13), this result also indicates that that AMP peptide is an appropriate surrogate for rhAMP-18.

To improve the yield of rhAMP-18, an EDTA-free protease-inhibitor cocktail is used, lysozyme is added to digest *E. coli* cell debris, and recombinant protein is eluted from Ni$^{2+}$ beads with 1M imidazole.

Figure 19:
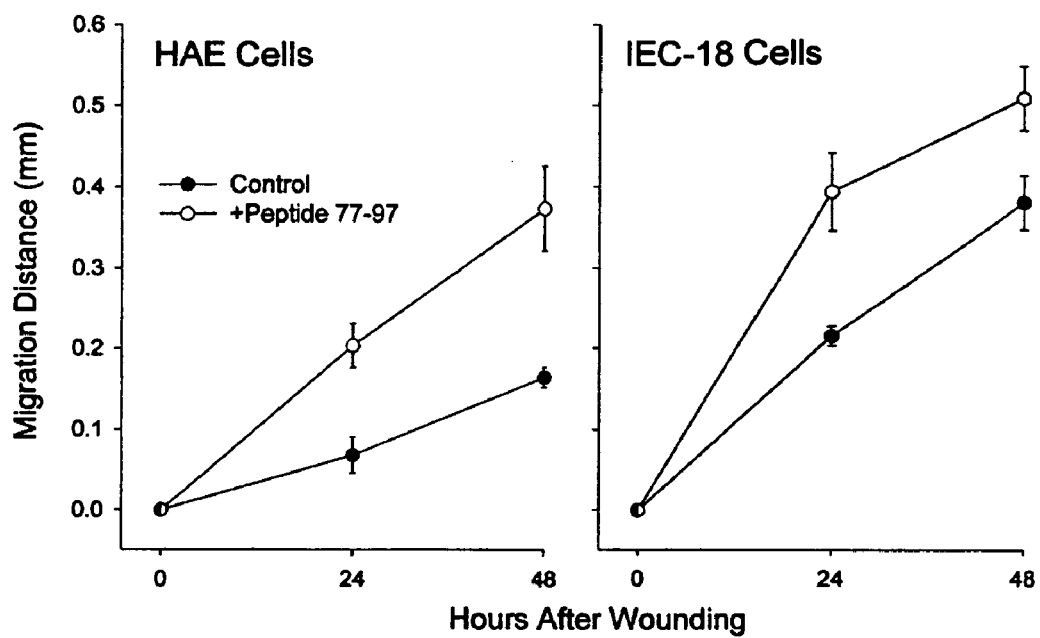
FIG. 19 shows the effect of AMP peptide 77-97 on wound restitution in human antrum (HAE) and rat intestinal (IEC-18) epithelial cells. Confluent monolayer cultures were mechanically wounded by scraping with a razor blade, and the distance that cells migrated from the wound edge was measured using a microscope eyepiece reticle. Cells migrated further in the presence of AMP peptide at each time point studied ($P<0.005$).

12. AMP Peptide Stimulates Restitution of Gastric and Intestinal Epithelial Cells after Scrape-Wounding Data presented in FIG. 19 were obtained after 24 to 48 hr exposure to AMP peptide, times before a mitogenic effect can be detected by an increase in cell number. The results indicate that AMP peptide stimulates restitution in scrape-wounded human gastric adenocarcinoma-derived cells of the HAE line, and in nontransformed rat intestinal cells of the IEC-18 line.

Thus AMP peptide rapidly stimulates restitution of gastric and intestinal epithelial cells in culture, and is expected to speed resurfacing of the injured gastric mucosa in vivo.

13. Mitogenic and Motogenic Effects of AMP Peptide in Cell Culture Support a Therapeutic Role in Gastric Mucosal Injury The synthesis of AMP-18 is confined to lumenal mucosal lining epithelial cells of the gastric antrum of humans and other mammals. Inside cells the protein is co-localized with mucins in secretion granules, and appears to be secreted into the mucus overlying the apical plasma membrane. Recombinant human AMP-18 prepared in E. coli exerts its mitogenic effect at a concentration an order of magnitude lower than growth-promoting peptides derived from the center of the mature protein. Peptide 77-97, the most potent mitogenic peptide, is amino acid sequence-specific, and appears to be cell-type specific as it does not stimulate growth of fibroblasts or HeLa cells. Mitogenesis by specific AMP peptides appears to be mediated by a cell surface receptor because certain peptides that are not active mitogens can competitively inhibit, in a concentration-dependent manner, the growth-stimulating effects of peptide 58-99 and antrum cell extracts. AMP-18 and its derived peptides exhibit diverse effects on stomach and intestinal epithelial cells making it likely they play a critical role in repair after gastric mucosal injury. These include mitogenesis, restitution, cytoprotection, and maturation of barrier function after indomethacin-mediated injury. Certain of these physiological effects can occur at concentrations that are relatively low for rhAMP-18 (<50 nM) compared to the concentrations of other gastric peptide mediators such as trefoil peptides or the $\alpha$-defensin, cryptdin 3 (>100 $\mu$M). Immunoreactive AMP-18 is apparently released by cells of the mouse gastric antrum after indomethacin gavage, and by canine antrum cells in primary culture exposed to forskolin, suggesting that the protein is subject to regulation. AMP-18 likely plays a role in physiological and pathological processes such as wound healing in the gastric mucosal epithelium in vivo as may occur in gastritis secondary to non-steroidal anti-inflammatory drugs, other pharmaceutical agents and alcohol, ulcer disease, and the consequences of H. pylori infection and inflammation.

Figure 20:
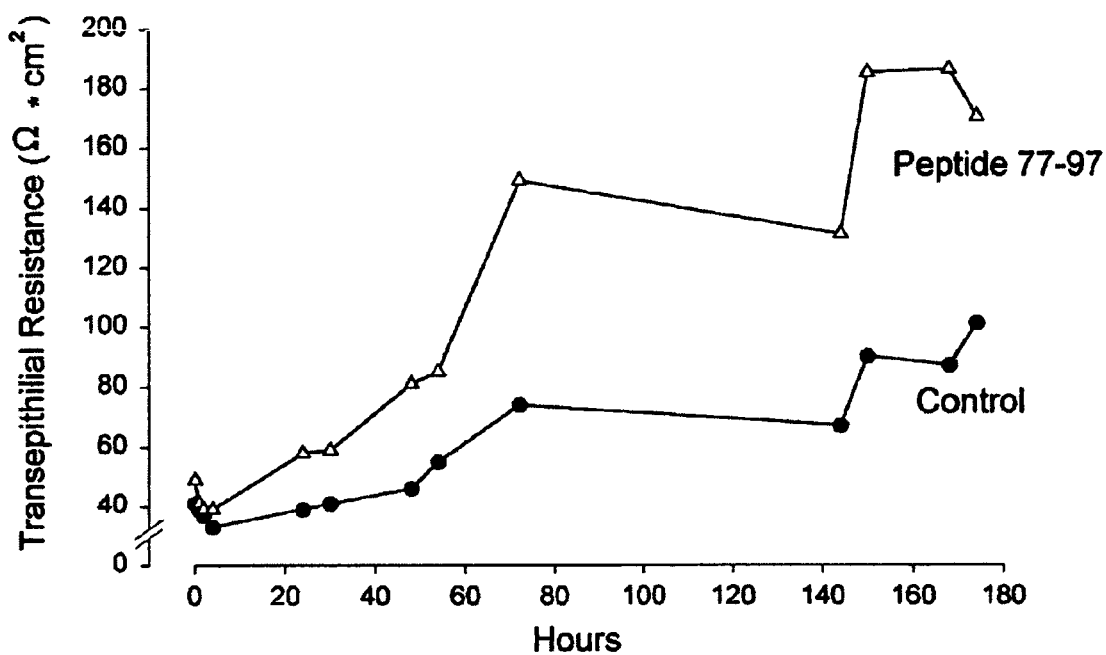
FIG. 20 shows the effect of AMP peptide 77-97 on maturation of TER. Monolayer cultures of MDCK cells were grown on permeable polycarbonate filters (0.4-µm pore size) (Transell) in DMEM containing FBS (2%) without (control) or with peptide 77-97 (8 µg/ml) for 8 days. TER was measured 24 hr after the cells were plated, and at specified times thereafter using an epithelial volt-ohm meter (EVOM, Millipore). Following each measurement, medium containing FBS without or with peptide was changed (0, 48, and 144 hr), and additional peptide 77-97 (8 µg/ml) was added at 30 and 72 hr. At 72 hr, TER in cultures that received peptide 77-97 was twice as high as in control cultures. Values are means for 3 cultures; variance is <10% of the mean. TER was measured from 3 different areas on the filter.

14. AMP Peptide 77-97 Enhances Development of Barrier Function of Epithelial Cells and is Cytoprotective Maintenance of barrier function is essential for preventing entry of foreign antigens and bacteria from the gastric lumen, and for other functions such as vectorial transport of electrolytes, water and nutrients. Acting alone or in concert with other agents, AMP-18 mediates the rapid return of barrier function following mucosal injury. To determine whether AMP peptide 77-97 could facilitate development of barrier function, and could also serve as a cytoprotective agent to prevent loss of function when reactive oxygen metabolites, indomethacin, or dextran sulfate sodium (DSS), increases mucosal permeability and compromises cell integrity needed to maintain epithelial tight junctions. Cell lines known to develop relatively high values for TER as a marker of epithelial tight junctions were used. Initially, peptide 77-97 modulates maturation of TER in monolayer cultures of well-characterized, nontransformed MDCK cells. FIG. 20 shows exposure to the peptide increases TER in the monolayer by 24 hr, and to a greater extent thereafter. This observation suggests that AMP-18 or AMP peptide speeds recovery of the GI epithelium after injury, and enhances development of barrier function.

To determine whether AMP peptide protects barrier function in a tissue culture model of mucosal oxidant injury, cell monolayers were subjected to reactive oxygen metabolite injury using monochloramine. The results in FIG. 21 (panel A) indicate that after 60 min of exposure to monochloramine, MDCK cells treated with vehicle or EGF show a substantial loss of TER, whereas the TER of cultures treated with peptide 77-97 is similar to non-injured monolayers. These results are of considerable interest because they indicate that AMP peptide but not EGF is cytoprotective under this set of conditions, whereas these two molecules were previously found to be equivalent and additive mitogens and motogens for gastric and intestinal epithelial cells. The cytoprotective effect of peptide 77-97 was also apparent in Caco2/bbe (C2) cells derived from a human colonic adenocarcinoma line in the setting of oxidant (FIG. 22, panel B) or indomethacin-mediated (panel C) injury.

Figure 22:
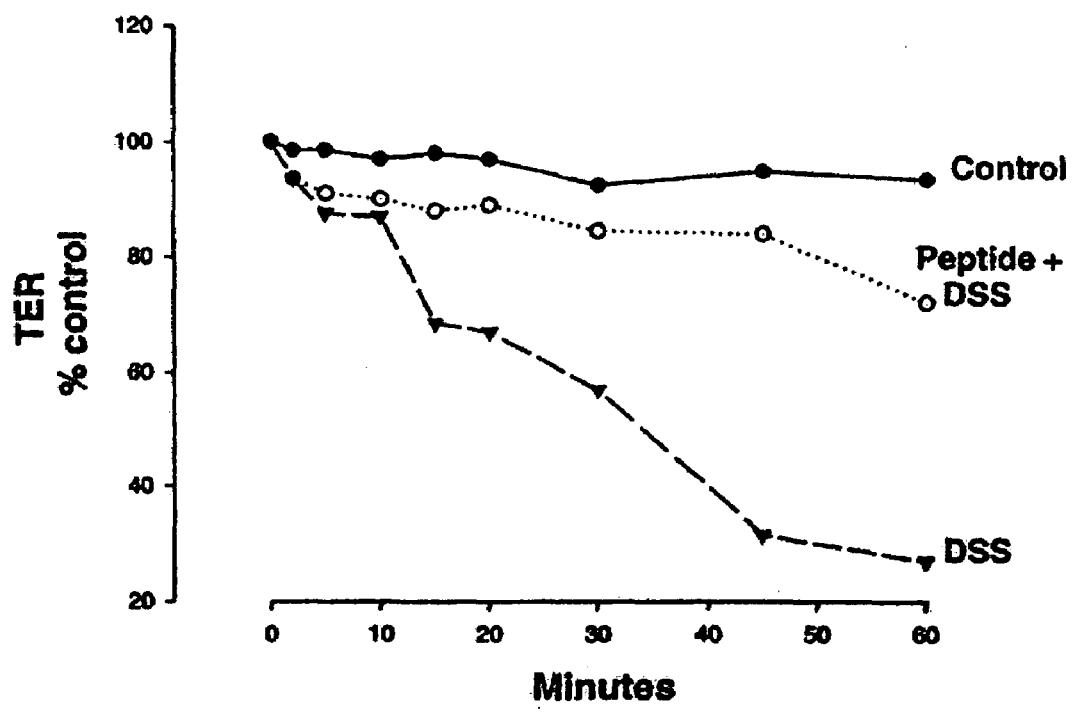
FIG. 22 shows the effect of AMP peptide 77-97 on TER following injury by DSS. C2 cell monolayers were grown in DMEM containing FBS (5%) and transferrin (10 µg/ml) on collagen-coated polycarbonate filters until a stable TER was reached (225 $\Omega cm^2$). At time 0, cells were exposed to no DSS (control), or DSS (4%) in the upper compartment of the Transwell. AMP peptide 77-97 (8 µg/ml) was added to the upper and lower compartments of the Transwell 1 day prior to the addition of DSS at time 0. TER of DSS-injured cultures treated with vehicle decreased by ~70% at 45 min, whereas peptide-treated cultures declined ~10% at that time. The peptide did not alter TER of non-injured cells. Values are means for $\geq 6$ cultures.

15. AMP Peptide Protects Against DSS-mediated Injury of Cells in Culture, and also Speeds Recovery of TER and Restitution After Injury has Occurred To evaluate the potential capacity of AMP peptide to exert a cytoprotective effect in colitis in vivo, a solution of dextran sulfate sodium (DSS) was added to the culture medium of C2 cell monolayers used to model the colonic epithelium. DSS-mediated injury of barrier function was quantified be measuring TER in these monolayer cultures. FIG. 22 indicates that DSS (4%) reduced the TER to ~30% of the control value after 45 min, and that AMP peptide was cytoprotective. This observation provides a strong physiological rationale for evaluating AMP peptide as a therapeutic agent in the murine model of DSS-mediated colitis.

Figure 29:
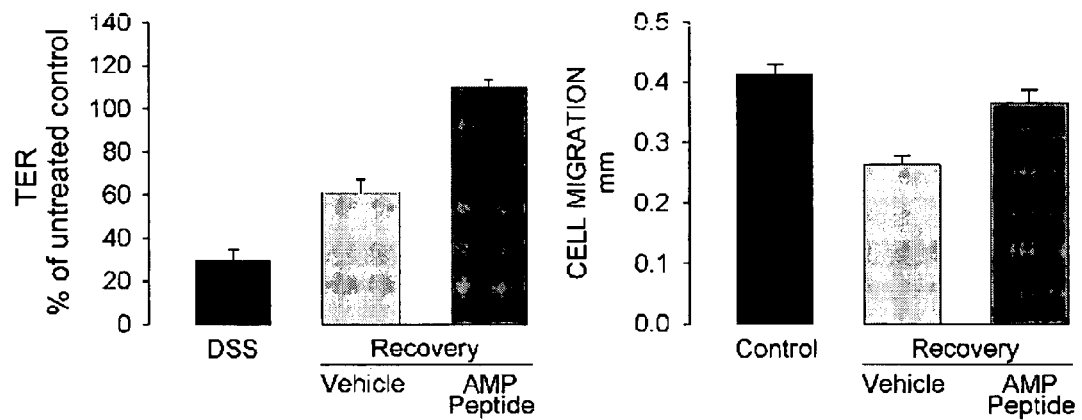
FIG. 29. AMP peptide speeds recovery of TER and restitution after DSS-mediated injury in cultures of C2 cells. After DSS reduced TER (left panel) or cell migration in scrape-wounded cultures (right panel), it was removed by aspirating the culture medium. Then fresh medium containing AMP peptide (8 μg/ml) or vehicle was added. Recovery of TER and restitution proceeded to a greater extent in the presence of AMP peptide (P<0.001).

To determine whether AMP peptide could speed recovery of TER after DSS-induced colonic cell injury, a highly sought-after functional characteristic of an agent designed to treat IBD, C2 cell monolayers were exposed to DSS (5%) for 10 min which reduced TER to 33±6% of the control value (FIG. 29, left panel). DSS was removed by aspirating the medium and replacing it with fresh medium. AMP peptide 77-97 (8 $\mu$g/ml) or vehicle was added to the culture medium, and TER was measured 18 hr later. In the presence of the vehicle, TER increased from 33% to 66±7% of the control value, whereas cells exposed to AMP peptide reached a value 112±4% of control. The salutary results in a tissue culture model of DSS-mediated colitis suggest that AMP peptide can speed recovery of barrier function in the injured colonic epithelium in vivo.

In a separate set of experiments DSS reduced restitution of scrape-wounded cultures of non-transformed diploid rat intestinal epithelial IEC-18 cells (P<0.001) (FIG. 29, right panel). When DSS was removed by aspirating the medium and the cultures allowed to recover for 24 hr after scrape wounding, cell migration during the next 24 hr was 40% greater in the presence of AMP peptide compared to vehicle (P<0.001).

Figure 23:
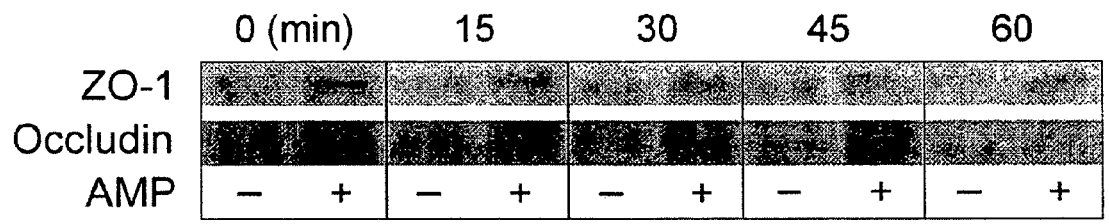
FIG. 23 shows the effect of AMP peptide 77-97 on ZO-1 and occludin after oxidant injury of C2 cells. This immunoblot shows that protein levels in the insoluble fraction are ~two-fold greater after exposure of cells to AMP peptide than to the vehicle.
Figure 24:
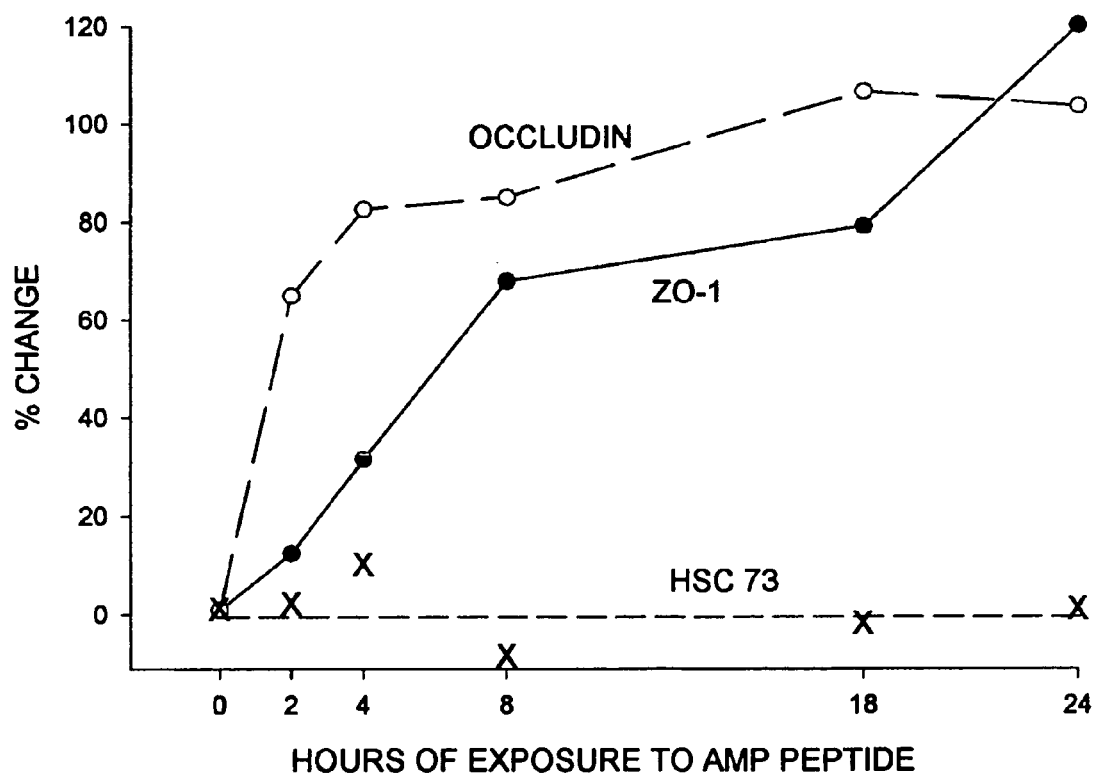
FIG. 24 shows the effect of AMP peptide on C2 cells. Cultures were exposed to the peptide for different periods of time and the insoluble fraction was obtained. Proteins were separated, immunoblots were probed with specific antisera, and the amount of each protein was quantified using laser densitometry.

16. The Cyprotective Effect of AMP Peptide in Colonic Epithelial Cells May be Mediated by Increased Accumulation of Tight Junction Proteins FIG. 21B shows that AMP peptide 77-97 blunts the fall in transepithelial electrical resistance (TER) in Caco2/bbe (C2) cells after oxidant injury. To find out how the peptide exerts its cytoprotective effect, C2 cell monolayers were treated with AMP peptide, and oxidant injury was induced with monochloramine 18 hours later. Changes in the levels of specific tight junction (TJ) proteins were checked. Cells were lysed, and proteins of the insoluble/particulate fraction were studied by immunoblotting. FIG. 23 shows that there is more immunoreactive ZO-1 and occludin in AMP peptide-treated than in vehicle-treated cells at time 0, and for 60 minutes following oxidant-induced injury, showing that the greater abundance of these TJ proteins thereby blunts loss of TER in the monolayer, preserves barrier function, and could thereby mediate AMP peptide's cytoprotective effect. This observation represents the first evidence that AMP peptide enhances accumulation of specific TJ proteins in colonic epithelial cells. This result implies that AMP peptide enhanced TJ protein accumulation during the 18 hours before cells were subjected to oxidant injury. Non-injured cells were studied and showed that AMP peptide (or rhAMP-18) rapidly increased the amount of immunoreactive occludin and ZO-1 compared to untreated cells (FIG. 24). To carry out this experiment, C2 cells were exposed to AMP peptide for different periods of time, the NP-40-insoluble fraction was obtained, Western blots were prepared, and the amount of each immunoreactive protein was quantified. A 65% increase in immunoreactivity of each protein compared to control was detected for occludin after 2 hr, and for ZO-1 at 8 hr. Hsc73, which is constitutively expressed in these cells, was not altered by exposure to AMP peptide for up to 18 hr.

Figure 21:
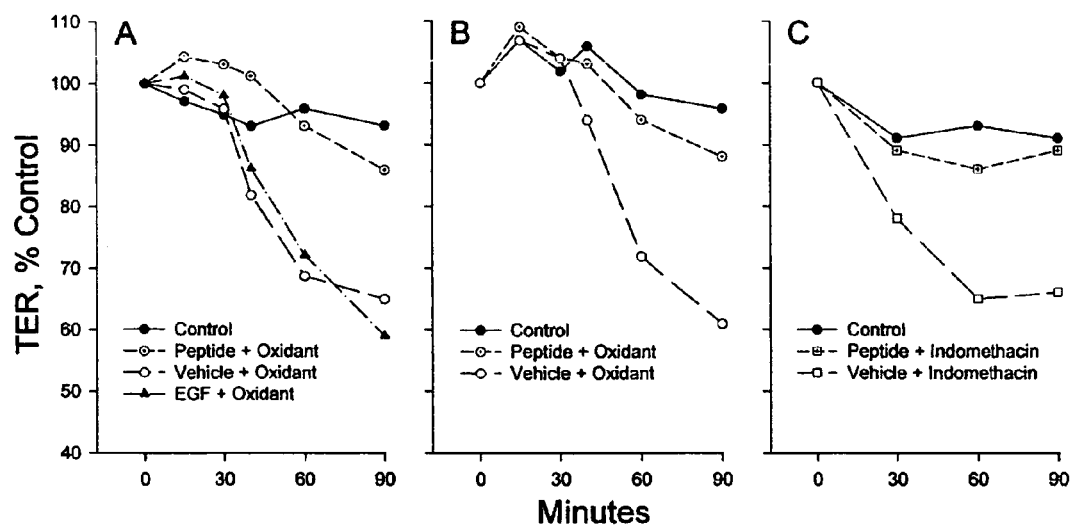
FIG. 21 shows the effect of AMP peptide 77-97 on TER in monolayers injured with the oxidant monochloramine or indomethacin. Panel A: When a stable TER was reached (330 $\Omega \cdot cm^2$) in MDCK cell monolayers the medium was changed to DMEM containing FBS (0.2%), and either peptide 77-97 (8 µg/ml) or EGF (50 ng/ml). After 18 hr, peptide 77-97 or EGF were added to the specified wells. One hour later monochloramine (0.1 mM), like the other agents, was added to the apical and basal compartments of the Transwell. Monochloramine-injured cultures treated with vehicle or EGF sustained ~35-40% loss of TER 90 min after oxidant exposure, whereas the TER of oxidant-injured cells treated with peptide 77-97 was similar to control cultures not exposed to the oxidant. Panels B, C: Caco2/bbe (C2) subclone monolayers were grown on collagen-coated polycarbonate filters until a stable TER was reached (225 $\Omega \cdot cm^2$). Spent medium was replaced with fresh medium containing FBS (0.1%) alone or with peptide 77-97 (8 µg/ml). After 18 hr, monochloramine (0.3 mM, B) or indomethacin (0.1 mM, C) was added to both compartments of the Transwell. At time 0, cultures received either vehicle (control), vehicle plus oxidant or indomethacin, or peptide 77-97 and oxidant or indomethacin. TER of injured cultures treated with vehicle decreased by ~35% at 90 min, whereas peptide-treated cultures declined ~10%. The peptide did not alter TER of non-injured cells.
Figure 30:
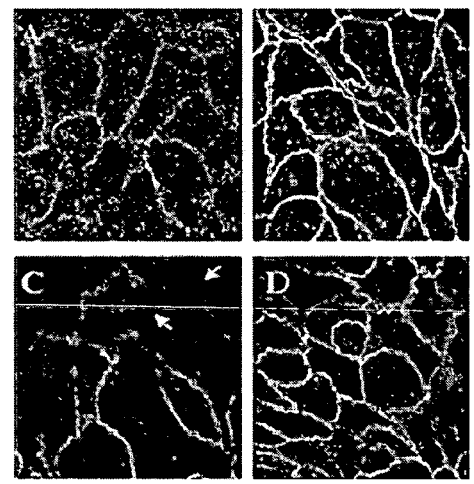
FIG. 30. Effect of AMP peptide on occludin localization by confocal microscopy in C2 cells under control conditions and following oxidant injury. Occludin immunoreactivity in a control cell monolayer (panel A) formed a uniform band outlining the cell junctions that was more intense than in the cytoplasm. When cells were exposed to AMP peptide for 18 hr (panel B), occludin appeared to be relatively more abundant in the TJs and less in the cytoplasm than in control cells. Following exposure to the oxidant monochloramine (0.3 mM) for 30 min (panel C), occludin intensity at the cell junctions was reduced and at some sites was discontinuous; occasionally it was barely visible (arrows). In cells that were pretreated with AMP peptide prior to the oxidant (panel D), occludin immunoreactivity at the cell junctions was more intense than in untreated, injured cells. Occludin was visualized with a mouse primary antibody (1:100 dilution), and Cy3-conjugated AffiniPure goat anti-mouse IgG (1:1000 dilution). Localization of occludin was analyzed using a Fluoview 200 laser scanning confocal microscope equipped with a HeNe 533 nm laser at 60× magnification. Images were compiled from a Z-series.
Figure 31:
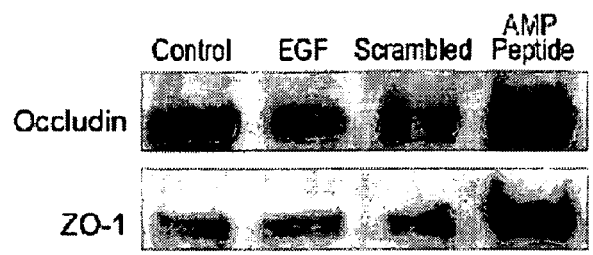
FIG. 31. Specificity of AMP peptide stimulation of occludin and ZO-1 accumulation in C2 cell monolayers. Confluent cultures were exposed to vehicle, EGF (50 ng/ml), scrambled AMP peptide (8 μg/ml), or intact AMP peptide (8 μg/ml) for 8 hr. The NP-40 insoluble fraction was prepared, and the amount of occludin and ZO-1 assessed by immunoblotting on a 10% SDS-polyacrylamide gel. Only AMP peptide enhanced accumulation of occludin and ZO-1.

To determine if the apparent increase in occludin immunoreactivity induced by AMP peptide in control cells and those subjected to oxidant injury was localized to the TJ, confocal microscopy was performed on C2 cell monolayers. FIG. 30 shows that the increased occludin immunoreactivity in control and oxidant-injured cells observed by immunoblotting (FIG. 23), is largely localized to cell junctions, presumably to the TJ. Similar results using confocal microscopy were obtained for ZO-1. Taken together, these results show that AMP peptide increases accumulation and recruitment of occludin in colonic epithelial monolayers both under control conditions and following oxidant injury, suggesting a mechanism whereby the peptide could exert its cytoprotective effect on barrier function (FIG. 21). Next it was determined if the capacity of AMP peptide to increase accumulation of TJ proteins was peptide-specific. FIG. 31 shows that AMP peptide-mediated accumulation of occludin and ZO-1 was not replicated when C2 cell monolayers were exposed to vehicle, EGF, or the scrambled AMP peptide GKPLGQPGKVP-KLDGKEPLAK)(SEQ ID NO: 19).

Figure 32:
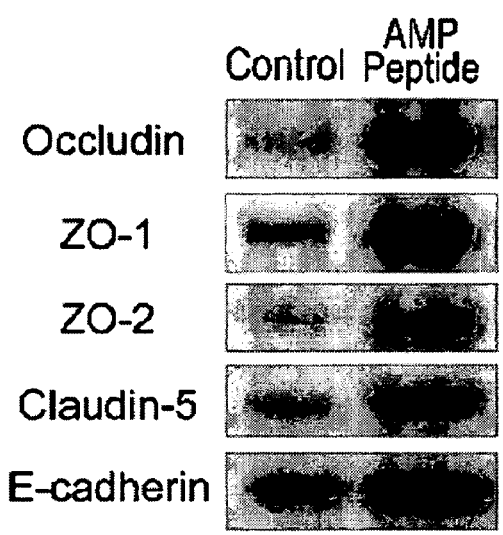
FIG. 32. AMP peptide stimulates accumulation of the tight junction-associated proteins occludin, ZO-1, ZO-2 and claudin-5, and the adherens junction protein E-cadherin in C2 cells after 8 hr.
Figure 33:
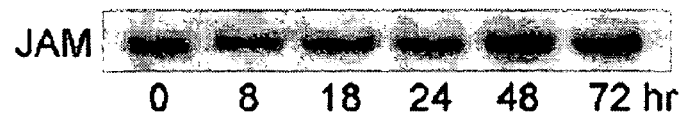
FIG. 33. Exposure to AMP peptide increases accumulation of junctional adhesion molecule (JAM) at 48 and 72 hr in C2 cells.

Because these studies showed that AMP peptide augmented the accumulation of at least two TJ proteins, this effect was characterized in greater detail. Confluent monolayers of C2 cells were treated with AMP peptide or vehicle for 8 hr. Cells were then collected, proteins in the NP-40-insoluble fraction were separated by SDS-PAGE, immunoblots were prepared, and the relative amounts of immunoreactive proteins were compared by densitometric analysis. The results in FIG. 32 show increased accumulation (3- to 6-fold) of the TJ-associated proteins occludin, ZO-1, ZO-2, and claudin-5, and the adherens junction protein E-cadherin (2-fold) in cells treated with AMP peptide. In addition, a ~50% increase in accumulation of junctional adhesion molecule (JAM), another TJ protein, was observed at 48 and 72 hr after exposure to AMP peptide compared to control (0 hr) (FIG. 33). These changes appear relatively specific for occludin, ZO-1, ZO-2, claudin-5, E-cadherin, and JAM because they were not observed for several other proteins localized in the TJ (claudin-1, claudin-2), adherens junction (β-catenin), plasma membrane (Na-K-2Cl cotransporter, α or β subunit of Na-K-ATPase), or cytosol (Rho A, hsc73).

Taken together, these results suggest that AMP peptide could exert its cytoprotective effect in colonic epithelial cell monolayers both by increasing accumulation of specific tight and adherens junction proteins, and protecting against their loss at the time of injury.

Figure 34:
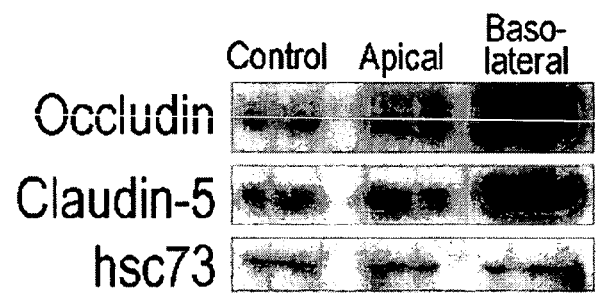
FIG. 34. Cell surface specificity of AMP peptide-stimulated accumulation of tight junction proteins. Exposure of the basolateral but not the apical plasma membrane to AMP peptide is associated with increased accumulation of occludin and claudin-5, but not hsc73. This suggests that receptors for AMP peptide reside primarily on the basolateral rather than the apical surface of these colonic epithelial (C2) cells.

17. Cell Surface Specificity of AMP Peptide-Stimulated Accumulation of TJ Proteins To better understand the mechanism(s) by which AMP peptide enhances accumulation of TJ-associated proteins, experiments were performed to determine whether the peptide exerted its effect at the apical or basolateral surface of C2 cells. Monolayers of C2 cells were grown on Transwell filters, AMP peptide (8:g/ml) was added to the apical or basolateral compartment of the Transwell, and cells were harvested 8 hr later. The NP-40-insoluble fraction was obtained, its proteins separated, and immunoblots were prepared. FIG. 34 shows that exposure of the basolateral but not the apical plasma membrane to AMP peptide was associated with increased accumulation of occludin and claudin-5, but not hsc73. These results suggest that receptors for AMP peptide reside primarily on the basolateral rather than the apical surface of colonic epithelial cells.

18. AMP Peptide Prevents Loss of Occludin in C2 Cells

Figure 35:
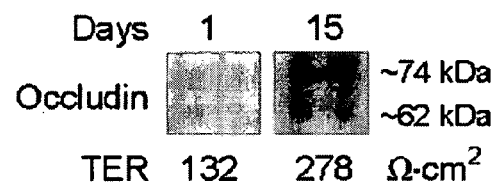
FIG. 35. A five-fold increase in occludin and a doubling of TER from 132 to $278\Omega \cong cm^2$ occurs between 1 and 15 days after plating C2 cells. Two forms of occludin (62 kDa and 74 kDa) were resolved using a 12.5% polyacrylamide gel.
Figure 36:
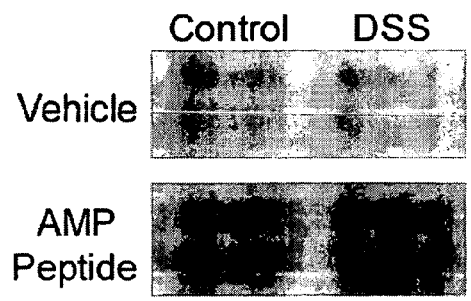
FIG. 36. AMP peptide prevents loss of occludin in DSS-mediated injury of C2 cells. Occludin immunoreactivity declined by 50% 1 hr after exposure of the cell monolayer to 4% DSS (top right panel) compared to vehicle-treated cells (top left). Treatment with AMP peptide (8 μg/ml) for 18 hr appeared to double the amount of occludin (bottom left) which was not reduced in peptide-treated cells exposed to DSS (bottom right).

The report that occludin protein and mRNA are reduced in colonic tissue of patients with IBD (Kucharzik et al., 2001) focused our attention more rigorously on this TJ protein in C2 cell monolayers used to model the colonic mucosal surface. To identify the high molecular weight phosphorylated form of occludin that is found within TJs at the apical plasma membrane, 12.5% polyacrylamide gels were used (Wong, 1997). Two major forms of occludin in the NP-40-insoluble fraction of C2 cells grown on plastic dishes were correlated with the TER of monolayer cultures grown on Transwells. Between 1 and 15 days after plating, TER increased from 132 to 278 $\Sigma \approx cm^2$, and total occludin appeared to increase nearly 5-fold (as assessed by densitometric analysis) (FIG. 35). When C2 cells were exposed to DSS (4%) which markedly reduces TER (FIG. 22), total occludin immunoreactivity declined by about 50% at 1 hr (FIG. 36, top, right panel) compared to vehicle-treated control cultures (top, left). When control cells were treated with AMP peptide (8:g/ml) for 18 hr, occludin immunoreactivity doubled (bottom panel, left) compared to vehicle-treated control cells (top, left), and when AMP peptide-treated cells were subsequently exposed to DSS, occludin immunoreactivity did not decline (bottom, right).

Figure 25:
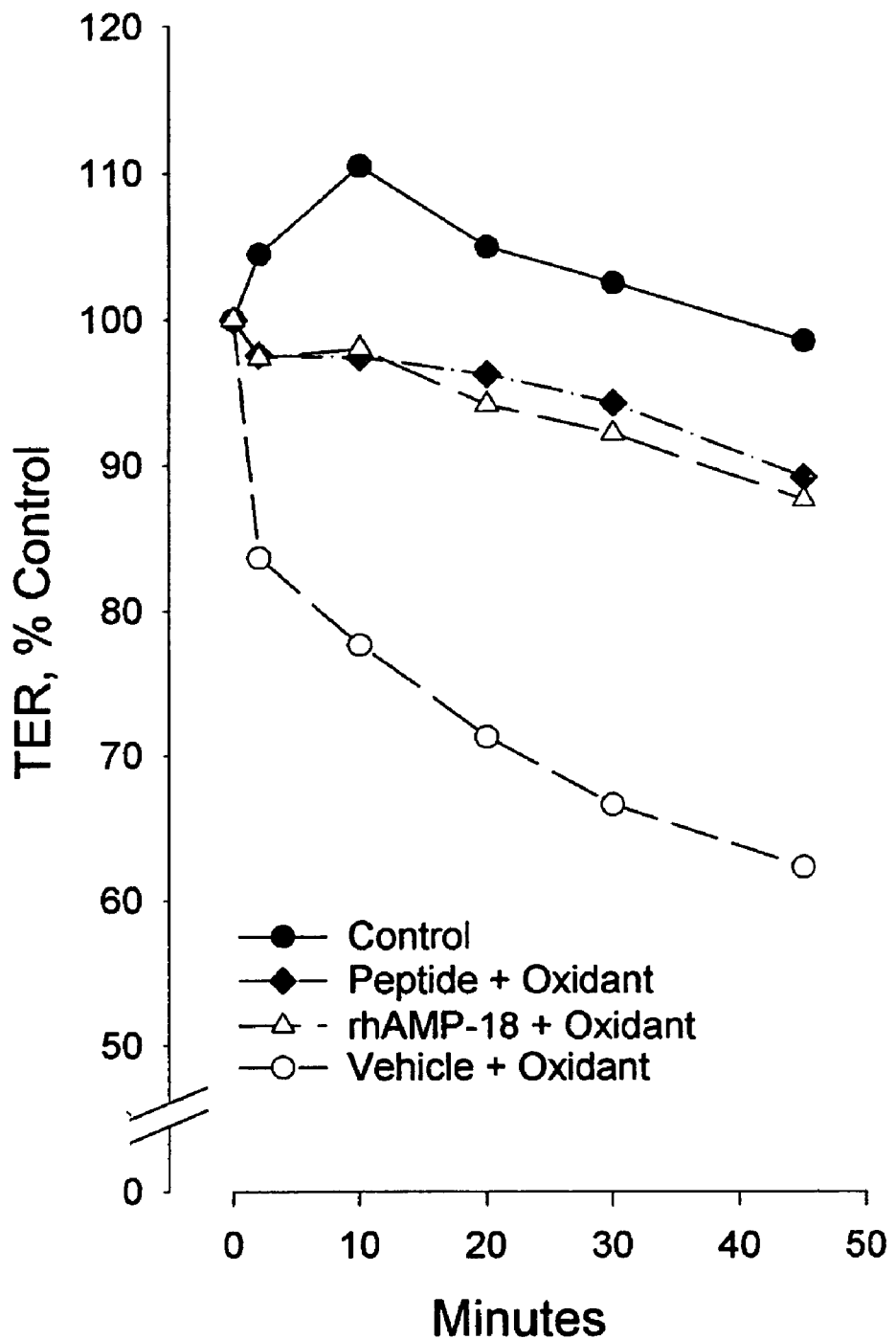
FIG. 25 shows the effect of rhAMP-18 on TER of monolayers subjected to oxidant injury. Confluent C2 cell monolayers were prepared on Transwells until a stable TER was established. Medium was replaced with fresh medium containing FBS (0.1%) alone (control), or with either rhAMP-18 (100 nanomolar) or peptide 77-97 (3.7 micromolar). After 18 hr, monochloramine (0.3 mM) was added to both compartments of the Transwell, and cultures received either vehicle (control), vehicle plus oxidant, rhAMP-18 and oxidant, or peptide 77-97 and oxidant, after which TER was measured.
Figure 26:
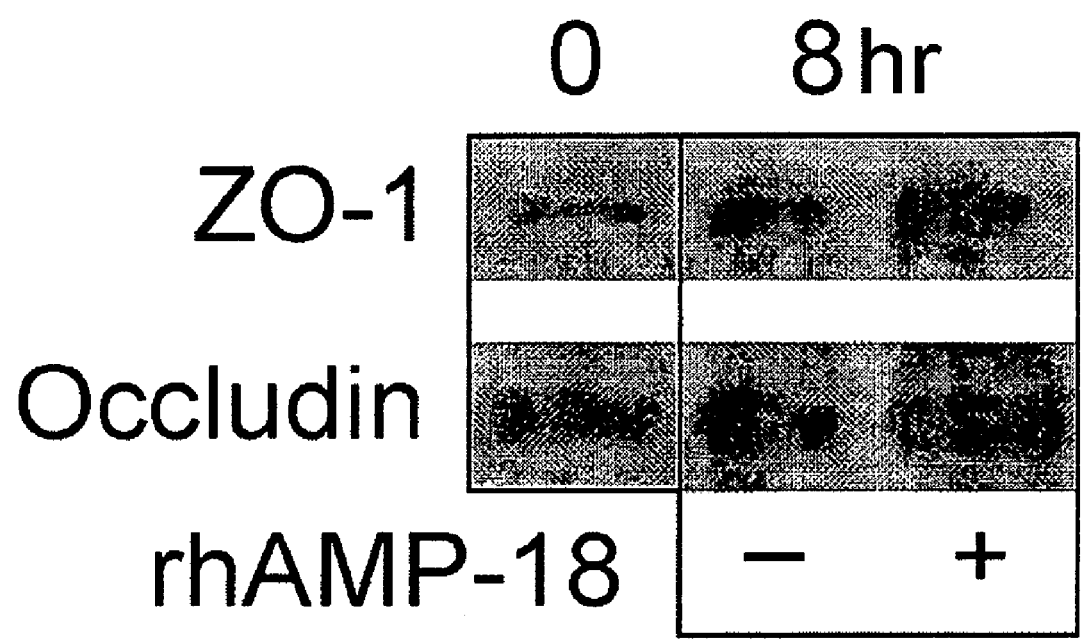
FIG. 26 shows the effect of rhAMP-19 on levels of ZO-1 and occluding in C2 cells. Monolayer cultures were treated with rhAMP-19 (100 nanomolar) or the vehicle for 8 hr. Following cell lysis, an insoluble (particulate) fraction representing cell membranes and cytoskeleton-associated TJ protein was prepared and then subjected to immunoblotting. The amount of immunoreactive ZO-1 and occludin is about two-fold greater in rhAMP-18-treated (+) cells than vehicle-treated (1) cells as estimated by laser densitometry of the same immunoblot. Equal protein loading in each lane was documented by re-probing the blot with an antibody to heat shock protein 73 which is constitutively expressed by these cells.

Purified rhAMP-18 was also tested to determine if it blunted the fall in TER in C2 cells following oxidant injury. FIG. 25 shows that exposure to monochloramine reduces TER by ~35% at 45 min, whereas cells pre-treated with either rhAMP-18 or on an AMP peptide exhibited only a ~10% decline in TER. FIG. 26 indicates that treatment of C2 cells with rhAMP-18 for 8 hr increases the amount of immunoreactive occludin and ZO-1 compared to vehicle-treated cells.

These experiments show that injuries of C2 cell monolayers inflicted by DSS or monochloramine reduce both TER and immunoreactive occludin, and that pretreatment of the cells with AMP peptide as well as rhAMP-18 exerts a cytoprotective effect that prevents both the loss of occludin and decline in TER. AMP-18 likely mediates its cytoprotective effect by enhancing accumulation of specific TJ proteins and thereby preserving barrier function along the GI tract in the setting of mucosal injury.

Figure 37:
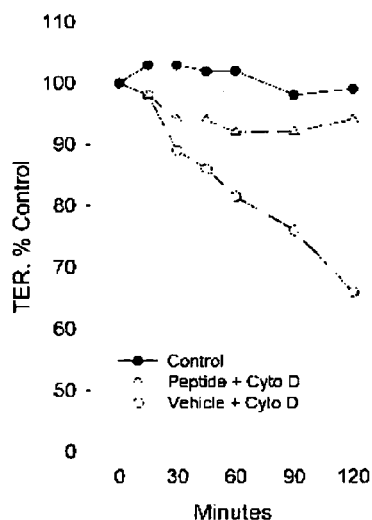
FIG. 37. AMP peptide protects barrier function following disruption of the actin filament network in C2 cells. Cytochalasin D, which disrupts actin filaments, reduced TER by ~35% in vehicle-treated cells after 2 hr, whereas pretreatment with AMP peptide prevented the decline.

19. AMP Peptide Protects Barrier Function Following Disruption of the Act in Filament Network in C2 Cells To determine if the cytoprotective effect of AMP peptide is mediated at the level of the actin cytoskeleton, C2 cell monolayers were exposed to cytochalasin D, an agent known to disrupt actin filaments and compromise barrier function (Madara et al., 1986). Exposure of the mature cell monolayer to a low concentration of cytochalasin D (0.01 µg/ml) progressively reduced the TER by 34% ($P<0.001$) (n=9 cultures) compared to vehicle after 2 hr (FIG. 37). The TER of cells pretreated with AMP peptide (8 µg/ml) for 18 hr prior to exposure to cytochalasin D did not decline significantly after 2 hr (n=11), and was higher than vehicle-treated cells (P<0.001). The capacity of AMP peptide to prevent cytochalasin D-induced barrier dysfunction suggests that it may exert its cytoprotective effect at the level of the actin cytoskeleton. Confocal microscopy revealed that treatment of the cells with AMP peptide protected perijunctional actin in the setting of oxidant (0.3 mM monochloramine) injury.

20. Administration of AMP Peptide Delays appearance of Blood in the Stool and Reduces Weight Loss in Mice with DSS Induced Colitis To evaluate the therapeutic efficacy of AMP peptide in vivo, colitis of mild to moderate severity was induced in C57BL/6 male mice by giving the animals DSS (3%) dissolved in tap water to drink ad libitum. Evidence of colitis (blood in the stool assayed by hemoccult strips) was found as early as day 1 (FIG. 27, left panel), and in all animals given injections of the vehicle subcutaneously (s.c.) by day 4. AMP peptide was administered s.c. one day before animals were given DSS, and once per day thereafter. Bloody stool was detected in fewer animals given AMP peptide than the vehicle (P<0.01; n=50).

Figure 27:
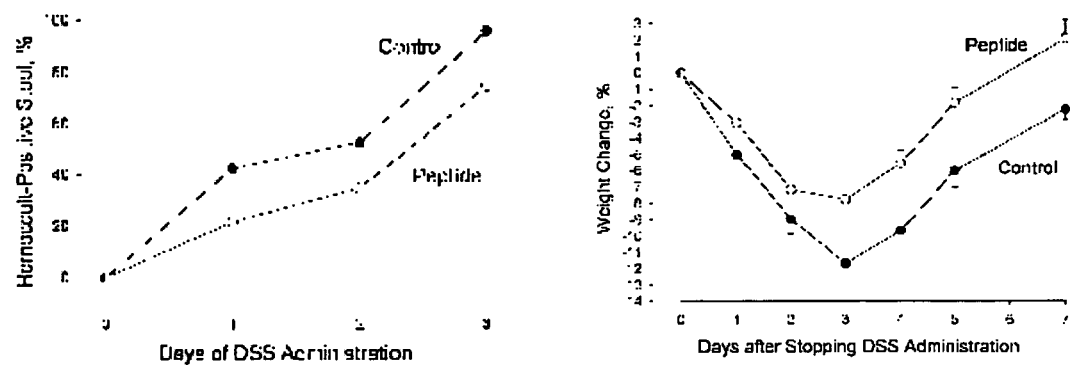
FIG. 27, Left Panel: Effect of AMP peptide on appearance of blood in the stool of mice with DSS-induced colitis. Mice (n=50) were given 3% dextran sulfate sodium, and stools were assayed daily for the presence of blood. Appearance of bloody diarrhea was delayed in animals treated with AMP peptide (10 mg/kg body weight/day) compared to those given the vehicle (P<0.01). Right panel: Effect of treatment with AMP peptide on body weight of mice with DSS colitis. After animals (n=20) received 3% DSS to drink for 4 days, they were switched to water (day 0 on graph). Mice given AMP peptide daily (10 mg/kg, s.c.) lost less weight than those given vehicle during the next 3 days (P<0.01). AMP peptide-treated mice completely recovered from the adverse effect of DSS by day 7, whereas animals given the vehicle did not (P<0.01).
Figure 38:
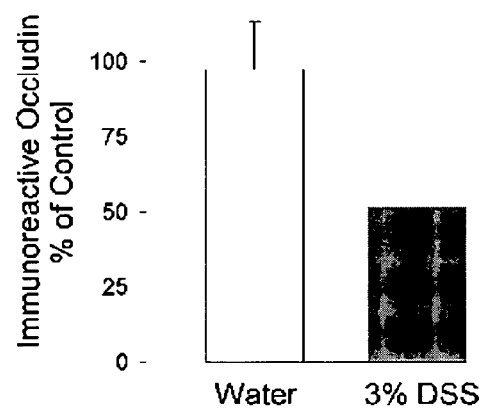
FIG. 38. Administration of 3% DSS to mice for 4 days reduced immunoreactive occludin by 50% in the colonic mucosa compared to animals given water. The colonic epithelium from each mouse was scraped into a tube, and the NP-40 insoluble fraction was obtained and analyzed for occludin content by immunoblotting. Each bar is the mean±SE for 5 mice (P<0.01).

To look for a systemic effect of treatment with AMP peptide during the development of DSS colitis, body weight was measured. During the first 4 days of DSS administration, body weight changed little in peptide- or vehicle-treated mice. Then DSS was discontinued, the animals were given water to drink (day 0; FIG. 27, right panel), and measurements of weight were continued. During the next 3 days, mice given a daily injection AMP peptide lost less weight (P<0.01) than animals given the vehicle. By day 7 after stopping DSS, the weight gain of mice given AMP peptide resulted in complete recovery of weight that was lost, whereas animals given the vehicle continued to lag behind (P<0.01). To better understand how AMP peptide could exert these salutary effects on hematochezia and weight loss in DSS colitis, studies were performed to determine if observations in cultures of C2 cells were also relevant in vivo. Because DSS treatment appeared to injure barrier function in monolayer cultures of C2 cells, assessed as a decrease in TER (FIG. 22) and reduced occludin in the detergent-insoluble fraction (FIG. 36), a question was whether DSS might adversely affect the content of this TJ protein in vivo. Mice (n=10) were given DSS (3%) or water to drink. Four days later animals were killed, the contents of the colon lumen including blood were washed out, and the mucosa was inspected. The colonic epithelial surface of mice given DSS appeared largely intact with no obvious ulcerations or denuded areas. Surface cells of visibly intact mucosa were then collected by scraping with a glass slide. Occludin levels in the NP-40-insoluble fraction were assessed by immunoblotting. FIG. 38 shows that DSS administration resulted in a 50% decline (P<0.01) in occludin immunoreactivity in mucosal cells compared to mice given water to drink. In contrast, when probed with antisera to β-catenin and hsc73, blots from mice given DSS or water to drink displayed equivalent levels of immunoreactivity, suggesting that the difference in FIG. 38 was not the result of a smaller amount of epithelial cells in scrapings obtained from DSS-treated mice than those drinking water. These results present one way in which DSS colitis in mice appears similar to IBD in humans: in both mice (FIG. 38) and humans (Kucharzik et al., 2001), colitis is associated with a decline in colonic mucosal occludin content, although the mechanisms that mediate the disease in each syndrome are known to be different. These findings appear to validate the DSS mouse as a model of colitis.

Figure 39:
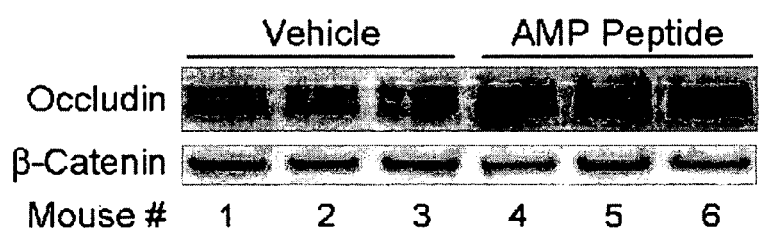
FIG. 39. Effect of AMP peptide on occludin in mouse colon. AMP peptide treatment increases accumulation of both high- and low-molecular weight immunoreactive occludin, but does not alter amount of β-catenin in colonic mucosal epithelial cells.

Next, experiments were performed to determine if AMP peptide could stimulate accumulation of occludin in the mouse colonic mucosa in vivo, as was observed in human colonic epithelial cells in culture (FIGS. 23, 24). Control mice were injected (s.c.) daily with 10, 20, or 30 mg/kg of AMP peptide for 2 to 6 days. Occludin immunoreactivity in colonic surface cells was studied with a protocol like that used to obtain the results presented in FIG. 38. Some but not all mice showed an increase in occludin content by day 2, and nearly all on day 4. FIG. 39 shows that treatment for 5 days with AMP peptide (n=3 mice) increased the amount of immunoreactive occludin in the NP-40-insoluble fraction by ~2-fold compared to vehicle-treated mice (n=3) (P<0.4), and that both high molecular weight (presumably hyperphosphorylated) occludin, as well as the lesser or nonphosphorylated forms were more abundant (P<0.004). Treatment with AMP peptide appeared to be relatively specific, as it did not alter the amount of the adherens junction protein β-catenin, as was also the case when C2 cells were treated with the peptide.

21. AMP Peptide is Cytoprotective in C2 Cell Monolayers Exposed to *Pseudomonas aeruginosa*-I Lectin, and Prevents Death in *Pseudomonas aeruginosa*-Induced Gut-Derived Sepsis in Mice Observations in cell culture and in mice with DSS-induced colitis disclosed herein show that treatment with AMP peptide likely stabilizes tight junctions in the gut and thereby prevents the lethal effect of gut-derived sepsis in mice.

The presence of *Pseudomonas aeruginosa* (PA) in the intestinal tract of critically-ill patients is associated with a 70% death rate which is 3-fold higher than in age-matched critically-ill subjects who have negative cultures for this organism. In both monolayer cultures of human colonic (C2) cells and in living mice, the bacterial surface lectin PA-I behaves as an adhesin that binds to the apical cell surface (Laughlin et al., 2000). When PA-I glycoprotein, or living bacteria were added to C2 cell monolayer cultures, the TER declined and the amount of the TJ proteins occludin and ZO-1 fell. Injection of living *P. aeruginosa* into the cecum of mice subjected to stress (30% hepatectomy and food deprivation postoperatively) was consistently lethal for the animals (Laughlin et al., 2000). These cell culture and mouse models of gut-derived sepsis (GDS) suggest that *P. aeruginosa*, through its adhesin PA-I, binds to the surface of colonic epithelial cells thereby disrupting TJ proteins (occludin and ZO-1) and induces a permeability defect that permits entry of the *P. aeruginosa* exotoxin A to breech the mucosal barrier. The translocation of exotoxin from gut lumen into the submucosal compartment and then into the circulation would subsequently kill the mouse.

Figure 40:
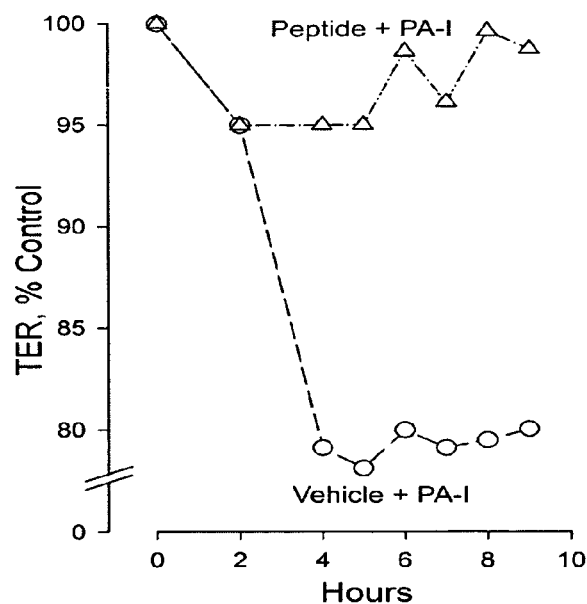
FIG. 40 shows that treatment of C2 cell monolayers with AMP peptide prevents the fall in TER caused by a lectin (PA-I) derived from the surface of *Pseudomonas aeruginosa*. Cells were prepared and treated with AMP peptide as described in the legend to FIG. 22. The TER of cells exposed to PA-I and treated with the vehicle declined by ~22% at 4 hr, whereas the TER of peptide-treated cultures was nearly unchanged at that time.
Figure 41:
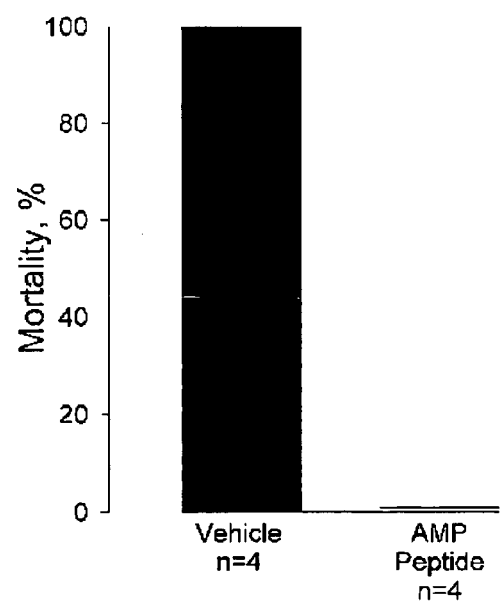
FIG. 41 shows that AMP peptide prevents death in mice with *Pseudomonas aeruginosa*-induced gut-derived sepsis. Balb/c mice were subjected to stress (partial hepatectomy and food deprivation after surgery), and received an injection of living *P. aeruginosa* into the cecum. One day later all of the mice given AMP peptide were alive, whereas all animals given the vehicle died.

To determine if AMP peptide could play a cytoprotective role in GDS, a study was carried out in C2 cell monolayers that were exposed to the PA-I lectin. The TER of cells exposed to PA-I lectin declined by ~22% at 4 hr when treated with the vehicle, whereas monolayers treated with AMP peptide decline 0-5% at that time, suggesting a cytoprotective effect (FIG. 40). Next the effect of AMP peptide was studied in the mouse model of *P. aeruginosa*-induced-GDS (Laughlin et al., 2000) using female Balb/c mice subjected to 30% hepatectomy, injection of a solution of living *P. aeruginosa* into the cecum, and food deprivation postoperatively. All 8 of the mice survived surgery. One day later, all 4 animals pretreated with the vehicle (s.c.) were dead, whereas each of 4 mice treated with AMP peptide (15 mg/kg i.p for 4 days, s.c. for 1 day) were alive and well (FIG. 41). These observations in cell culture and in vivo suggest a therapeutic rationale for using AMP peptide to treat GDS in humans.

22. AMP Peptide Increases Accumulation of Heat Shock Proteins

Figure 42:
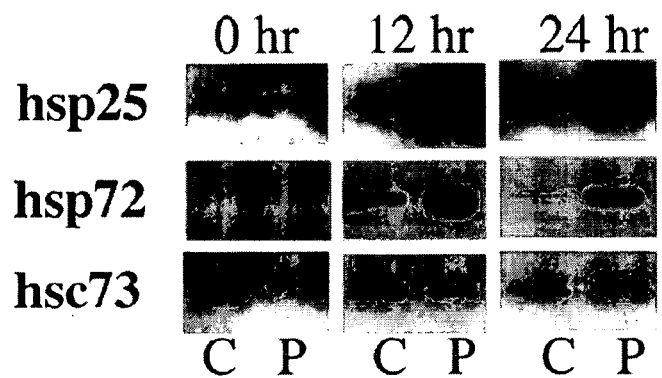
FIG. 42. Effect of AMP peptide on expression of heat shock proteins by intestinal epithelial cells after thermal injury. IEC-18 cell monolayers were subjected to non-lethal heat shock injury by exposure to 42° C. for 23 min. Immediately thereafter some cultures received AMP peptide (8 μg/ml) (P on figure); control cultures (C) received vehicle. Whole cell protein was analyzed by immunoblotting. Increased expression of hsp25 and induced hsp72 is seen 12 hr after heat shock in control cultures, but constitutive expression of hsc73 is not altered. Expression of hsp25 and 72 was increased after treatment with AMP peptide compared to vehicle at 12 and 24 hr.

In an effort to identify molecules that could mediate the cytoprotective effect of AMP peptide, it was asked if exposing intestinal epithelial cells to the peptide could modify induction of heat shock proteins (hsps) (Musch et al., 1996). Diploid non-transformed rat intestinal epithelial IEC-18 cells were used to study induction of hsps in response to thermal injury rather than C2 cells—which constitutively express hsp27 and hsp72 at high levels, possibly because they are transformed. (Hsp27 is found in human C2 cells, and hsp25 in rat IEC-18 cells. Hsp72 is often referred to as hsp70). The results depicted in FIG. 42 indicate that, as expected, hsc73 and hsp25 are constitutively expressed (0 hr), but hsp72 is not. Monolayer cell cultures were exposed to AMP peptide immediately after heat shock injury. Twelve hours later, expression of both hsp25 and hsp72 was greater in the peptide-treated than vehicle-treated cultures. An increased amount of both hsps persisted for at least 24 hr in peptide-treated cells, but declined to basal values by 48 hr. These results suggest that the cytoprotective effect of AMP peptide could be mediated, at least in part, by increased accumulation of stress proteins that protect the integrity of the actin cytoskeleton and help maintain TJs, thereby defending mucosal barrier function as described in other types of cells (Lavoie et al., 1993).

23. AMP Peptide Induces Tyrosine Phosphorylation

Figure 43:
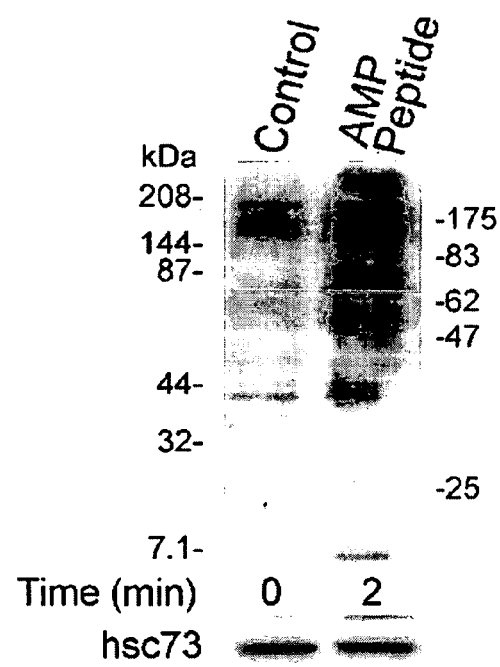
FIG. 43. Effect of AMP peptide on tyrosine phosphorylation of IEC-18 cell proteins. Cell lysates were prepared, fractionated, blotted, and probed with anti-phosphotyrosine antibody 4G10. The image is representative of immunoblots from 3 experiments prepared by exposing cells to AMP peptide (8 μg/ml) for 2 min. Protein size markers in kDa are shown on both sides of the figure. Equal protein loading in each lane was documented by probing a sister blot with an antibody (1B5) to hsc73 which is constitutively expressed by these cells.

To find signaling molecules by which AMP peptide mediates its biological effects, it was asked if the peptide stimulates tyrosine phosphorylation in GI epithelial cells. IEC-18 cells were treated with AMP peptide for different periods of time, the cells were then lysed, the proteins extracted and separated on SDS-polyacrylamide gels, blotted, and the blot was probed with 4G10 anti-phosphotyrosine monoclonal antibody. Exposure of cells to AMP peptide resulted in tyrosine phosphorylation of several proteins after two min, suggesting that the peptide stimulates tyrosine kinase activity upon its interaction with the cell surface (FIG. 43). There was a decline in the extent of tyrosine phosphorylation of several proteins after 5 min, and persistence of others for up to 60 min. These observations suggest that protein tyrosine phosphorylation plays a role in the mechanism(s) by which AMP peptide mediates its cytoprotective, mitogenic, and motogenic effects.

24. AMP Peptide Activates p38 MAP Kinase and Induces Phosphorylation of hsp25

AMP peptide increases accumulation of hsp25 in cells stressed by heat (FIG. 42), and may stabilize the actin cytoskeleton following exposure to the actin-disrupting agent, cytochalasin D (FIG. 37). Because AMP peptide appears to exert its cytoprotective effect on both hsp25 and actin, additional evidence was sought to determine if the peptide could activate the p38 MAPK/hsp27/actin filament pathway (Lavoie et al., 1995).

Figure 44:
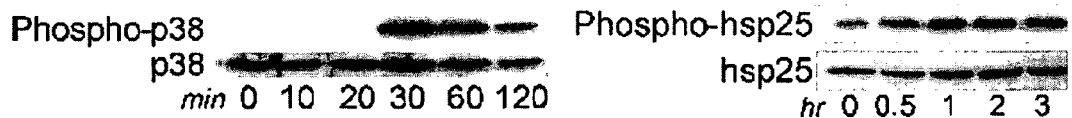
FIG. 44. AMP peptide activates p38 MAP kinase and induces phosphorylation of hsp25. AMP peptide increased p38 MAP kinase phosphorylation at 30 min with no change in total p38 MAP kinase in EC-18 cells (left panel). Treatment with AMP peptide stimulated the appearance of phospho-hsp25 at 30 min and also increased the amount of total hsp25 after 1 hr (right panel).

First the effect of AMP peptide on phosphorylation of p38 MAPK in IEC-18 cells was examined. After exposure to the peptide (8 µg/ml) for up to 2 hr, the cells were lysed, the proteins were extracted, and Western blot analysis was performed using anti-phospho-specific p38 antibody. Then the membrane was stripped and reprobed with anti-p38 antibody. FIG. 44 (left panel) reveals that AMP peptide resulted in a striking increase in p38 phosphorylation at 30 min, with no change in total p38 MAPK. Next, to see if AMP peptide stimulated phosphorylation of hsp25, a specific anti-phospho-hsp25 antibody (Affinity BioReagents) was used to probe a blot prepared using AMP peptide-treated IEC-18 cells as above. Treatment with AMP peptide stimulated the appearance of phospho (P)-hsp25 at 30 min, and was also associated with an increase in total hsp25 after 1 hr (FIG. 44, right panel).

Figure 45:
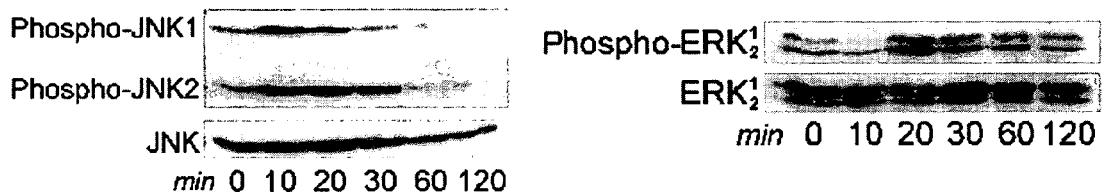
FIG. 45. JNK1/2 and ERK1/2 are rapidly activated by AMP peptide as indicated by the appearance of phosphorylated JNKs after 10 min (left panel) and ERKs at 20 min (right panel).

Taken together with observations disclosed herein, these results suggest that AMP peptide activates the p38 MAPK/hsp27/actin pathway. These findings are also consistent with the hypothesis that an early effect of AMP peptide-induced stimulation of hsp25/27 phosphorylation mediates entry of P-hsp25 into the nucleus (Geum et al., 2002) wherein it functions as a transcriptional activator, whereas at later times, P-hsp25 may act to stabilize the actin cytoskeleton by binding to the microfilaments (Huot et al., 1996). Because AMP peptide also stimulates mitogenesis and motogenesis, a question was whether if the JNK and ERK pathways were also activated. FIG. 45 shows that both JNK1/2 and ERK1/2 appear to be activated by AMP peptide, as indicated by the rapid appearance of phosphorylated JNK and ERK.

25. AMP Peptide Activates Protein Kinase C Zeta

To learn more about how AMP peptide could participate in the establishment of TJ structures and epithelial cell polarity during epithelial wound healing, attention was focused on protein kinase (PK) C zeta (ζ), an atypical PKC that appears to be required for assembly of TJs (Suzuki et al., 2001). PKCζ, presumably in its active form phospho-PKCζ, regulates TJs, apparently by interacting with several TJ-associated proteins including occludin, PAR-6, and PAR-3. In C2 cells, AMP peptide stimulated an increase in phosphorylation of PKCζ within 20 min when studied by immunoblotting. This was confirmed and extended with confocal microscopy which showed accumulation of phospho-PKCζ in the cell cytosol 20 min after exposure to AMP peptide and its subsequent translocation to the TJ at 60 min. These findings show that AMP peptide acts to establish new TJ structures during epithelial wound healing after cell injury by activating (phosphorylating) PKCζ.

Materials and Methods

1. Isolation of Antrum-Specific cDNA Clones cDNA clones for the gastrointestinal peptide gastrin, which regulates gastric acid secretion as well as mucosal and pancreatic cell growth (Yoo et al., 1982) were isolated. From these screens several other mRNAs expressed relatively specifically in the antrum of the stomach were found. The open reading frame (ORF) in one of these RNAs was highly conserved between pig and man, and predicted a novel conserved protein of no immediately apparent function. Using specific antibodies, it was shown that similar protein species are present in the stomach antrum mucosa of all mammals tested. There is tissue specificity of expression of these sequences and they are apparently ubiquitously present in the antrum mucosa of mammalian species.

2. RNA Expression

The isolation of the cDNA clones was predicted on a preferential expression in the mucosa of the stomach antrum and this has been confirmed initially by Northern blot hybridization of RNAs from various tissues probed with the cDNA sequences and subsequently by protein analysis. The Northern blots showed the specificity of mRNA expression within the gastrointestinal tract of the pig. Highest mRNA expression was in the antrum mucosa, variable amounts in the adjacent corpus mucosa and undetectable levels in fundus, esophagus and duodenum. The non-mucosal tissue of the antrum and corpus contained little RNA reacting with the cDNA probe.

3. Antibodies to Expressed Protein

The open reading frames (ORFs) of the human and pig cDNA clones predict very similar relatively low molecular weight (MW) proteins, which have no close homologs to known proteins in the computer databases and therefore give little indication of possible function. As an approach to study the biological role of the presumptive proteins, the full cDNA sequences were expressed in *E. coli*, using a vector that also encoded an N-terminal His6-tag (SEQ ID NO: 16). Unfortunately, as expressed in bacteria the polypeptide products are insoluble and not readily amenable to biochemical studies. However, the bacterial product of the human cDNA was separated on sodium dodecyl sulfate (SDS) gels used as an immunogen in rabbits to elicit antisera. The sera were screened against protein extracts of antral tissue from a number of mammalian species. This procedure has successfully produced several high-titer, low background antisera capable of recognizing both the immunogen and proteins of about 18 kDa expressed in the antrum of the mammals tested. The bacterially-expressed protein migrates more slowly because it contains the signal peptide sequence was well as a His6-tag (SEQ ID NO: 16). The preimmune sera showed no significant 18 kDa reactivity. The cross-reactivity of the antisera raised against the protein expressed from the human cDNA clone with proteins of very similar MW in antrum extracts from a variety of mammals (pig, goat, sheep, rat and mouse; the last consistently migrates slightly more rapidly in SDS gels) supports the level of conservation of amino acid sequence predicted by comparison of the ORFs of the human and pig cDNAs (see FIG. 10). In subsequent experiments, human AMP-18 with a signal peptide was produced in bacteria.

The preimmune sera give insignificant reactions on Western blots of all tissue extracts, while the two immune sera (at up to 1:50000 dilution) both give major bands of 18-20 kDa only, and those only in stomach antrum extracts, and to a lesser degree in the adjacent corpus extracts. The sera were raised against bacterially-expressed protein so there is no possibility of other exogenous immunogens of animal origin.

As determined by immunoblots, the specificity of expression to the antrum is even greater than the Northern blots would suggest, and the strength of the signal from antrum extracts implies a relatively high abundance of the protein, although quantitative estimates were not made. Significant antigen was not detected in non-stomach tissues tested.

The immunohistochemistry showed insignificant staining of antral tissue by both preimmune sera, while both immune sera stained the surface mucosal cells very strongly at considerable dilutions. The preimmune sera did not lead to immunogold staining in the immunoelectron microscope study. The growth factor activity of antrum extracts is inhibited by both immune, but not preimmune sera. Finally, the results with a synthetic peptide, which has growth factor activity, is inhibited by the immune but not the preimmune sera, and carries epitopes recognized by the immune but not the preimmune sera, further validate the specificity of these reagents.

4. Northern Blot Hybridization of RNAs from Pig Gut Mucosal Tissues

Total RNA was electrophoresed, transferred to a membrane and hybridized with a labeled pig AMP-18 cDNA probe. The source of the RNA sample for each lane was: distal duodenum, proximal duodenum, antrum, adjacent corpus, fundus, and esophagus. Equal amounts of RNA were loaded. The signal from RNA of the antrum adjacent corpus was variable. Size markers (nucleotides) were run on the same gel for comparison.

5. Immunoblots Using a Rabbit Antiserum Raised Against the Bacterial-Expressed Protein Directed by the Human Antrum-specific cDNA Clone Whole tissue proteins were dissolved in SDS buffer, electrophoresed, and transferred to membranes that were reacted with immune serum (1:50000). Bound antibody molecules were detected using peroxidase-labeled anti-rabbit antibody. Preimmune serum gave no specific staining of parallel blots at 1:200 dilution.

Immunoblots of high percentage acrylamide gels showed that the antisera recognized epitopes on the synthetic peptide 78-119. The reaction of peptide 78-119 with the antibodies was not unexpected because this region of the sequence was predicted to be exposed on the surface of the protein and to be antigenic. Not only does this further substantiate a belief that AMP-18 or its immediate precursor, is a growth factor, for epithelial cells, but also provides a basis for analysis of the bioactive (and antigenic) regions of AMP-18, and a tool for the assessment of cell receptor number and identity. Chemical synthesis of peptides also makes available a convenient and rapid source of considerable quantities of pure "wild-type" and "mutant" reagents for further cell studies. The synthetic peptide 78-119 apparently acts by the same mechanism as the antrum protein, because their maximal effects are not additive.

6. Sequence and Predicted Structure of the Pre-AMP Open Reading Frame

The predicted amino acid sequences for human and pig are 76% identical. The predicted signal peptides are not bold; the N-terminus of native pig AMP has been shown to be aspartate (FIG. 10).

7. Structure of the Native Protein

The ORF's of the human and pig cDNAs predicted polypeptides of similar general structure (FIG. 10). The predicted molecular weights for the otherwise unmodified human and pig proteins was 18.3 and 18.0 respectively; these values are in good agreement with electrophoretic mobility in SDS the of antrum proteins reacting with the antisera of the present invention.

The antisera was used to assist in the purification of the protein from extracts of pig antrum mucosa. Immnoaffinity methods applied to total tissue extracts have not proven very effective, but by using immunoblots to monitor cell-fractionation, gradient centrifugation and gel electrophoresis sufficient amounts of the pig 18 kDa polypeptide was purified to confirm by sequencing that the native N-terminus is one predicted by cleavage of about 20 amino acids from the N-terminus of the ORF precisely at the alanine-aspartate site anticipated for signal peptide removal. Despite the abundance of asparagine residues, none fit the consensus context for glycosylation. Fairly extensive regions which may possess amphipathic helix forming propensity. The latter may represent units within the protein or as peptides after processing. Using circular dichroism the synthetic peptide representing amino acids 126-143 in the human preAMP sequence (FIG. 3) is readily induced to become helical in moderate concentrations of trifluoroethanol conditions used to assess helix propensity for some bioactive peptides, including anti-microbial peptides of the magainin type (see for example Park et al., 1997).

8. Localization of AMP-18

The antisera to AMP-18 have proven to be excellent histochemical probes, reacting strongly with sections of the mouse antrum region but not with the fundus, duodenum or intestine, confirming the results of the immunoblots. The preimmune sera give negligible reactions even at much higher concentration. The AMP-18 protein appears to be concentrated in mucosal epithelial cells lining the stomach lumen, although lesser signals in cells deeper in the tissue and along the upper crypt regions suggest that cells may begin to express the protein as they migrate toward the lumenal layer. Higher magnification of the histochemical preparations indicates only a general cytoplasmic staining at this level of resolution; there are some patches of intense staining that may be the light microscope equivalent of granule-packed regions of some lumenal surface cells seen by electron microscopy (EM). The localization of AMP-18 in the antrum mucosa is therefore very different from those cells synthesizing gastrin which are deep in the mucosal layer.

9. Immunoelectron Microscope Localization of the AMP-18 Antigens in the Mouse Stomach Antrum Mucosal Cells The tissue pieces were fixed in 4% formaldehyde and processed for embedding in Unicryl. Thin sections were reacted with rabbit anti-human AMP-18 antisera (1:200); bound antibodies detected by Protein-A conjugated to 10 nm colloidal gold. The reacted sections were stained with lead citrate before viewing (20,000×). The gold particles are visible over the semi-translucent secretion granules, which appear much more translucent here than in the standard glutaraldehyde-osmium-epon procedure (11,400×) because of the requirements for immuno-reactivity. Negligible background was seen on other cytoplasmic structures.

The general structure of the protein implies a possible secretory role so a precise intracellular localization would be valuable. This requires EM immuno-cytochemical procedures. Standard embedding and staining methods reveal that, as previously reported by many others, the antrum region (e.g. Johnson and McMinn, 1970) contains mucosal epithelial cells which are very rich in secretory granules. Preliminary immuno-EM data show the immune sera used at 1:200-1:800 dilution react specifically with the secretion granules. The latter appear somewhat swollen and less electron opaque than in standard fixation conditions and the differences in density are harder to discern, but overall the cell structure is quite well-preserved for stomach tissue fixed and embedded under the less stringent conditions required to preserve immuno-reactivity. At 1:100 dilution, the preimmune sera exhibited negligible backgrounds with no preference for the secretion granules.

10. Growth Factor Activity on Epithelial Cell Cultures

A function for AMP-18 is that it is a growth factor at least partly responsible for the maintenance of a functional mucosal epithelium in the pyloric antrum and possibly elsewhere in the stomach. Initially, stomach epithelial cell lines were not immediately available, but kidney epithelial cell systems (Kartha et al., 1992; Aithal et al., 1994; Lieske et al., 1994) were used. A fractionated antrum mucosal cell extract was used for these experiments. Using immunoblotting as a probe to follow fractionation, on lysis of the mucosal cells scraped from either pig or mouse antrum, the AMP-18 antigen was recovered in the 35S fraction on sucrose density gradients. Such high speed supernatant fractions served as the starting material for studies on cell growth. Unexpectedly, these extracts stimulated a 50% increase in confluent renal epithelial cells of monkey (BSC-1 cells), but had no effect on HeLa or WI-38 fibroblast cells. The stimulation of BSC-1 cells was at least as effective as that observed with diverse polypeptide mitogens, including EGF, IGF-I, aFGF, bFGF and vasopressin, assayed at their optimal concentrations. Comparable growth stimulation by the antrum extracts was observed when DNA synthesis was assessed by measuring [$^3$H]thymidine incorporation into acid-insoluble material. The biological activity of the antrum extracts survived heating for 5 minutes at 65° C., and dialysis using a membrane with $M_r$ cutoff of 10 kDa, which would eliminate most oligopeptides; this treatment removes 60-70% of polypeptide material, but spared AMP-18 as assayed by immunoblots. More importantly, mitogenic stimulation of BSC-1 cells by the mouse or pig antrum extract was inhibited when either of two different antisera to the human recombinant preAMP-18 (expressed in bacteria) was added to the culture medium. Preimmune sera (1:100 to 1:800) had no effect on cell growth, nor did they alter the mitogenic effect of the antrum extracts. These observations suggest that gastric mucosal cell AMP-18 functions as a potent mitogen for kidney epithelial cells, which do not normally express this protein.

To gain further evidence that the growth-promoting activity in the partially fractionated antrum extracts was mediated by the AMP-18 protein, an aliquot of the mouse extract was subjected to SDS-polyacrylamide gel electrophoresis; the method used previously to determine the N-terminal sequence of the natural protein. The gel was cut into 2-mm slices and each slice was extracted with 3% acetonitrile in phosphate-buffered saline containing 1% BSA. The extract supernatants were assayed for mitogenic activity. The results indicated that one slice containing protein in the 16-19 kDa range possessed growth-promoting activity. Significantly, this growth response was blocked by the immune but not the pre-immune sera. Taken together with the relatively low sedimentation rate of the protein, these findings provide additional evidence to support the conclusion that AMP-18 is an epithelial cell mitogen and that it functions as a monomer or possibly a homotypic dimer. It also implies that the structure of the protein is such that it can readily reacquire a native conformation after the denaturing conditions of SDS-gel electrophoresis.

To assess the interaction of the antrum growth factor activity with other cytokines, its activity was tested to determine if it was additive with EGF in epithelial cell cultures. EGF (50 ng/ml) added with untreated mouse antrum extract (10 μg/ml), or heated, dialyzed pig extract (10 μg/ml) exhibited additive stimulation of mitogenesis; up to 74% increase in cell number above the quiescent level; the greatest stimulation observed so far for any factor using the BSC-1 cell assay. An example of this additivity is shown for an AMP-peptide and EGF on AGS cells in FIG. 11. This observation suggests that AMP-18 and EGF initiate proliferation by acting on different cell surface receptors. It also implies that AMP-18 growth factor activity might normally collaborate with other autocrine and paracrine factors in the maintenance or restitution of the epithelium. In view of the results with EGF, it is likely that AMP-18 is secreted at and acts upon the apical face (i.e., stomach lumenal face) of the epithelial cell layer while other factors (for which EGF may serve as an example) act from the basal surface.

11. Bioactivity of Gastrokine (AMP-18) Related Peptides

The activities of synthetic peptides of the present invention are unexpected. Peptides based on the ORF of the human cDNA clone peptides were synthesized in the University of Chicago Cancer Center Peptide Core Facility, which checks the sequence and mass spectra of the products. The peptides were further purified by HPLC. Five relatively large oligopeptides (of about 40 amino acids each) approximately spanning the length of the protein without including the signal peptide, were analyzed. One peptide 42 amino acids long spanning amino acids lys-78 to leu-119 of the pre-AMP sequence (peptide 58-99 of the matured form of the protein;

see Table 1), including a predicted helix and glycine-proline (GP) turns, gave good mitogenic activity. This response was blocked by the specific antiserum, but not by the preimmune sera.

A 14 amino acid mitogenic domain is in bold type. *Peptides are identified by their position in the amino acid sequence of the pre-gastrokine (preAMP-18). #AA; number of amino acids in a peptide. $K_{1/2}$; concentration for half-maximal growth stimulation. **scrambled Overlapping inactive peptides can inhibit the activity of the mitogenic peptides: that is, human peptides 78-88 and 87-105 block the activity of peptide 78-119, and while peptide 87-105 blocks the activity of peptide 104-117, the peptide 78-88 does not. Peptides 78-88 and 87-105 block the activity of the protein in stomach extracts.

12. The Growth Stimulatory Domain of Gastrokine (AMP-18)

Finding that a 42-amino acid peptide representing a central region of the novel antrum mucosal cell protein AMP-18 had mitogenic activity similar in character to that of the intact protein in pig and mouse antrum extracts (Table 1), has facilitated the characterization of the bio-active region of the molecule. A peptide including amino acids at positions 78-119, gave similar maximal stimulation of growth of the BSC-1 epithelial cell line to that given by the tissue extracts and was similarly inhibited by several different antisera raised in rabbits to the bacterially-expressed complete antrum protein. The mitogenic activity of a number of synthetic "deletion" peptides related to peptide "78-119" are summarized in Table 1. Growth activity determinations have so far been accomplished with the kidney epithelial cell line as well as several gastric and intestinal lines.

The original 42 amino acid sequence of peptide 78-119 was broken into three segments bounded by lysine (K) residues; N-terminal to C-terminal these are peptides with amino acids at positions 78-88, 87-105 and 104-117. Of these only peptide 104-117 possessed mitogenic activity giving a similar plateau of growth stimulation but requiring a higher molar concentration than the original peptide "78-119"; this is reflected in the higher $K_{1/2}$ value, which suggests that 14-amino acid peptide has 30-40% of the activity of the 42-amino acid peptide. A conclusion from this is that the smaller peptide has less binding affinity for a cell receptor, perhaps due to a lessened ability to form the correct conformation, or alternatively because of the loss of ancillary binding regions. The latter notion is supported by the observations that peptides "78-88" and "87-105" can antagonize the activity of intact 42-mer peptide 78-119; these peptides also antagonize the activity of antrum extracts further supporting the validity of synthetic peptides as a means to analyze the biological function of the novel protein. An additional aspect of the invention is that peptide 87-105, but NOT 68-88, antagonizes the activity of peptide 104-117; note that peptide 87-105 overlaps the adjacent 104-117 sequence by two residues.

Taken together these results may be interpreted by a relatively simple linear model for the growth-stimulatory region of AMP-18; viz, there is an N-terminal extended binding domain (predicted to be largely helix, the relative rigidity of which may explain the linear organization of the relevant sequences as determined in the cell growth studies), followed by a region high in glycine and proline with no predicted structure beyond the likelihood of turns. It is this latter region which contains the trigger for growth stimulation. The specificity of antagonism by peptides 78-88 and 87-105 may be based on whether they overlap or not the agonist peptides 78-119 and 104-117; for example 78-88 overlaps and inhibits 78-119, but does not overlap or inhibit 104-117. The specificity of competition by these peptides taken with the inactivity of the 78-119 scrambled peptide, strengthens a conclusion that AMP-18 interacts with specific cellular components. Further evidence that the receptor binding region extends N-terminally from peptide 104-117 is provided by the enhanced activity of peptide 97-117 which contains a seven amino acid N-terminal extension of 104-117. A peptide with a four amino acid extension in the C-terminal direction (peptide 104-121) appears to have slightly less activity to the parent 104-117, but does include a natural tyrosine, which makes possible labeling with radioactive iodine, which allows determination of the binding of AMP-related peptides to cells, initially by assessment of number of binding sites and subsequently detection of the receptor protein(s).

The peptide 97-107 was used for most tests because of its activity (equal to the 42-mer) and its relative economy (21 amino acids in length). However, a C-terminal extension to the tyr-121 gives the most active peptide thus far, perhaps because it stabilizes secondary structure. Even though this peptide does not match the nanomolar activity of EGF, for example, it is much more potent than reported for trefoil peptides (Podolsky, 1997). An estimate for the activity the intact AMP protein is ca. 1-10 nM.

13. Expression of Recombinant Protein

*E. coli.* Recombinant constructs are generally engineered by polymerase-chain-reactions using synthetic oligonucleotides complementary to the appropriate regions of the full-length cDNA sequences within the PT/CEBP vector and extended by convenient restriction enzyme sites to enable ready insertion into standard vector polylinkers. The initial experiments with expression of the AMP ORF in bacterial systems employed an expression vector PT/CEBP, which included an N-terminal His6-tag (SEQ ID NO: 16) (Jeon et al., 1994), intended to facilitate the purification of the expressed protein on Ni-NTA resin (Qiagen). Expression of the full-length human cDNA within this vector in the host BL21(DE3)pLyS gave good yields of insoluble protein, which after electrophoresis under denaturing conditions was suitable for use as an immunogen in rabbits to obtain specific high-titer antibodies, but which has not been useful for analysis of the protein's native structure and function. This insolubility is most probably due to the presence of an unnatural N-terminus, having a His6-tag (SEQ ID NO: 16) upstream of hydrophobic signal peptide, in the expressed protein. Engineering vectors which will express the ORF without the hydrophobic signal peptide sequence are also useful. These are constructed using bacterial expression vectors with and without N- or C-terminal His-tags. The human AMP-18 sequence lacking the 20 amino acid signal peptide and containing a His6-tag (SEQ ID NO: 16) was also expressed in bacteria.

*Pichia pastoris.* Among the simple eukaryotes, the budding yeast *P. pastoris* is gaining wide popularity as an expression system of choice for production and secretion of functional recombinant proteins (Romanos et al., 1992; Cregg et al., 1993). In this system, secretion of the foreign protein may utilize either its own signal peptide or the highly compatible yeast mating-type alpha signal. This organism will correctly process and secrete and at least partially modify the AMP-18 protein. Vectors for constitutive and regulated expression of foreign genes are developed in *Pichia* (Sears et al., 1998). In addition to a poly-linker cloning site, these vectors contain either the high expression constitutive glyceraldehyde-3-phosphate dehydrogenase (GAP) or the methanol-regulated alcohol oxidase promoter (AOX1). The latter is an extremely stringent promoter yielding insignificant product in normal culture conditions while giving the highest expression of the vectors tested in the presence of methanol, amounting to as much as 30% of the cell protein. The advantage that the yeast *Pichia* has over the mammalian and insect alternatives is that it is continuously grown in protein-free media, thus simplifying the purification of the expressed protein and eliminating extraneous bioactivities originating in the serum or the host animal cells. A pIB4 construct (inducible by methanol-containing medium) contains the complete human preAMP-18 cDNA sequence.

Baculovirus/insect cells. An alternative, frequently successful, non-mammalian eukaryotic expression system is that using recombinant Baculovirus, such as *Autographa californica*, in an insect cell culture system. As with *Pichia*, a large repertoire of convenient vectors are available in this system, containing both glutathione S-transferase (GST)- and His6-tags (SEQ ID NO: 16) (Pharmingen). Transfections are carried out into *Spodoptera frugiperda* (Sf) cells; these cells can be slowly adapted to protein-free medium to favor the purification of secreted proteins. If an endogenous signal peptide does not function in these cells, secretion of foreign proteins can also be forced using vectors containing the viral gp67 secretion signal upstream of the cloning site. Recombinant proteins can be expressed at levels ranging from 0.1-50% total cell protein. Some protein modifications may be more favored in this insect cell system relative to yeast, but still may not duplicate the mammalian system. It appears that the insect expression system would be somewhat more onerous than *Pichia*, and not entirely substitute for expression in mammalian cells. The human AMP-18 sequence lacking the 20 amino acid signal peptide and containing a His6-tag (SEQ ID NO: 16) was expressed in Baculovirus.

Mammalian cells. Modifications not detectable by immunoblot analysis may take place in mammalian cells that are not duplicated in cells of other eukaryotes. Although not as convenient as prokaryotic and simple eukaryotic systems, mammalian cells are now frequently used for both transient and continuous expression of foreign proteins. Several growth factors have been expressed and secreted in significant amounts using these systems.

The plasmid pcDNA3/human kidney 293 system: pcDNA3 contains a polylinker cloning site flanked by the strong constitutive cytomegalovirus (CMV) promoter and a SV40 polyA signal (Invitrogen). Laboratory experience is that 60-90% transient transfection levels can be achieved. To this end, PCR amplification of the human preAMP cDNA clone is performed with oligonucleotides that contain the initiation codon and native ribosome binding site (Kozak sequence) as well as suitable restriction enzyme linkers for correct orientation into pcDNA3. Favorable constructs were identified in the transient assay using the potent antibiotic blasticidin S and a vector containing the resistance gene, stable mammalian transfectant cell lines can be established "in less than one week" (Invitrogen). The available vectors also include the constitutive CMV promoter, a polylinker cloning site, an elective V5-epitope/His6-tag (SEQ ID NO: 16) and the SV40 poly(A) signal (PcDNA6/V5-His).

14. Expression and Analysis of Altered (Modified) Forms of AMP-18

Given an efficient expression system for the production of "wild-type" AMP-18, a series of mutant proteins, containing either deletions or substitutions may be created, which permit analysis of the functional domains. The amphipathic helices, the conserved cystine (C) residues and the basic amino acids doublets, which may be cleavage sites, are attractive targets. Although not as simple as an enzyme assay, the mitogenesis assay is routine and replicable, and enables "mutants" to be characterized as fast as they are constructed. Dominant negative (or positive) "mutants" are as significant as mutations exhibiting simple loss of function, because these imply interactions with other factors including possible cell receptors.

15. Biochemical and Immunoaffinity Fractionation of Expressed and Native Gastrokine Proteins In the case of some of the expressed forms of gastrokine AMP-18, the recombinant protein contains peptide tags that will permit the rapid purification of soluble protein. The presence of these tags, if they do not severely interfere with the protein's normal functions, also permit analysis of interactions with other relevant macromolecules. His6-tags (SEQ ID NO: 16) permit purification by binding the recombinant proteins to Ni-NTA resin beads (Janknecht et al., 1991; Ni-NTA resin from Qiagen). The tagged protein is bound with greater affinity than most antigen-antibody complexes and can be washed rigorously before the $N_i^{2+}$-histidine chelation complex is disrupted by excess imidazole to release the purified protein. GST-tagged recombinant proteins are purified on glutathione-agarose, washed and then eluted with reduced glutathione (Smith and Johnson, 1988). As with all the proposed expression systems, each protein preparation may be tested at the earliest possible stage for its growth factor activity.

Conventional fractionation procedures are used to achieve the desired purity, particularly in the case of the isolation of the natural protein from tissue. Pig antrum mucosa is a preferred starting point for the latter, using initial centrifugation and heat-treatment protocol, followed by a size-exclusion column: BioGel P60 is suitable, given the evidence that the 18 kDa protein exists, most probably as a monomer in the extracts. The eluant is loaded on an immunoaffinity matrix created by crosslinking anti-AMP antibodies purified on HiTrap Protein A to CNBr-activated Sepharose 4B (Pharmacia). Further modification of the immunoaffinity matrix may be helpful, either by extension of the linker to the matrix, which has proven useful in the past (Aithal et al., 1994), or by crosslinking the antibody to immobilized protein-A. Because active protein can be recovered by SDS-gel elution, active protein may also be recovered from the antigen-antibody complexes. Further fractionation could be achieved by C8 reversed-phase high-performance liquid chromatography (HPLC) column. A final step is the use of the SDS-gel elution technique with confirmation of identity by N-terminal sequencing. In all of these steps the immunodetectable AMP-18 and the growth factor activity should fractionate together.

16. AMP-18 Related Synthetic Peptides

AMP-18 may be precursor to one or several bioactive peptides. Synthetic peptides provide a convenient avenue to explore the function of a protein; peptides may mimic aspects of the function or antagonize them. If a peptide either duplicates or inhibits the protein's activity, then it suggests the identity of functional domains of the intact protein, and also provides the possibility of synthesizing specifically tagged probes to explore protein-cell interactions.

Finding that a synthetic 42 amino acid peptide, representing a middle region of the human protein, is capable of mimicking the growth factor activity of the partially fractionated antrum mucosal extracts has provided a short-cut to the analysis of AMP-18 function. This peptide (designated peptide 58-99; amino acids are at positions 58-99 of the mature protein after removal of the signal peptide) in addition to several possible protein processing sites at lysine pairs, contains one of the regions capable of extended helix formation as well as a glycine-proline loop. An added advantage of this peptide is that it contains epitopes recognized by both of the antisera disclosed herein. Some smaller peptides derived from this sequence were synthesized to focus on the bioactive regions. Initially sequences bounded by the lysine residues were studied because they may indicate distinct domains within the protein structure, by virtue of being exposed on the surface of the protein, as witnessed by the antigenicity of this region, and may be sites of cleavage in vivo to bioactive peptides. The glycine-proline region is important (see Table 1 illustrating the bioactive domains of AMP-18). Glycine-proline sequences are known to be involved in SH3 (src homology domain type 3) ligands (see Cohen et al., 1995; Nguyen et al., 1998); because SH domains are involved in protein-protein interactions that GP region of AMP-18 may be involved in the interaction of the protein with a cell surface receptor. The exact GPGGPPP (SEQ ID NO: 24) sequence found in AMP-18 has not been reported for the intracellular-acting SH3 domains, so the intriguing possibility exists that it represents a novel protein interaction domain for extracellular ligands. A 21-mer derived from amino acids at positions 97-117 of the mature sequence has activity similar to the 42-mer. This shorter peptide is useful for growth assays on various epithelial cell lines. This peptide does not express the epitope recognized by the antisera disclosed herein.

All of the AMP-18 derived peptides were synthesized by the Cancer Center Peptide Core Facility of the University of Chicago, which also confirmed the molecular mass and amino acid sequence of the purified peptides that are isolated by HPLC. The biological activity of peptide 78-119 not only provides the basis for seeking smaller peptides with mitogenic activity, but permits amino acid substitutions that have positive or negative effects to be found rapidly. Inactive peptides were tested for their ability to block the function of active peptides or intact AMP-18. The possible inclusion of D-amino acids in the peptides (in normal or reverse order) may stabilize them to degradation while permitting retention of biological function. Further the ability to synthesize active peptides enables tags that facilitate studies of the nature, tissue distribution and number of cellular receptors. Such tags include His-6 biotin or iodinated tyrosine residues appended to the peptide sequence (several of the bioactive peptides have a naturally occurring tyrosine at the C-terminus).

Synthetic peptides also permit assessment of the role of potential secondary structure on function. The finding that a 4 amino acid C-terminal extension of the active peptide 97-117, predicted to promote a helix similar to that for the intact AMP-18 sequence, led to a more active peptide 97-121, is interesting. The helix-propensity of these active peptides e.g. peptide 126-143, which resembles an anti-microbial magainin peptide, provides useful information. With respect to anti-microbial peptides, the function of the magain in class is related to their ability to form amphipathic helices (Boman, 1995). Synthetic peptides that can be locked in the helical form by lactam bridges (Houston et al., 1996) enhanced biological activity; at least one pair of appropriate acidic and basic amino acid residues for lactam formation already exist in potential helix regions of AMP-18.

Another equally significant aspect of the peptide studies is the potential availability of specific anti-AMP-18 peptides that antagonize its biological functions. Tissue culture studies show that sub-peptides of the growth-promoting peptide 78-119 can antagonize the activity of the intact peptide (see Table 1). Peptides that can occupy cellular binding sites but lack some essential residues for activity may block the action of AMP-18 and its active peptides. This makes available another set of reagents for the analysis of cellular receptors and for assessing receptor-ligand affinity constants. Availability of defined peptide antagonists is useful in whole animal studies, and may eventually serve to regulate the activity of the natural protein in humans.

17. Interactions of AMP-18 and Related Peptides with Cells: Assessment of Cell Growth Non-transformed monkey kidney epithelial cell line BSC-1 and other epithelial cell lines were used to assess effects on growth. In general, conditions were chosen for each line such that cells are grown to confluence in plastic dishes in supplemented growth medium with minimal calf (or fetal) serum for growth (Lieske et al., 1997); BSC-1 cells become confluent at $10^6$/60 mm dish with 1% calf serum. At the start of the growth assay the medium on the confluent culture was aspirated and replaced with fresh medium with minimal serum to maintain viability (0.01% for BSC-1) cells. AMP-18 preparations were added to the culture medium and 4 days later the cell monolayer was rinsed, detached with trypsin, and the cells were counted using a hemocytometer. Determination of the capacity of AMP-18 to initiate DNA synthesis was measured by the incorporation of [$^3$H]thymidine (Toback, 1980); to confirm the DNA synthesis assay, autoradiograms of leveled cells were counted (Kartha and Toback, 1985).

The protein AMP-18 is expressed in the antrum mucosa and to a lesser extent in the adjacent corpus mucosa. However, both antrum extracts and the active synthetic peptides stimulate proliferation of most simple epithelial cell lines. The major criterion used, apart from cells which might be natural targets for AMP-18 or its peptides, was that of growth control, particularly cell-density restriction. Many transformed stomach lines derived from human cancer patients are available from various sources, but most of these do not exhibit growth control. For example, a gastric AGS adenocarcinoma cell subline from Dr. Duane Smoot (Howard University College of Medicine) showed a greater degree of contact inhibition, and responded well to AMP-18 and its derived peptides. These cells do not naturally synthesize AMP-18. Similar responses were observed with the non-transformed rat IEC intestinal epithelial cells (provided by Dr. Mark Musch, Dept.

Medicine, University of Chicago); the latter show excellent epithelial cell characteristics in culture (Quaroni et al., 1979; Digass et al., 1998).

18. Receptors for AMP-18 on the Surface of Epithelial Cells

Characterization of the target cell receptors of AMP-18 is intriguing because of the apparent existence of receptors on cells which are not expected ever to contact this protein. Initial growth response assays were performed on kidney-derived epithelial cell lines, which responded well to the stomach factor. Gastric cell lines, as well as the non-transformed rat intestinal epithelial IEC-6 cells, were used to address the receptors in cells that are likely the true physiological targets for the antrum factor. The specificity for the action of this protein in vivo likely arises from the extremely tissue specific nature of its expression, rather than that of its receptor. It is possible that AMP-18 may interact with receptors shared with other growth factors. However, the additive growth stimulus of EGF and the antrum extracts suggest that AMP-18 may have novel receptors.

Protein molecules in cell membranes that interact with AMP-18 may be sought in several different ways. Pure AMP-18 or related peptides labeled, e.g. with biotin or radioactive iodine, are used to estimate the number of saturatable sites on the cell surface. Scatchard analysis of the binding values as used to determine the number and affinity of receptors. For quantitative studies, binding is measured at increasing AMP ligand concentrations, and non-specific components are identified by measuring binding in the presence of excess unlabeled factor. Iodinated growth factors have been cross-linked to cellular receptors enabling their identification (Segarini et al., 1987). Labeled AMP ligands are incubated with cells, and the bound ligand is cross-linked to the receptors by disuccinimidyl suberate. The labeled proteins are resolved by SDS-PAGE, and autodiography is used to visualize the cross-linked complex permitting an estimate of the MW of the receptor(s). Synthetic peptide mimics or antagonists permit studies of the cellular receptors, and their properties are reasonably inferred prior to future definitive identification, presumably by cloning techniques.

In addition to crosslinking studies, antibodies, or his6-tagged (SEQ ID NO: 16) AMP-18 or peptides are used to isolate cellular or mucus proteins which bind to AMP-18. As an additional approach, an immobilized AMP-18 affinity matrix can be created by using CNMBr-activated Sepharose. As a simple beginning to the analysis of the signal transduction pathway mediated by any cell receptor, a test to assay protein tyrosine kinase activity in affinity isolates is available (Yarden and Ullrich, 1988; Schlessinger and Ullrich, 1992).

19. Is AMP-18 Processed to Bioactive Peptides?

The functional molecular form(s) of AMP-18 is not known. Certainly, the ca. 18 kDa is the protein form which accumulates in antrum mucosal cells, and substantial amounts of polypeptides of lower MW are not detected with the antisera, even though they do react with pepsin fragments down to ca. 10 kDa and also with the bioactive peptide 78-119 (having only 42 amino acids). Having access to labeled or tagged AMP-18 enables a question of whether the protein is processed in antrum mucosal extracts, or by the epithelial cells which respond to it, to be explored.

20. Genes for AMP-18 in Man and Mouse

Using PCR techniques employing primers based on the sequence of the human cDNA clone, genomic clones of human and mouse preAMP-18 were obtained. The exon/intron structure (FIG. 13) is complete. Mouse AMP exons are sufficiently similar to those of human and pig to allow a sequence of the mouse gene to be assembled. Human and mouse genes have very similar structures, the mouse gene being slightly smaller. The ORF contained in exons of the mouse gene predicts a protein having 65% identity to the human and pig proteins. A 2 kb of sequence is upstream of the human gene.

21. Knockout of the AMP-18 Gene in Mouse

From the mouse map a targeting construct is designed. The construct preferably contains: [5'-TK (a functional thymidine kinase gene)—ca. 5 kb of the 5' end of AMP-18 DNA—the neomycin phosph-transferase (neo) gene under the control of the phosphoglycerate kinase (PGK) promoter—ca. 3 kb of the 3' end of the gene-3']. A considerable length of homology of the construct with the resident AMP-18 gene is required for efficient targeting. Increasing the total homology from 1.7 to 6.8 kb increases the efficiency of homologous targeting into the hrpt gene about 200-fold (Hasty et al., 1991). Beyond that total length, the efficiency increases only slightly. To facilitate the detection of homologous intergrants by a PCR reaction, it is useful to have the neo gene close to one end of the vector. The resulting transfectants can be provided by PCR with two primers, one in the neo gene and the other in the AMP-18 locus just outside of the targeting vector. Flanks extending 4 kb 5' and 4.5 kb 3' of the mouse gene have been obtained. Through homologous recombination, the coding region will be replaced by the neo gene to ensure a complete knockout of the gene are already cloned. After trimming off the plasmid sequence, the targeting cassette is transfected into ES cells and stable transfectants obtained by selection with G418, an analog of neomycin, and gancyclovir (Mansour et al., 1988). Southern blots with the probe from the flanking sequence will be used to screen for targeted homologous recombinants. Correctly targeted ES cell clones will be injected in blastocysts from C57BL/6 mice.

Male offspring obtained from surrogate mothers that have at least 50% agouti coat (embryonic stem cell (ES) cell derived) are bred with C57BL/6 mice. F1 mice that are agouti have the paternal component derived from the ES cells (agouti is dominant over black). 50% of these mice should have the knockout preAMP-18 allele. These hemizygous mice are monitored for any effect of diminished gene dosage. Homozygous knockouts are preferable. If the sole function of AMP-18 is in the stomach following birth, then viable homozygotes are expected. If these cannot be obtained, a fetally lethal defect would be indicated, and the fetal stage of abortion would be ascertained. This result would suggest an unanticipated role of the protein in normal development.

Homozygous AMP-18 knockout mice are useful for investigations of stomach morphology and function. It is expected that such knockouts will show if AMP-18 is essential, and at which stage of gastro-intestinal development it is bioactive. It is possible that the AMP-18 knockout hemizygous mice will already show a phenotype. This could occur if reduced dosage of the protein reduces or eliminates its function, or if parental imprinting or random mono-allelic expression has a significant influence. A range of possible outcomes of the AMP-18 knockout in mice include: i) no viable homozygotes, implying an essential unanticipated developmental role; ii) viable homozygotes, but with obviously impaired gastrointestinal functions; iii) no strong phenotype, i.e. the protein is not important to the development and life of the laboratory mouse. If appropriate, the generation of AMP-18 in overexpressing mice is pursued. A truncated AMP-18 protein produced in the mice could potentially create a dominant negative phenotype; knowledge gained from the experiments will further define the functional domains of the protein.

TABLE 1

BIOACTIVITY OF SYNTHETIC PEPTIDES BASED ON THE
SEQUENCE OF PRE-GASTROKINE (PRE-AMP-18)

| Name of Peptide Sequence in | #AA | AMINO ACID SEQUENCE | $K_{1/2}$, µM |
|---|---|---|---|
| Human | | | |
| 78-119 | 42 | KKTCIVHKMKKEVMPSIQSLDALVKEKKLQGKGPGGPPPKGL (SEQ ID NO: 17) | 0.3 |
| 78-88 | 11 | KKTCIVHKMKK (SEQ ID NO:14) | Inactive |
| 87-105 | 19 | KKEVMPSIQSLDALVKEKK (SEQ ID NO: 15) | Inactive |
| 104-117 | 14 | KKLQGKGPGGPPPK (SEQ ID NO: 11) | 0.8 |
| 104-111 | 18 | KKLQGKGPGGPPPKGLMY (SEQ ID NO: 18) | 1.0 |
| 97-117 | 21 | LDALVKEKKLQGKGPGGPPPK (SEQ ID NO: 12) | 0.3 |
| 97-117** | 21 | GKPLGQPGKVPKLDGKEPLAK (SEQ ID NO: 19) | Inactive |
| 97-121 | 25 | LDALVKEKKLQGKGPGGPPPKGLMY (SEQ ID NO: 13) | 0.2 |
| 109-117 | 9 | KGPGGPPPK (SEQ ID NO: 20) | 2.5 |
| 104-109 | 6 | KKLQGK (SEQ ID NO: 21) | 7.4 |
| 110-113 | 4 | GPGG (SEQ ID NO: 22) | Inactive |
| mouse | | | |
| 97-119 | 23 | LDTMVKEQK . . . GKGPGGAPPKDLMY (SEQ ID NO: 23) | 0.2 |

TABLE 2

ABBREVIATIONS FOR AMINO ACIDS

| Amino acid | Three-letter abbreviation | One-letter symbol |
|---|---|---|
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamic acid | Glu | E |
| Glutamine or glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

DOCUMENTS CITED

The following documents are incorporated by reference to the extent they relate to or describe materials or methods disclosed herein.

Aithal, N. H., et al. (1994) *Am. J. Physiol.* 266:F612-619.
Baczako, K, et al. (1995) *J. Pathol.* 176:77-86.
Blaser, M. J. et al. (1987) *Gastroenterol.* 93:371-383
Boman, H. G. (1995) *Ann. Rev. Immunol.* 13:61-92.
Cohen, G. B., et al. (1995) *Cell* 80:237-248.
Cregg, J. M., et al. (1993) *Bio/Technol.* 11:905-910.
Dignass, A. U., et al. (1998) *Eur. J. clin. Invest.* 28:554-561
Falk, P., et al. (1993) *Proc. Nat. Acad. Sci.* 90:2035-2039.
Geum, D., et al. (2002) *J. Biol. Chem.* 277:19913-19921.

Goodwin, C. S., et al., (1986) *J. Clin. Microbiol.* 39:353-356.
Hasty, P., et al. (1991) Mol. Cell. Biol. 11:5586-5591.
Houston, M. E., et al. (1996) *Biochem.* 35:10041-10050.
Huot, J., et al. (1996) *Cancer Res.* 56:273-279.
Janknecht, R., et al. (1991) *Proc. Nat. Acad. Sci. USA* 88:8972-8976
Jeon, C. J., et al. (1994) *Proc. Nat. Acad. Sci. USA* 91:9106-9110
Johnson, F. R. and McMinn, R. M. H. (1970) *J. Anat.* 107: 67-86.
Kartha, S. and Toback, F. G. (1985) *Am. J. Physiol.* 249:F967-F972
Kartha, S., et al. (1992) *Exp. Cell Res.* 200:219-226.
Kucharzik, T., et al. (2001) *Am. J. Pathol.* 159:2001-2009.
Laughlin, R. S., et al. (2) *Ann. Surg.* 232:133-142.
Lavoie, J. N., et al. (1993) *J. Biol. Chem.* 268: 3420-3429.
Lavoie, J. N. et al. (1995) *Mol. Cell Biol.* 15:505-516.
Lieske, J. C., et al. (1994) *Proc. Natl. Acad. Sci.* 91:6987-6991.
Lieske, J. C., et al. (1997) *Am. J. Physiol.* F224-F233.
Lacy, E. R. (1998) *J. Clin. Gastroenterol.* 10 (Suppl 1):72-77.
Madara, J. L. et al. (1986) *J. Cell Biol.* 102:2125-2136.
Mansour, S., et al. (1988) *Nature* 336:348.
Moore, K. S., et al. (1991) *J. Biol. Chem.* 266:19851-19857.
Musch M. W., et al. (1996) *Am. J. Physiol.* 270:C429-C436.
Nguyen, J. T., et al. (1998) *Science* 282:2088-2092.
Nomura, A., et al. (1991) *N. Engl. J. Med.* 325:1132-1136.
Nusrat, A., et al. (1992) *J. Clin. Invest.* 89:1501-1511.
Park, C. B., et al. (1997) *FEBS Lett.* 411:173-178.
Parsonnet, J., et al. (1991) *N. Engl. J. Med.* 325:1127-1131.
Podolsky, D. K. (1997) *J. Gastroenterol.* 32:122-126.
Powell, C. J., (1987) Ph.D. Dissertation, University of Chicago.
Quaroni, A., et al. (1979) *J. Cell Biol.* 80:248-265.
Romanos, M. A., et al. (1992) *Yeast* 8:423-488.
Rotimi, V. O., et al. (1990) *Afr. J. Med. med. Sci.* 19:275-280.
Sands, B. E. and Podolsky, D. K. (1996) *Ann. Rev. Physiol.* 58:253.
Schlessinger, J. and Ullrich, A. (1992) *Neuron* 9:383-391.
Sears, I. B., et al. (1998) *Yeast* 14.
Segarini, P. R., et al. (1987) *J. Biol. Chem.* 262:14655-14662.
Smith, D. B. and Johnson, K. S. (1988) *Gene* 67:31-40.
Suzuki, A., et al. (2001) *J. Cell Biol.* 152:1183-1196.
Toback, F. G. (1980) *Proc. Nat. Acad. Sci.* 77:6654-6656.
Wong, V. (1997) *Am. J. Physiol.* 273:C1859-C1867.
Yarden et al. and Ullrich (1988) *Biochemistry* 27:3113-3119.
Yoo, O. J. et al. (1982) *PNAS* 79:1049-1053.

We claim:

1. A method to stimulate migration of epithelial cells to the site of injury in the gastrointestinal tract of mammals, said method comprising:
   (a) contacting the epithelial cells with a composition comprising a protein derived from a gastrokine protein, or a peptide derived from the protein, wherein the gastrokine protein is an AMP-18 protein comprising the amino acid sequence of the SEQ ID NO: 3; and
   stimulating the migration of epithelial cells.

2. The method of claim 1 where the injury is gastritis or gastric ulcers.

3. The method of claim 1 wherein the injury is caused by non-steroidal anti-inflammatory drugs or alcohol.

4. The method of claim 1, wherein the AMP-18 protein is a recombinant AMP-18 protein comprising residues 21-185 of SEQ ID NO: 3.

* * * * *

```
                         SEQUENCE LISTING

<160> NUMBER OF SEQ ID NOS: 27

<210> SEQ ID NO 1
<211> LENGTH: 7995
<212> TYPE: DNA
<213> ORGANISM: Homo sapiens

<400> SEQUENCE: 1
agctttataa ccatgtgatc ccatcttatg gtttcaatcc atgcacagga ggaaaattgt     60
gggcacgaag tttccaaagg gaaaatttat agattggtag ttaatgaaat acagttttcc    120
tccttggcaa atttaattta ctagcttcac tgtataggaa aaagcaggaa aaaaattaaa    180
accaactcac ctccaaacct gttttgagct tttacttgtc tgcccaattg atagtttcta    240
ctctctgctt ttgatgaaaa tattttttat tatttaatg taacttctga aaactaaatt     300
atctagaagc aaataaaaag atattgcttt tatagttccc agaaggaaaa aacaaacact    360
aggaaagttc tatctatcag atgggggaga tgtgatggag gcagtgatat ttgagctgag    420
ccttgaacaa tgaacaggag tctaccaagc gagaggctag cgggtggccc tcaagataaa    480
acaacagcat gtacaaaggc atggagacat acacatcttg actcttccag gaatggtggg    540
aacgctggtg gagctagaat gtaggtacat agcataaagt ggcagacggg aagcctttgg    600
aaatcttatt acataggacc ctggatgcca ttccaatgac tttgaatttt ctgtaggctg    660
ccagcgaaat ttccaagcgt gatagagtca tgtctatcta tgcacttcag aaagacaacc    720
tcagggttaa tgaagaaaat gcattggaat ataagaaact ggtgaccaga gtgatcaatt    780
gcatgactgt tgtgaaagtc caggtgaggg gagctgtggg caaggtcaga gttgagaggc    840
atttcagaga taaatgaca gtaactaagt agatgtcagg ctgagaagaa agggctgtac     900
cagatatatg gtgctatcat taagtgagct caacattgca gaaaaggggt aggtttggtg    960
ggagttgctc acaaaacatg tttagtctaa gcaaaaccat tgccatgggc tcagataaaa   1020
gttaagaagt ggaaaccatt cctacattcc tataggagct gctatctgga aggcctagta   1080
```

```
tacacgtggc ttttcagctg tgattttgtt tgattttagg gattattctt tttctgaatc    1140
tgagcaatgt tagcgtgtaa aatactcaca cccacagctt tgactgggtg agaagttatc    1200
ataaatcata ttgagtttgt tgtgataccT tcagcttcaa caagtgatga gtcaggtcaa    1260
ctccatgtga aagttccttg ctaagcatgc agatattctg aaaggtttcc tggtacactg    1320
gctcatggca cagataggag aaattgagga aggtaagtct ttgacccac ctgataacac     1380 ctagtttgag tcaacctggt taagtacaaa tatgagaagg cttctcattc aggtccatgc    1440
ttgcctactc ctctgtccac tgctttcgtg aagacaagat gaagttcaca gtgagtagat    1500
ttttcctttt gaatttacca ccaaatgatt ggagactgtc aatattctga gatttaggag    1560
gtttgcttct tatggcccca tcatggaaag tttgttttaa aaaaattctc tcttcaaaca    1620
catggacaca gagaggggaa caacacacac caggtcctgt tggggggtgg agagtgaggg    1680
gagggaactt agaggacagg tcaatagggg cagcaaacca ccatggcaca catatacCTa    1740
tgtaacaaac ctgcacgttc tgcacatgta tccctttttt ttagaagaag aataatgaa     1800 aaaaaacctt ttttctattt atataatcat ggcatttata agcatctcta tagagaagga   1860
taattgtgct gagattagac agctgtctga gcacctcaca ctgacctatt tttaacaaaa   1920
tgactttcca catcacctga tttcggctcc atgcrggta agcagttcct aagccctaga    1980
aagtgccgat catccctcat tcttgaattc ctcctttat ttaccaaaat tcctgagcat     2040
gttcaggaaa gatgaaaagc ttattatcaa ataagtggc tgagatagac ttcttgtcac     2100
atttgttaca gtaaaatggg tctccaagaa agaaagattt gccttgggct ctagcatggc   2160
catttattta agaaagcatc tgaaacatga agctaccaca gcatctctcc tgtggttcca   2220
gacggaagcc tgagagtcta ggaggaggtg gaccgagaaa ccctgccaaa gtaactagta   2280
gtgccgggtt tctcacaaca cgatgcaaag gggctagaat cagatgacta ttttcatgtt   2340
tcaacatact acacactgga aaacgttacg gcagactcta ctttataatg gggctgcaaa   2400
tgtaaaatga ctactagaac taggtcctct taatagcagc aaagtttaaa agggtcagag   2460
ggagctccag acacaggtta gatttgattt ctctcctagt tctgctgtga acaagaggta   2520
taagtttggc caactcactt aaccectgaa gctcagttac cttatctgta aaatgattgc   2580
attgtactag gtgttctcta aaatttcttc tacctctgac ttttTaggag actaattttt   2640
aactccttTt taagctattg ggagaaaaat ttaattTttt ttcaaaagtt accttgaatc   2700
tctagagcag ttctcaaaac tattttgtcc caggcaaagg aaatgagact aggtacccag   2760
aatgaggcac cctgcataaa gctctgtgct ctgaaaacca atgtcaggga ccctgtgata   2820
aataattaaa ccaagtatcc tgggacactg ctagtgacat cgcctctgct gatcactctt   2880
gccagcgaga cactctatac ttgctttctc atcattggca tccaaactgc ctactaatcc   2940
attgctttgg aaagttttt ttaataaaaa gattatttct attaggagga aaacatccca    3000
tgttaaatag gaaattaac tgaaatcatt ttcagatgtg attttagca cttatagcca     3060 tttcaaacca tggtattcat ttatactatg ctatttattg taaaacttct ttttttttcc    3120
aaggaaaata agatagtttg ctttatttta aaacagtaac tttcttatat tggggcactg   3180
accaaaattc aatactggta caaatatgtt acctagggg tcaaaatatg tgccaggtga    3240
attttctgaa tttctctaaa gagagaattt taaaccttat aaaacaatta gaaacaagtg   3300
agtgagaggt gagcatcaac aacctgtgta acataagcca cagtacaaat ttaagctgaa   3360
taaccaagcc atgtcagtta tcccaaatca tttttgttaa tatttaggag gatacacata   3420
ttttcaataa cttaaaagtg aatctttact cctatctctt aatactcgaa gaagtataac   3480
```

-continued

```
tttcttcttt tactagattt aaataatcca aatatctact caaggtagga tgctgtcatt    3540
aactatagct gagtttatcc aaaatagaaa aatcatgaag atttataaag catttaaaa     3600 ataatcattt atagcaagtc cttgaaagct ctaaataaga aaggcagttc tctactttct    3660 aataacaccct atggtttata ttacataata taattcaaca aaacagcatt ctgaccaatg   3720
ataatttata ggaaattcat ttgccaagta tatgttttat tataaagtta atattttgac   3780
caatcttaaa aatttttaaa ctctattctg acatttccag aagtattatc ttagcaagtc   3840
atctttatga taccacttat taaactgaag agaaacaaga tggtacattc tgggttttac   3900
tttaaaaggg atttgattca ataatttgat ttatcactac ttgaaaatta catttcttc    3960 ctcagactgg atggcaatga gatgaaagca gctttcctgg ctctcaactt cccttcttca   4020 tcaattttc cagcgtttca taaggcctac actaaaaatt ctaaaactat atatcacatt    4080
aatataatta cttataatta atcagcaatt cacattatc gttaaaaacct ttatggttaa   4140 aaaatgcaag gtaagagaag aaaaaaacac attgaactag aactgaacac attggtaaaa   4200
ttagtgaata cttttcataa gcttggatag aggaagaaag aagacatcat tttgccatgt   4260
aacaggagac caatgttatt tgtgatttca gattgtcttt gctggacttc ttggagtctt   4320
tctagctcct gccctagcta actatgtaag tctcacctttt tcaagtttgc taccaaaatg   4380
catttgcaag gaaatgtgat attaaatcac tctcaatctc ttataaactt cagaatatca   4440
acgtcaatga tgacaacaac aatgctggaa gtgggcagca gtcagtgagt gtcaacaatg   4500
aacacaatgt ggccaatgtt gacaataaca acggatggga ctcctggaat tccatctggg   4560
attatggaaa tgtaggtagt caacgtgcaa ttttcacttt attgtttaaa aatacgactt    4620
ctttttaaca aaaaatgtgc atgttaacca taaagaaatt aaaaataaat tctaattaca   4680
catagcatac agttataagt aaaggtgacc attttgctca tccgattttg ttccctagag   4740
ataactactg ttaataagtg ttgcatgatc agttaaaatt caaaccaaca aacactatgt   4800
tcaagggatt gtgggtatat acaacaaata tgaacatcct tttgccttgc ctgcagatac    4860
cctcaataat gctgaaagac ttatacaaca ttactgcttc caaagcttag actatctcac    4920
tttgttttca aaggaggttt tacgaccttc taaagagatt gaaattgaca tttcacctaa    4980
aactcgggaa atgtaaatga caatattaat tggtaagaga ggaaagaaga aagaaagaag    5040
gaaggaaaga aagaaagaag gaaggaagga aagaaagaaa gaaagaaaga agagagaga    5100 aagaaagaaa aagaaaaaag agagaaagag aagaggaaag aaagagagaa ggaaaggaaa    5160
agagaagcaa agaaagagag gagcaaagaa aggaacactt agcactagtt gggagaccca    5220
actctggaat tatcagctat atatttaaca aacgttatac ttttaaatag caaactcttt     5280
attgtttcaa ttttatctgg tcaattggaa aaataatttt tgtcttatct gtctccttga    5340
aatgtgagga tcaaaggaga ctaaaacatg atagcttttta aagtctattt cagtaaaaca   5400
gacttatata gagggttttt tatcatgctg gaacctggaa ataaagcaaa ccagttagat   5460
gctcagtctc tgccctcaca gaattgcagt ctgtccccac aaatgtcagc aatagatatg   5520
attgccaagc agtgccccat ccagtgctct tatcccagct catcacgatc ttggagttcc   5580
catttctctc tgcaggtgga actgacctct gataagaaaa gctcctcgga gaacacatgc    5640
ctcactattt gccatctact ttaacagggc tttgctgcaa ccagactctt tcaaaagaag    5700
acatgcattg tgcacaaaat gaacaaggaa gtcatgccct ccattcaatc ccttgatgca    5760
ctggtcaagg aaaagaaggt aaaaataaaa ggcttttat ttttggtgag gggagaggtt     5820
```

```
ttacatcctt cagtaaataa cgagaagatc acagtcattc cctcttgact acagtatgtt      5880
gtagtgtgca gcacaaaggg ggaagttatt ggtgattgcc tgagggaagg caacttctgc      5940
cacatcaaat gctgtggctc acacctacct ctacaaccgc tgagcaaagc acttgaaacc      6000
ttgactgtta gaggagcaaa gctctggtca caccaatagg agcctcagta ctttgccaag      6060 gacattttc tgcaagagtt agttagggtt attagattta gcaaatgaaa atagaagata       6120
tccagttagg tttgaatttt aggtaagcag caggtctttt tagtataata tatcctatgc     6180
aatatttggg atatactaaa aaagatcca ttgttatctg aaattcaaat gtaactgggt       6240
attgtatatt ttgtctggcc atactaatcc aggtgagtgg aaagaagaga tccataatgt      6300
tttaaaatat ttgcctgagt tcatattcct ataactgata atgagtacc tttcattgac       6360 aaggtagaga aaataaataa actgcattct cagaagatga ttattacata gtctaatcca      6420
aggaatctat gatgaccaaa tgaggtccaa gttgcagaat aaattaagcc tcagacttct      6480
gtgtttatga aagctgagg tttcaaacca ggtaaatccc ttaggacact tagaaatgct       6540
aagatataca gaataagcta gaaatggctc ttcttcatct tgattatgga aaaatttagc      6600
tgagcaacac tcactgttgg cctcgtatac ccctcaagtc aacaaaccac tgggcttggc      6660
attcattctc tcccattctt cctttctacc tctcttttcc acactcagct tcagggtaag      6720
ggaccaggag gaccacctcc caagggcctg atgtactcag tcaacccaaa caaagtcgat      6780
gacctgagca agttcggaaa aaacattgca aacatgtgtc gtgggattcc aacatacatg      6840
gctgaggaga tgcaaggtga gtagcatccc tactgtgcac cccaagttag tgctggtggg      6900
attgtcagac tatcctcgcg cgtgtccata gtgggcacca gtgatgcagg gatggtcatc      6960
aaggccaaca tttgtgcagt gcttgctctg tgccaggtac tgttctatgt gctttaagtg      7020
tgttaactcg gttcttcaca gcaatcttat aggttctatt ttaatcctac tttatggatg      7080
aggaaactga ggtacagaga ggtcacaaaa tccttgcctg ggtcaattcc aagcattttg      7140
gctgtggatt ctgtgctctt aaatattatg gaacactgcc ttttaagtgt gaatcaagag      7200
tagactcaag tcatattcaa aagaatgcat gaatggctaa atgaaagaag aatgctaata      7260
gaatctatta actttctata gctcagacaa tcacttaatt tctggacatt caaagaacag      7320
ctgcacacaa acaaagtgtc tacctaggga cctaacttaa tggcaatttt ccagatctct      7380
gaattgattg atttcatcac aacaagtaga taaaccttga cattagcaca tagctagttt      7440
ggaaacccct actcccccaa tccctccaa gaaaagagtc cttaaataga cattaatata      7500
ggcttcttct tttctcttta ttagaggcaa gcctgttttt ttactcagga acgtgctaca     7560
cgaccagtgt actatggatt gtggacattt ccttctgtgg agacacggtg gagaactaaa     7620 caattttta aagccactat ggatttagtc atctgaatat gctgtgcaga aaaaatatgg      7680
gctccagtgg ttttttaccat gtcattctga aatttttctc tactagttat gtttgatttc     7740
tttaagtttc aataaaatca tttagcattg aattcagtgt atactcacat ttcttacaat     7800
ttcttatgac ttggaatgca caggatcaaa aatgcaatgt ggtggtggca agttgttgaa     7860
gtgcattaga ctcaactgct agcctatatt caagacctgt ctcctgtaaa gaacccttc      7920 aggtgcttca gacaccacta accacaaccc tgggaatggt tccaatactc tcctactcct     7980
ctgtccactg cttaa                                                       7995
```

<210> SEQ ID NO 2
<211> LENGTH: 752
<212> TYPE: DNA
<213> ORGANISM: Homo sapiens

<400> SEQUENCE: 2

```
catgcttgcc tactcctctg tccactgctt tcgtgaagac aagatgaagt tcacaattgt      60
ctttgctgga cttcttggag tctttctagc tcctgcccta gctaactata atatcaacgt     120
caatgatgac aacaacaatg ctggaagtgg gcagcagtca gtgagtgtca acaatgaaca     180
caatgtggcc aatgttgaca ataacaacgg atgggactcc tggaattcca tctgggatta     240
tggaaatggc tttgctgcaa ccagactctt tcaaaagaag acatgcattg tgcacaaaat     300
gaacaaggaa gtcatgccct ccattcaatc ccttgatgca ctggtcaagg aaaagaagct     360
tcagggtaag ggaccaggag gaccacctcc caagggcctg atgtactcag tcaacccaaa     420
caaagtcgat gacctgagca agttcggaaa aaacattgca acatgtgtc gtgggattcc      480
aacatacatg gctgaggaga tgcaagaggc aagcctgttt ttttactcag gaacgtgcta     540
cacgaccagt gtactatgga ttgtggacat ttccttctgt ggagacacgg tggagaacta     600
aacaattttt taaagccact atggatttag tcatctgaat atgctgtgca gaaaaaatat     660
gggctccagt ggttttacc atgtcattct gaaattttc tctactagtt atgtttgatt       720
tctttaagtt tcaataaaat catttagcat tg                                   752
```

<210> SEQ ID NO 3
<211> LENGTH: 185
<212> TYPE: PRT
<213> ORGANISM: Homo sapiens

<400> SEQUENCE: 3

```
Met Lys Phe Thr Ile Val Phe Ala Gly Leu Leu Gly Val Phe Leu Ala
  1               5                  10                  15

Pro Ala Leu Ala Asn Tyr Asn Ile Asp Val Asn Asp Asp Asn Asn Asn
             20                  25                  30

Ala Gly Ser Gly Gln Gln Ser Val Ser Val Asn Asn Glu His Asn Val
         35                  40                  45

Ala Asn Val Asp Asn Asn Asn Gly Trp Asp Ser Trp Asn Ser Ile Trp
     50                  55                  60

Asp Tyr Gly Asn Gly Phe Ala Ala Thr Arg Leu Phe Gln Lys Lys Thr
 65                  70                  75                  80

Cys Ile Val His Lys Met Lys Lys Glu Val Met Pro Ser Ile Gln Ser
                 85                  90                  95

Leu Asp Ala Leu Val Lys Glu Lys Lys Leu Gln Gly Lys Gly Pro Gly
            100                 105                 110

Gly Pro Pro Pro Lys Gly Leu Met Tyr Ser Val Asn Pro Asn Lys Val
        115                 120                 125

Asp Asp Leu Ser Lys Phe Gly Lys Asn Ile Ala Asn Met Cys Arg Gly
    130                 135                 140

Ile Pro Thr Tyr Met Ala Glu Glu Met Gln Glu Ala Ser Leu Phe Phe
145                 150                 155                 160

Tyr Ser Gly Thr Cys Tyr Thr Thr Ser Val Leu Trp Ile Val Asp Ile
                165                 170                 175

Ser Phe Cys Gly Asp Thr Val Glu Asn
            180                 185
```

<210> SEQ ID NO 4
<211> LENGTH: 7280
<212> TYPE: DNA
<213> ORGANISM: Mus sp.
<220> FEATURE:

```
<221> NAME/KEY: misc_feature
<222> LOCATION: (7084)..(7084)
<223> OTHER INFORMATION: n is a, c, g, or t
<220> FEATURE:
<221> NAME/KEY: misc_feature
<222> LOCATION: (7138)..(7138)
<223> OTHER INFORMATION: n is a, c, g, or t
```

<400> SEQUENCE: 4

```
gaattcaaac agcaggccat ctttcaccag cactatccga atctagccat accagcattc     60
tagaagagat gcaggcagtg agctaagcat cagacccctg cagccctgta agctccagac    120
catggagaag aggaaggttg tgggttcaag gagcttttca gagtggaaat ctgtggatca    180
gtgatttata aaacacagtt tccccctta ttagatttga accaccagct tcagttgtag    240
aagagaacag gttaaaaaat aataagtgtc agtcagttct ccttcaaaac tattttaaac    300
gtttacttat tttgccaagt gacagtctct gcttcctctc ctaggagaag tcttccctta    360
ttttaatata atatttgaaa gttttcatta tctagagcag tggttctcat cctgtgggcc    420
atgagccctt tgggggggtt gaacgaccct ttcacagggg tcacatatca gatatcctgc    480
atcttagcta tttacattat gattcataac agtagcaaaa ttagttagga agtaggaaca    540
aaataacgtt atggttgtgg tcaccactat gttagagggt ccgcagcatt cagagggttg    600
agaactgttg ttctagaggc aaataagaag acagagttcc ttgatagggc ccagaggcag    660
tgaaagaagt ttccacgtag aaagtgaaga aggtctggtg tccgaagcag tgaggaactt    720
aaaaaaagaa accaaaaaac attgccaact aacagtccag gagaagagcg gggcatgaaa    780
ggctgagttc ccatgggatg ccttgaatgg aatcagagtg tgggaaaatt ggtgtggctg    840
gaaggcaggt gccgggcatc tcagacgctg gtagctgggg aaacaggaaa ccccttagg    900
atcccaagat gccattccaa tgagcttgag attttttctca tggactgcca gtgaatgttt    960
ctacgctccg gaaattaatg tttacttatt ttccatattc taggggagaa ccctgggaaa   1020
aatggaggac attcattgaa atatctgagt cctgggataa ggcaggcttg gtcctacaac   1080
tctggtaaaa gtccatcagg aagtgccttg accaaggctg gagtgagag ctgttggtga   1140
gatgtaaggg caaggtttag ttgctagata tgtagatggc aagatggtgc tgccaacagc   1200
ccccagagct ctaacccact gagaaaccca ggaatgaatg atgggagatg gctttggtgc   1260
cagctgctag tgacatggct ggaaagctgc actggcttcg aggccagaca attcctcaag   1320
gaaacatctg gccagggtgc aagggccagt ttccttcctt ggagttcctt tcacagctaa   1380
gaacatcatc ccccaaccac tggttttgtt aaaaagtttt cagtatgact tgagcatggt   1440
caagaagcat agagaggggg aaataagggg ggaaggagct ggagaaagct tacaatagga   1500
ctgggtaaag ggaaggagaa gaaaccattc ccgcattccc ataggagcca gtaccaggaa   1560
gggcaggtgt acacacagat ctcatctaag gccatgtttg gtttagggat tactcttctc   1620
ccgaatctga gcagcagcaa tacgtaaaat acccacaccc atggcttcca tattccagaa   1680
cttatcacaa accgtgtaga gttactgag ataccttcgt cagaggatga gtcagaggcc   1740
tcctgcctaa gggccctact gagcaggcag ctaaaggctt ccgggcctct gcagctccac   1800
agatacagga gagggaagca gataagccgt ggactccacc tgagcacacc tagcttgagc   1860
aaagctggtc aggtacaaat agcagagggc tgaatgtctg tgagcacgcc gcctgatcct   1920
ctgctccacc acactcctgc cgccatgaag ctcacagtaa gtcagatctt cttttcaatg   1980
cagcaccata caacattaat agtcaggggt gaggggtct gactcttacg gcactgttac   2040
catagtggaa atattctcct ttcttttcat ggaatcatgg tgtttacaag catgtccata   2100
```

-continued

```
gagaagaaga attgccccgg aagagcctgt cacaggctga atactgtaga attgtctttc    2160
acaccatctg ttccaaggtt ctacttaaga cgagcagtct ctgggctcca gaaagagtct    2220
ttcttagcct tgatctcttt cttatttctg atttctcctt tcttatccat gatttccact    2280
tttaccagtt ctgggcatgt tccggtcaga ctggaagatc actgttgtca aaactagtct    2340
tcaacactct tggctgttaa catgaaaaca acggtccttg ggccctgtgc aagcatttct    2400
tggagaaagt ctctggggat gaagctatct cagtttcccc actgaagtcc taggatacag    2460
aggctcaaac agagtgcaca tattcaattt cagcatactc tattggcgct gctttatgaa    2520
tcatatgaat ttatggaatt ggaaatgtaa actatgacca agaagcgtcc acctcagaac    2580
aggttgggtg gggaactcca agcacaggcc agagggctgc gtttctcttc tagttctgtc    2640
tagaggagtg gttctcgacc ttcctaatgc tgtgacccct taatacagtt cctcacgttg    2700
tcgtgactcc cagccataaa attactttca ttgctactgc ataactgtaa ttttgctacc    2760
attatgagtt gtaatgtaaa tatctgatat gcaagatacc agataaccta agaaacggtt    2820
gtttgacctt taaggggtc acaacccaca ggtggagaac tactggtcta gggtcccttta   2880 cagtccttta gctgcctcat ttacaggaga taacatcatg ctcaaaaact ccctccacat    2940
ttggcttttt gggttgtttt gttttgtttt tcaagacagg gtttctctgt gtagccctgg    3000
ctgtcctgga actcacctttt gtagaccagg ctggcctcga actcagaaat ccgcctgctt    3060
ctgcctcctg agcgctggga ttaaaggcgt gcgccaccat gtctggctca catctggctt    3120
tttaagagac cgattttaac ttcttgcatt gaaataaat atagtagaaa tgcttaacct    3180
actaagacaa taaaaacagg attccttctg ctaggaagaa cacgttccag actaaggaaa    3240
aaaacctttt cagggctttc attacactgt gccatgcact aattttatgt tttcttcatc    3300
agttttcagt gtctgaaatt cagtgtcaaa attctaagac tacatatgaa tatcattaca    3360
gtaactcagc aattctatgt taccagtaag ttttttctgta gtttaaaaaa aaggtggaag    3420
aagaaagcac agatagttta gcacatgggt aaaatcagta actatttctg atgagcttgg    3480
tgaagatgct gtaaaccatg cgaccaccag tcctgttctc tgtgctttca gatgttcgtc    3540
gtgggtctgc ttggcctcct tgcagctcct ggttttgctt acgtaagtct cattttttctg    3600 aagttcattg tcaaaactgc atttacagtg aaatgtgatc ttaagtcacc ctctgcttct    3660
tatgaacatt agacggtcaa catcaatggt aatgatggca atgtagacgg aagtggacag    3720
cattcggtga gcatcaatgg tgtgcacaac gtggccaata tcgacaacaa taacggctgg    3780
gactcctgga atagcctctg ggactatgaa aacgtatgta atggacacac agggtaaaga    3840
tatggtgtag ccaccaccca ttaaaatttc tgaggtgaat tctagctgtt catgaacatt    3900
aaaagctacc agtaaaagtg cccattccac tcaaaacaat tttactttttt tgcatataat    3960 tattgctaat aagtattaca caataggtcg aaattcaaag ggatcaatag taaggataaa    4020
aactatgtac aaagacaaac acagcatcct ttggtcttcc ctgcagagag tctccatgat    4080
gttaaaggtc caatgtttta tggaggctga atgaaatacg aatgcctctg tgatggaaaa    4140
ggcccaacat cttatggaga atgagtgaag tatgaatgct attagttgta agagaaggcg    4200
atgcaaagca acacttggca ccacctgcca attactactt tcctatttaa atgtagttta    4260
aaaagcaaag cctgtcttcc ctgcctcctg gaaacactgc ggatggaggt agaccaaggt    4320
atgacagcct ttaaaagttt gtcagcaaaa cactccccca tacacacata cacacaccct    4380
cctactacac tggaactgaa gcaaaggcag tgggttagat atatccaccc tctaagagtt    4440
```

```
tgcaggtcat ctatatatga tagccagaga cacaactgca ggacagccag actctgagca    4500
ctctccccag ctccttgtag ctctgtttca gtggtgactt gtgacaagaa tcctggggaa    4560
cctgtgcctc actgttctct gtcttcttta atagagtttc gctgccacga gactcttctc    4620
caagaagtca tgcattgtgc acagaatgaa caaggatgcc atgccctccc ttcaggacct    4680
cgatacaatg gtcaaggaac agaaggtaaa gtcctgcctt cttctttgga gtgacaggaa    4740
gtcttacagt ctccagtaca cagtgaagtc accccattc cctctttggt ggagcatgac     4800
agcatgtttg tcatgataaa tgccacaaac atgtaaaact gttcagtgtc tgcctgaatg    4860
gagggtggct tccactgtgt cagatgccgt ggcccacatc tgcctctgca gggtccagta    4920
aagcactggc tatcttgagt gtcagagacc caaggtctg tacacttcag tacaagccct      4980
ccatatttca agggcacact cctacagtcg ttggggttat cagaactagc aaacatagag    5040
actggatttt cagatgaaaa gaaatccttt ttaaagtcta agtatgcctt atacaatgtt    5100
tgagatattc tcaatactaa aaaaaaaaaa attgttgctt gcttgaaaat caaatgtaac    5160
caagtgtcct atatccagtg tcaatcatgg ctgtagtaga tgggaagagg gagcccgtgg    5220
ttttcacagt cagacgcctg agttattctt ctaagtgata aattggttcc tataacaagc    5280
aagccagtga atataaataa gctctatctc agaagttatc ctgtagtgct accctagaat    5340
ctaagagagc aaaagtgctt caaatttcag aataagtttt gctttggact tctgttttc     5400 taaacaacta taacttcaaa ccatctaagc ctcgtgggac acttagaaat accaagccat    5460
tcaaagctag aattgtttct tcaccttact tgaaaacaaa atgacaacca aaaattgtcc    5520
ccactgccct tgtacatctt cagatcagta aagtcctggg ctcagggatc attcactttc    5580
tttctttcct ttcacactca acttcagggt aaagggcctg gaggagctcc tcccaaggac    5640
ttgatgtact ccgtcaaccc taccagagtg gaggacctga atacattcgg accaaagatt    5700
gctggcatgt gcagggcat ccctacctat gtggccgagg agattccagg tgtgtaccct     5760
gagatgctgt atatcccaat gcagtactga gagagccatc agacactcta aagtgtgacc    5820
acagacggac caatcatgtg gattatcaga gcaaacactt gcttgctcct tgtcagacag    5880
ttgtccatgc ttcaaaagtt cattaaaaaa aatagttcac aggctcctca cagaaacctt    5940
agtagaatcc acagcttctg ctcttagtct tacttttag aaactgagac ccagagaaag     6000
gtcacaaaac ttttgtctgg ctcaggttct atgtctttaa ctttatagaa taccgtcttt    6060
ctgggtgggt gggctctaga gtaaacttca agtgagttca aggaaagcat gagaagtagg    6120
gaagaccaaa tgaaggaga atgccaatga aatctatcga ttctatagcg ccaatgctta     6180
actcctaggc gttcaaagaa tagtatccac aaggtgtcag cctaagatcc taatctaaca    6240
gcaagttttc agatctctga agtgaaaaga gaaagcaaga gaggaacaga gacagaaaca    6300
gtaagagaca gagaggcaga gacaaagaga cagggagaat agagagggat taaaattaat    6360
atatagttta gaaattacga ctcctcacag tccctgcaga gtcctaggat aggcactgat    6420
ttggacttct tttcttctca ctaggaccaa accagccttt gtactcaaag aagtgctaca    6480
cagctgacat actctggatt ctgcggatgt ccttctgtgg aacatcagtg gagacatact    6540
agaagtcaca ggaaaacaac ccgtgggctc tgaccatcgc aatgcttgat tatgagagtg    6600
ttctctgggg gttgtgatta gcttctttaa ggctcaataa acccacgtgg cagcacatcc    6660
agtttgtaat gacatgcctc atgacttcta tgggagtcca atgtggcacc tgccagcctg    6720
tattcaggac ctctccgcta taagcatccc ctccagagtt ttcaaatact acaaagcaca    6780
gcctgggttt gggctcagat aggccactgc tgcctgacta cattacagac aaacaagttt    6840
```

```
taaaagaaag aaaaaagagc tcagagtggc tggaatcagc aagggtgttt ttcctgcaag    6900
gagccagaag tatcaataat cacccaagga ggagacactg ggaatgagag actagaacac    6960
acgcctgcag atacggagaa cctcagcatt gccgctctct cccataactg cacaccccct    7020
tctgtaaact ctgcttcttt cttcacctg aagatggccc ttgcttttt ttattatagg    7080 acangataac tagaccagaa agtcaacctg actctctaca tttatatgtc ttcccagntc    7140
aagaaatatt atttactggt gaatggcact tctatattcc cttggttcaa taagtctaca    7200
ggatccattc attgacaggc caagagtgag atcacatgat acccaagcac atgggtcttt    7260
ccttgaagga gaaggatcca                                                  7280

<210> SEQ ID NO 5
<211> LENGTH: 543
<212> TYPE: DNA
<213> ORGANISM: Mus sp.

<400> SEQUENCE: 5
atgttcgtcg tgggtctgct tggcctcctt gcagctcctg gttttgctta cacggtcaac      60
atcaatggta tgatggcaa tgtagacgga agtggacagc attcggtgag catcaatggt     120
gtgcacaacg tggccaatat cgacaacaat aacggctggg actcctggaa tagcctctgg     180
gactatgaaa acagtttcgc tgccacgaga ctcttctcca agaagtcatg cattgtgcac     240
agaatgaaca aggatgccat gccctccctt caggacctcg atacaatggt caaggaacag     300
aagggtaaag ggcctggagg agctcctccc aaggacttga tgtactccgt caaccctacc     360
agagtggagg acctgaatac attcggacca aagattgctg gcatgtgcag gggcatccct     420
acctatgtgg ccgaggagat tccaggacca accagccctt tgtactcaaa gaagtgctac     480
acagctgaca tactctggat tctgcggatg tccttttgtg aacatcagt ggagacatac     540 tag                                                                    543

<210> SEQ ID NO 6
<211> LENGTH: 184
<212> TYPE: PRT
<213> ORGANISM: Mus sp.

<400> SEQUENCE: 6

Met Lys Leu Thr Met Phe Val Val Gly Leu Leu Gly Leu Leu Ala Ala
  1               5                  10                  15

Pro Gly Phe Ala Tyr Thr Val Asn Ile Asn Gly Asn Asp Gly Asn Val
                 20                  25                  30

Asp Gly Ser Gly Gln Gln Ser Val Ser Ile Asn Gly Val His Asn Val
             35                  40                  45

Ala Asn Ile Asp Asn Asn Asn Gly Trp Asp Ser Trp Asn Ser Leu Trp
         50                  55                  60

Asp Tyr Glu Asn Ser Phe Ala Ala Thr Arg Leu Phe Ser Lys Lys Ser
 65                  70                  75                  80

Cys Ile Val His Arg Met Asn Lys Asp Ala Met Pro Ser Leu Gln Asp
                 85                  90                  95

Leu Asp Thr Met Val Lys Glu Gln Lys Gly Lys Gly Pro Gly Gly Ala
                100                 105                 110

Pro Pro Lys Asp Leu Met Tyr Ser Val Asn Pro Thr Arg Val Glu Asp
            115                 120                 125

Leu Asn Thr Phe Gly Pro Lys Ile Ala Gly Met Cys Arg Gly Ile Pro
        130                 135                 140
```

```
Thr Tyr Val Ala Glu Glu Ile Pro Gly Pro Asn Gln Pro Leu Tyr Ser
145                 150                 155                 160

Lys Lys Cys Tyr Thr Ala Asp Ile Leu Trp Ile Leu Arg Met Ser Phe
                165                 170                 175

Cys Gly Thr Ser Val Glu Thr Tyr
            180
```

<210> SEQ ID NO 7
<211> LENGTH: 597
<212> TYPE: DNA
<213> ORGANISM: Sus scrofa

<400> SEQUENCE: 7

```
atgcctgact ctcacttca ttgcattggt gaagccaaga tgaagttcac aattgccttt      60
gctggacttc ttggtgtctt cctgactcct gcccttgctg actatagtat cagtgtcaac    120
gacgacggca acagtggtgg aagtgggcag cagtcagtga gtgtcaacaa tgaacacaac    180
gtggccaacg ttgacaataa caatggatgg aactcctgga atgccctctg ggactataga    240
actggctttg ctgtaaccag actcttcgag aagaagtcat gcattgtgca caaaatgaag    300
aaggaagcca tgccctccct tcaagccctt gatgcgctgg tcaaggaaaa gaagcttcag    360
ggtaagggcc aggggggacc acctcccaag agcctgaggt actcagtcaa ccccaacaga    420
gtcgacaacc tggacaagtt tggaaaatcc atcgttgcca tgtgcaaggg gattccaaca    480
tacatggctg aagagattca aggagcaaac ctgatttcgt actcagaaaa gtgcatcagt    540
gccaatatac tctggattct aacatttcc ttctgtggag aatagcgga gaactaa         597
```

<210> SEQ ID NO 8
<211> LENGTH: 185
<212> TYPE: PRT
<213> ORGANISM: Sus scrofa

<400> SEQUENCE: 8

```
Met Lys Phe Thr Ile Ala Phe Ala Gly Leu Leu Gly Val Phe Leu Thr
1               5                   10                  15

Pro Ala Leu Ala Asp Tyr Ser Ile Ser Val Asn Asp Asp Gly Asn Ser
                20                  25                  30

Gly Gly Ser Gly Gln Gln Ser Val Ser Val Asn Asn Glu His Asn Val
            35                  40                  45

Ala Asn Val Asp Asn Asn Gly Trp Asn Ser Trp Asn Ala Leu Trp
        50                  55                  60

Asp Tyr Arg Thr Gly Phe Ala Val Thr Arg Leu Phe Glu Lys Lys Ser
65                  70                  75                  80

Cys Ile Val His Lys Met Lys Lys Glu Ala Met Pro Ser Leu Gln Ala
                85                  90                  95

Leu Asp Ala Leu Val Lys Glu Lys Lys Leu Gln Gly Lys Gly Pro Gly
                100                 105                 110

Gly Pro Pro Pro Lys Ser Leu Arg Tyr Ser Val Asn Pro Asn Arg Val
            115                 120                 125

Asp Asn Leu Asp Lys Phe Gly Lys Ser Ile Val Ala Met Cys Lys Gly
        130                 135                 140

Ile Pro Thr Tyr Met Ala Glu Glu Ile Gln Gly Ala Asn Leu Ile Ser
145                 150                 155                 160

Tyr Ser Glu Lys Cys Ile Ser Ala Asn Ile Leu Trp Ile Leu Asn Ile
                165                 170                 175
```

```
Ser Phe Cys Gly Gly Ile Ala Glu Asn
            180                 185

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Met Arg Gly Ser His His His His His His Gly Ser
  1               5                  10

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Consensus
      sequence
<220> FEATURE:
<221> NAME/KEY: MOD_RES
<222> LOCATION: (4)
<223> OTHER INFORMATION: Lys or Gln
<220> FEATURE:
<221> NAME/KEY: MOD_RES
<222> LOCATION: (6)
<223> OTHER INFORMATION: Leu or deleted with the proviso that residues 6
      and 7 are either both present or both deleted
<220> FEATURE:
<221> NAME/KEY: MOD_RES
<222> LOCATION: (7)
<223> OTHER INFORMATION: Gln or deleted with the proviso that residues 6
      and 7 are either both present or both deleted
<220> FEATURE:
<221> NAME/KEY: MOD_RES
<222> LOCATION: (14)
<223> OTHER INFORMATION: Pro or Ala

<400> SEQUENCE: 10

Val Lys Glu Xaa Lys Xaa Xaa Gly Lys Gly Pro Gly Gly Xaa Pro Pro
  1               5                  10                  15

Lys

<210> SEQ ID NO 11
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Lys Lys Leu Gln Gly Lys Gly Pro Gly Gly Pro Pro Pro Lys
  1               5                  10

<210> SEQ ID NO 12
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Asp Ala Leu Val Lys Glu Lys Lys Leu Gln Gly Lys Gly Pro Gly
  1               5                  10                  15
```

```
Gly Pro Pro Pro Lys
            20

<210> SEQ ID NO 13
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Leu Asp Ala Leu Val Lys Glu Lys Lys Leu Gln Gly Lys Gly Pro Gly
  1               5                  10                  15

Gly Pro Pro Pro Lys Gly Leu Met Tyr
            20                  25

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Lys Lys Thr Cys Ile Val His Lys Met Lys Lys
  1               5                  10

<210> SEQ ID NO 15
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Lys Lys Glu Val Met Pro Ser Ile Gln Ser Leu Asp Ala Leu Val Lys
  1               5                  10                  15

Glu Lys Lys

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: 6-His tag

<400> SEQUENCE: 16

His His His His His His
  1               5

<210> SEQ ID NO 17
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Lys Lys Thr Cys Ile Val His Lys Met Lys Lys Glu Val Met Pro Ser
  1               5                  10                  15

Ile Gln Ser Leu Asp Ala Leu Val Lys Glu Lys Lys Leu Gln Gly Lys
            20                  25                  30
```

```
Gly Pro Gly Gly Pro Pro Lys Gly Leu
        35                  40

<210> SEQ ID NO 18
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Lys Lys Leu Gln Gly Lys Gly Pro Gly Gly Pro Pro Lys Gly Leu
  1               5                  10                  15

Met Tyr

<210> SEQ ID NO 19
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Lys Pro Leu Gly Gln Pro Gly Lys Val Pro Lys Leu Asp Gly Lys
  1               5                  10                  15

Glu Pro Leu Ala Lys
            20

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Lys Gly Pro Gly Gly Pro Pro Pro Lys
  1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Lys Lys Leu Gln Gly Lys
  1               5

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Pro Gly Gly
  1
```

```
<210> SEQ ID NO 23
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Leu Asp Thr Met Val Lys Glu Gln Lys Gly Lys Gly Pro Gly Gly Ala
 1               5                  10                  15

Pro Pro Lys Asp Leu Met Tyr
            20

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence:
      Glycine-proline synthetic peptide

<400> SEQUENCE: 24

Gly Pro Gly Gly Pro Pro Pro
 1               5

<210> SEQ ID NO 25
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Lys or Gln
<220> FEATURE:
<221> NAME/KEY: MOD_RES
<222> LOCATION: (14)
<223> OTHER INFORMATION: Pro or Ala

<400> SEQUENCE: 25

Val Lys Glu Xaa Lys Leu Gln Gly Lys Gly Pro Gly Gly Xaa Pro Pro
 1               5                  10                  15

Lys

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Lys or Gln
<220> FEATURE:
<221> NAME/KEY: MOD_RES
<222> LOCATION: (12)
<223> OTHER INFORMATION: Pro or Ala

<400> SEQUENCE: 26

Val Lys Glu Xaa Lys Gly Lys Gly Pro Gly Gly Xaa Pro Pro Lys
 1               5                  10                  15

<210> SEQ ID NO 27
```

```
<211> LENGTH: 177
<212> TYPE: PRT
<213> ORGANISM: Artificial Sequence
<220> FEATURE:
<223> OTHER INFORMATION: Description of Artificial Sequence: Synthetic
      fusion construct

<400> SEQUENCE: 27

Met Arg Gly Ser His His His His His His Gly Ser Asn Tyr Asn Ile
1               5                   10                  15

Asp Val Asn Asp Asp Asn Asn Asn Ala Gly Ser Gly Gln Gln Ser Val
            20                  25                  30

Ser Val Asn Asn Glu His Asn Val Ala Asn Val Asp Asn Asn Asn Gly
            35                  40                  45

Trp Asp Ser Trp Asn Ser Ile Trp Asp Tyr Gly Asn Gly Phe Ala Ala
        50                  55                  60

Thr Arg Leu Phe Gln Lys Lys Thr Cys Ile Val His Lys Met Lys Lys
65                  70                  75                  80

Glu Val Met Pro Ser Ile Gln Ser Leu Asp Ala Leu Val Lys Glu Lys
                85                  90                  95

Lys Leu Gln Gly Lys Gly Pro Gly Gly Pro Pro Pro Lys Gly Leu Met
                100                 105                 110

Tyr Ser Val Asn Pro Asn Lys Val Asp Asp Leu Ser Lys Phe Gly Lys
                115                 120                 125

Asn Ile Ala Asn Met Cys Arg Gly Ile Pro Thr Tyr Met Ala Glu Glu
            130                 135                 140

Met Gln Glu Ala Ser Leu Phe Phe Tyr Ser Gly Thr Cys Tyr Thr Thr
145                 150                 155                 160

Ser Val Leu Trp Ile Val Asp Ile Ser Phe Cys Gly Asp Thr Val Glu
                165                 170                 175

Asn
```